United States Patent
Wu et al.

(10) Patent No.: US 11,541,049 B2
(45) Date of Patent: Jan. 3, 2023

(54) TETRAHYDROISOQUINOLINE DERIVATIVES, PREPARATION PROCESS AND USE THEREOF

(71) Applicant: SICHUAN KELUN-BIOTECH BIOPHARMACEUTICAL CO., LTD., Sichuan (CN)

(72) Inventors: Yongyong Wu, Sichuan (CN); Jiaqiang Cai, Sichuan (CN); Guangchao Zhang, Sichuan (CN); Shuangshuang Duan, Sichuan (CN); Chaolei Wang, Sichuan (CN); Lichun Wang, Sichuan (CN); Jingyi Wang, Sichuan (CN)

(73) Assignee: Sichuan Kelun-Biotech Biopharmaceutical Co., Ltd., Sichuan (CN)

( * ) Notice: Subject to any disclaimer, the term of this patent is extended or adjusted under 35 U.S.C. 154(b) by 32 days.

(21) Appl. No.: 16/965,450

(22) PCT Filed: Mar. 18, 2019

(86) PCT No.: PCT/CN2019/078493
§ 371 (c)(1),
(2) Date: Jul. 28, 2020

(87) PCT Pub. No.: WO2019/184744
PCT Pub. Date: Oct. 3, 2019

(65) Prior Publication Data
US 2021/0052576 A1    Feb. 25, 2021

(30) Foreign Application Priority Data
Mar. 28, 2018 (CN) .......................... 201810264533.9

(51) Int. Cl.
| | |
|---|---|
| *C07D 403/14* | (2006.01) |
| *A61K 31/496* | (2006.01) |
| *A61P 7/02* | (2006.01) |
| *A61K 31/4725* | (2006.01) |
| *A61K 45/06* | (2006.01) |
| *C07D 401/14* | (2006.01) |
| *C07D 413/14* | (2006.01) |
| *C07D 401/10* | (2006.01) |

(52) U.S. Cl.
CPC ........ *A61K 31/496* (2013.01); *A61K 31/4725* (2013.01); *A61K 45/06* (2013.01); *A61P 7/02* (2018.01); *C07D 401/10* (2013.01); *C07D 401/14* (2013.01); *C07D 403/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 9,738,655 B2* | 8/2017 | Pinto | .................... C07D 413/14 |
| 9,944,625 B2* | 4/2018 | Orwat | ....................... A61P 7/02 |

FOREIGN PATENT DOCUMENTS

| | | |
|---|---|---|
| CN | 103974938 A | 8/2014 |
| CN | 103987696 A | 8/2014 |
| CN | 105228996 A | 1/2016 |
| CN | 107540659 A | 1/2018 |
| WO | 2013055984 A1 | 4/2013 |
| WO | 2013056060 A | 8/2013 |
| WO | 2014059203 A1 | 4/2014 |
| WO | 2019144811 A1 | 8/2019 |

OTHER PUBLICATIONS

Extended European Search Report dated Jul. 16, 2021 in corresponding EP Application No. 19775093.8.
International Search Report dated May 29, 2019 in International Application No. PCT/CN2019/078493.
Written Opinion dated May 29, 2019 in International Application No. PCT/CN2019/078493.
Pinto et al. "Discovery of a Parenteral Small Molecule Coagulation Factor XIa Inhibitor Clinical Candidate (BMS-962212)" J. Med. Chem., 2017, vol. 60, pp. 9703-9723.

* cited by examiner

*Primary Examiner* — Medhanit W Bahta
(74) *Attorney, Agent, or Firm* — Ice Miller LLP

(57) ABSTRACT

Provided are tetrahydroisoquinoline derivatives, the preparation and use thereof. More specifically, provided are the tetrahydroisoquinoline derivatives or a pharmaceutically acceptable salt, ester, stereoisomer, tautomer, polymorph, solvate, isotopically labeled compound, metabolite or prodrug thereof. Further provided are a preparation process of the compound, the intermediates, a pharmaceutical composition comprising the compound and the use thereof in the treatment or prevention of a thromboembolic disorder.

21 Claims, No Drawings

TETRAHYDROISOQUINOLINE DERIVATIVES, PREPARATION PROCESS AND USE THEREOF

CROSS-REFERENCE TO RELATED APPLICATION

This application is a Section 371 of International Application No. PCT/CN2019/078493, filed Mar. 18, 2019, which was published in the Chinese language on Oct. 3, 2019, under International Publication No. WO 2019/184744 A1, which claims priority under 35 U.S.C. § 119(b) to Chinese Patent Application No. 201810264533.9, filed on Mar. 28, 2018, the disclosures of which are incorporated herein by reference in their entireties.

TECHNICAL FIELD

Provided are tetrahydroisoquinoline derivatives, a preparation process thereof, and the use of the compound in the treatment or prevention of thromboembolic disorder.

BACKGROUND

Thromboembolic diseases such as stroke, myocardial infarction, deep venous thrombosis are clinically common causes of death. Anticoagulants are commonly used drugs in the clinical treatment of thromboembolic diseases. Normal coagulation is a balanced process under tight regulation, which requires maintaining the fluid state of the blood under normal physiological conditions, and having at the same time a mechanism for quick plug formation at the injured site to prevent life-endangering blood loss. Some of the current anticoagulants influence the normal coagulation process, and thus have side effects such as hemorrhage. The coagulation process can be divided into three interdependent pathways: the extrinsic, the intrinsic and the common pathway. Coagulation factor XIa is located near the start of the intrinsic coagulation pathway, and the initiation of the intrinsic coagulation pathway and the formation of coagulation factor XIa (activated by thrombin or XIIa) are very important for maintaining the integrity of the blood clot. However, coagulation factor XIa is not necessary for normal hemostasis. Studies have shown that increased levels of coagulation factor XI are associated with the male venous thrombosis and myocardial infarction, and increased risk of cerebrovascular disease and coronary artery disease. Therefore, it is considered that inhibition of XIa can effectively inhibit thrombosis without causing significant hemorrhage.

Some applications such as WO2013055984 disclose various inhibitors of coagulation factor XIa. WO2013056060 discloses BMS-962212, a coagulation factor XIa inhibitor. However, the known coagulation factor XIa inhibitors show shortages in in vivo metabolic stability, safety and other aspects. Therefore, there is an urgent need for a new coagulation factor XIa inhibitor with stronger inhibitory effect, better selectivity, metabolic stability, lower toxicity and less side effect.

SUMMARY

With extensive work, the inventors have found a tetrahydroisoquinoline derivative, of which the affinity for coagulation factor XIa is over three times that of BMS-962212, the current best-in-class compound. More surprisingly, after intravenous administration in various animal species (rat, rabbit, dog), the exposure of compounds of the present disclosure (Example 5) in blood is 3-25 times that of BMS-962212. Meanwhile, smaller distribution volume and longer half-life are achieved. In view that coagulation factor XIa is an extracellular target in blood, such pharmacological properties (which are superior over that of BMS-962212) on the one hand can reduce side effects by reducing the drug dosage. At the same time, since the compounds of the present disclosure are more primarily distributed in blood as compared with BMS-962212, with much less amount into other tissues and cells, the compounds of the present disclosure show lower toxicity at the same level of blood exposure. It would not be difficult to understand the cause of the unexpected effect achieved by the compounds of the present disclosure that in spite of the high mortality in the rats of 75 mg/kg group treated with BMS-962212, during the in vivo acute toxicity test, no abnormality was observed in rats administered intravenously with the compounds of the present disclosure at a dosage of 200 mg/kg. The compounds of the present disclosure possess significant advantages over those in the prior art in regards of high activities, high blood exposure and lower in vivo toxicity.

In one aspect, provided is a tetrahydroisoquinoline compound, which can be used as coagulation factor XIa inhibitor. Specifically, provided is a compound of formula (I) or a pharmaceutically acceptable salt, ester, stereoisomer, tautomer, polymorph, solvate, isotopically labeled compound, metabolite or prodrug thereof,

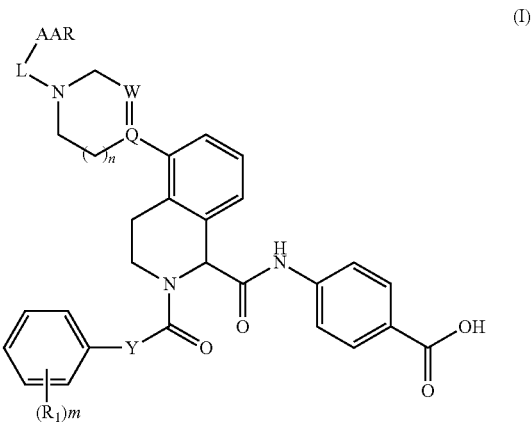

(I)

wherein:

"$=\!=\!=\!=$" represents a single bond or a double bond;

each $R_1$, at each occurrence, is independently selected from the group consisting of halogen, halo $C_{1-6}$ alkyl, nitro, cyano and 5-6 membered heteroaryl;

Y is selected from the group consisting of

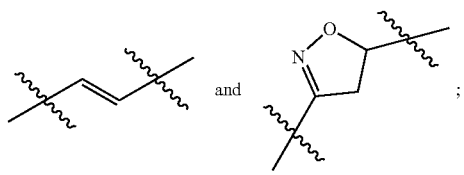

;

W is selected from the group consisting of $CR_2$, $CR_{2a}R_{2b}$ and $C(=\!O)$;

Q is selected from the group consisting of N, C and $CR_3$;

each $R_2$, $R_{2a}$, $R_{2b}$ and $R_3$ is independently selected from the group consisting of H and $C_{1-6}$ alkyl;

L is selected from the group consisting of chemical bond, $C_{1-4}$ alkylene and a bivalent radical formed by any combination of 1-4 groups selected from the group consisting of —$CH_2$—, —C(=O)—, —NH—;

AAR represents amino acid residue; or

AAR is selected from the group consisting

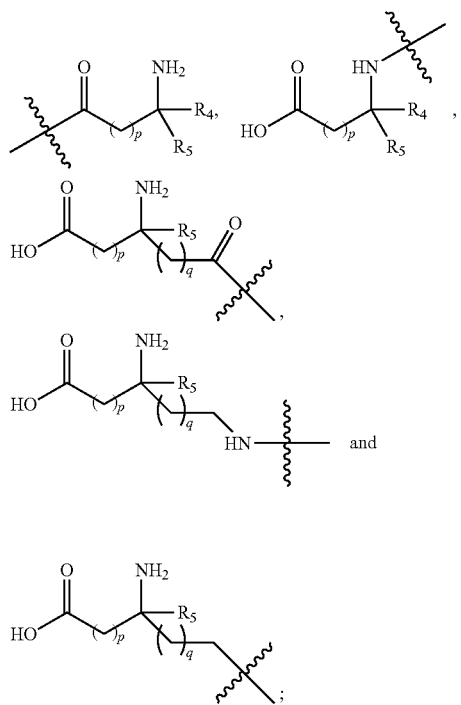

wherein;

$R_4$ is selected from the group consisting of H and $C_{1-6}$ alkyl, wherein the alkyl is optionally substituted with 1, 2 or 3 groups selected from the group consisting of $OR_x$, $NR_xR_y$ and $COOR_x$;

$R_5$ is selected from the group consisting of H and $C_{1-6}$ alkyl;

each $R_x$ and $R_y$, at each occurrence, is independently selected from the group consisting of H and $C_{1-6}$ alkyl;

p is 0 or 1;
q is 0, 1, 2, 3 or 4;
m is 1, 2, 3, 4 or 5;
n is 0, 1, 2, 3, 4 or 5.

In another aspect, provided is a compound of formula (I) or a pharmaceutically acceptable salt, ester, stereoisomer, tautomer, polymorph, solvate, isotopically labeled compound, metabolite or prodrug thereof, wherein the pharmaceutically acceptable salt is an acid addition salt, and the acid forming the acid addition salt is selected from the group consisting of formic acid, acetic acid, trifluoroacetic acid, hexane diacid, aspartic acid, benzoic acid, benzenesulfonic acid, carbonic acid, sulfuric acid, boric acid, camphorsulfonic acid, citric acid, cyclamic acid, ethanedisulfonic acid, ethanesulfonic acid, fumaric acid, glucoheptonic acid, gluconic acid, glucuronic acid, hexafluorophosphoric acid, hydrobromic acid, hydroiodic acid, isethionic acid, lactic acid, malic acid, maleic acid, malonic acid, methanesulfonic acid, methylsulfuric acid, naphthoic acid, 2-naphthalenesulfonic acid, nicotinic acid, nitric acid, orotic acid, oxalic acid, palmitic acid, pamoic acid, phosphoric acid, pyroglutamic acid, aldaric acid, stearic acid, succinic acid, tannic acid, tartaric acid and toluenesulfonic acid; preferably, the acid forming the acid addition salt is selected from the group consisting of formic acid, acetic acid and trifluoroacetic acid.

In another aspect, provided is a process for preparation of a compound of formula (I) or a pharmaceutically acceptable salt thereof, comprising the following steps:

(1) Preparation of intermediate E:

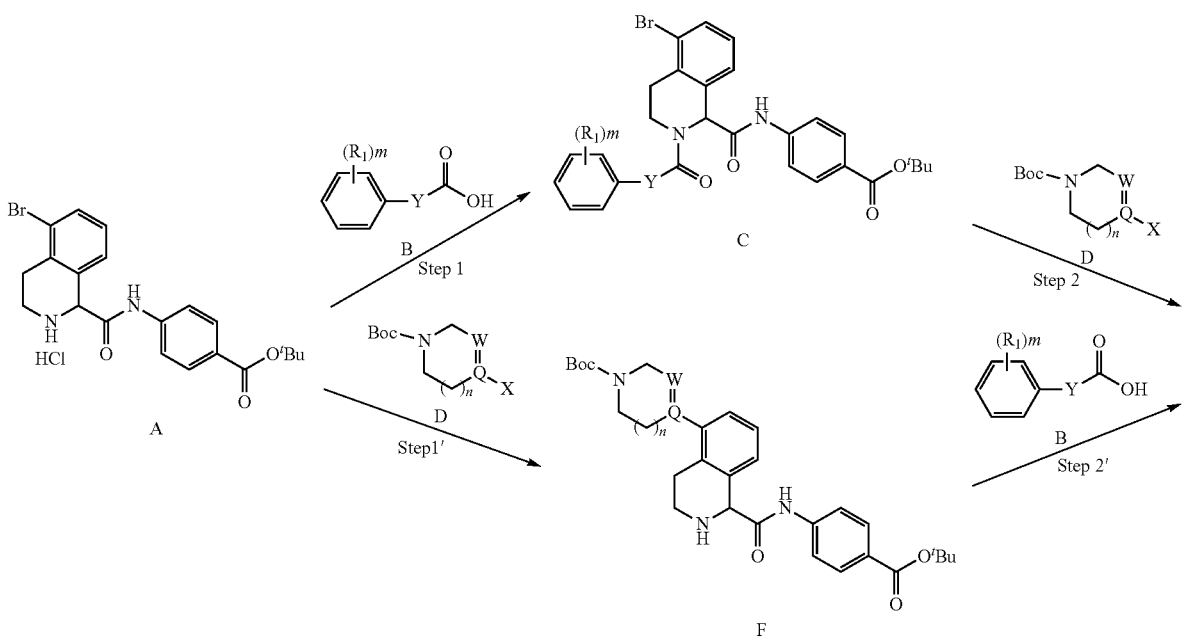

-continued

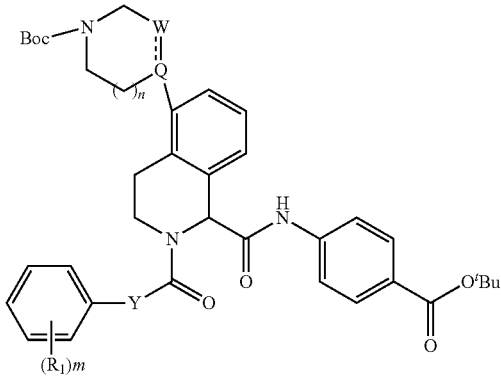

E wherein, X is hydrogen, boric acid or boronic ester group, preferably —B(OH)₂ or

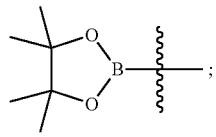 [SMILES: *B1OC(C)(C)C(C)(C)O1]

----, R₁, Y, W, Q, n and m are as defined above;

Route 1:

Step 1: reacting compound A with compound B through condensation reaction to obtain compound C;

Step 2: reacting compound C with compound D through coupling reaction to obtain compound E;

Route 2:

Step 1': reacting compound A with compound D through coupling reaction to obtain compound F;

Step 2': reacting compound F with a compound B through condensation reaction to obtain compound E;

(2) Preparation of a compound of formula (I) or a pharmaceutically acceptable salt thereof:

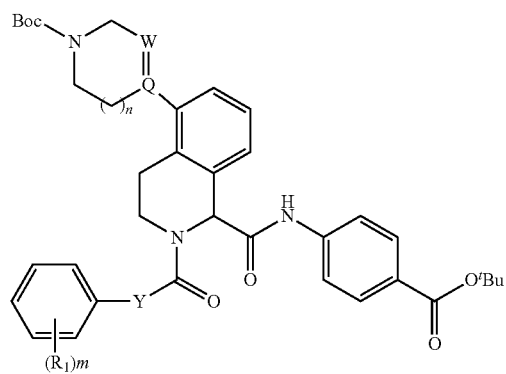

E

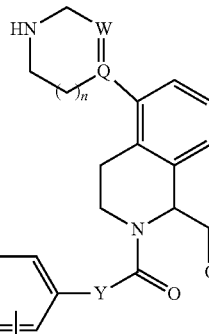

-continued

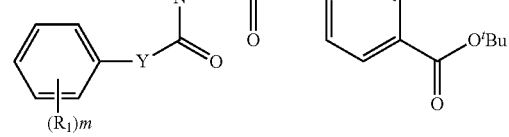

F

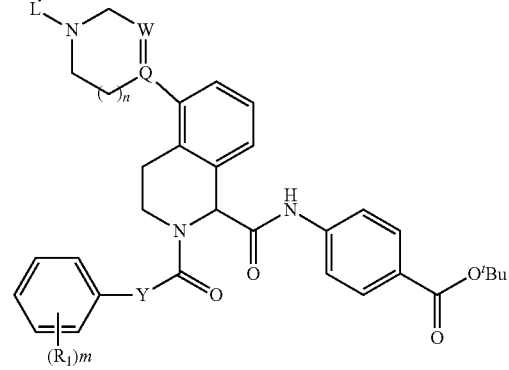

G

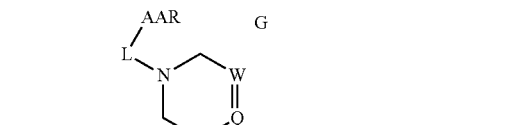

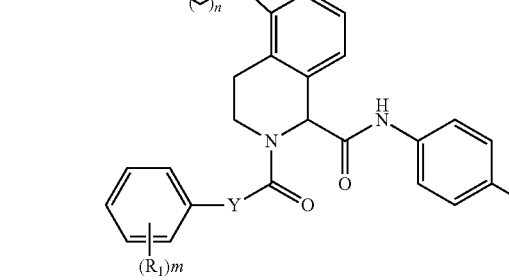

I wherein, ═══, $R_1$, L, AAR, Y, W, Q, n and m are as defined above;

Step 3: deprotecting compound E under acidic conditions to obtain compound F;

Step 4: reacting compound F with a carboxylic acid, a carboxylic acid derivative or a halohydrocarbon to connect with a -L-AAR group, then obtaining compound G;

Step 5: deprotecting compound G under acidic conditions, purifying and optionally generating the free form and/or generating the salt form, then obtaining a compound of formula (I) or a pharmaceutically acceptable salt thereof.

In another aspect, provided is a pharmaceutical composition comprising the compound of the present disclosure, or the pharmaceutically acceptable salt, ester, stereoisomer, tautomer, polymorph, solvate, isotopically labeled compound, metabolite or prodrug thereof or a mixture thereof, and one or more pharmaceutically acceptable carriers.

In yet another aspect, provided is use of the compound of the present disclosure or the pharmaceutically acceptable salt, ester, stereoisomer, tautomer, polymorph, solvate, isotopically labeled compound, metabolite or prodrug thereof, or a pharmaceutical composition of the present disclosure in the preparation of a medicament for treating a coagulation factor XIa inhibition associated disease.

In a further aspect, provided is the compound of the disclosure or a pharmaceutically acceptable salt, ester, stereoisomer, tautomer, polymorph, solvate, isotopically labeled compound, metabolite or prodrug thereof, or a pharmaceutical composition of the present disclosure for use in the treatment in a coagulation factor XIa inhibition associated disease.

In yet another aspect, provided is a method for treating a coagulation factor XIa inhibition associated disease, comprising administering to a subject in need thereof the compound of the present disclosure, or the pharmaceutically acceptable salt, ester, stereoisomer, tautomer, polymorph, solvate, isotopically labeled compound, metabolite or prodrug thereof, or a pharmaceutical composition of the present disclosure.

In one embodiment, the coagulation factor XIa inhibition associated disease is thromboembolic disorder, which includes arterial cardiovascular thromboembolic disorder, venous cardiovascular thromboembolic disorder, and thromboembolic disorder of the heart chamber.

Provided is further a pharmaceutical combination, which includes: (1) the compound of the present disclosure or the pharmaceutically acceptable salt, ester, stereoisomer, tautomer, polymorph, solvate, isotopically labeled compound, metabolite or prodrug thereof, or a pharmaceutical composition of the present disclosure; and (2): an additional active ingredient in combination with the ingredients described in (1). In one embodiment, the pharmaceutical combination is in the form of a pharmaceutical composition or a kit.

DETAILED DESCRIPTION

The technical content of the present disclosure is described below through specific embodiments, and those skilled in the art can easily understand other advantages and effects of the present disclosure from the disclosure of the present specification. The disclosure may also be embodied or applied by other different embodiments. Various modifications and changes can be made by those skilled in the art without departing from the scope of the disclosure.

Definitions

Unless otherwise defined below, all the technical and scientific terms used herein are intended to have the same meaning commonly understood by those skilled in the art. References to techniques used herein are intended to refer to techniques commonly understood in the art, including those variations or replacements of equivalent techniques that are obvious to those skilled in the art. While it is believed that the following terms are well understood by those skilled in the art, the following definitions are set forth for better explanation. When a trade name appears in this document, it is intended to refer to its corresponding commodity or its active ingredient. All patents, published patent applications and publications cited herein are hereby incorporated by reference.

The terms "including", "comprising", "having", "containing", or "relating to" and other variants thereof, as used herein, are inclusive or open-ended, and not exclusive of other elements or steps of methods that are not enumerated.

The term "halo" or "halogen" group is defined to include, F, Cl, Br or I.

The term "$C_{1-6}$ alkyl" refers to a linear or branched alkyl group having 1-6 carbon atoms, such as $C_{1-4}$ alkyl, $C_{2-6}$ alkyl, $C_{2-4}$ alkyl, $C_{3-6}$ alkyl, $C_{3-4}$ alkyl, $C_{1-2}$ alkyl, $C_1$ alkyl, $C_2$ alkyl, $C_3$ alkyl, $C_4$ alkyl, $C_5$ alkyl, or $C_6$ alkyl, preferably $C_{1-4}$ alkyl. Specific examples include, but not limited to, methyl, ethyl, propyl, isopropyl, n-butyl, isobutyl, sec-butyl, tert-butyl, n-pentyl, n-hexyl or the like.

The term "haloalkyl", as used herein, alone or in combination with other groups, refers to the alkyl group as defined above, wherein one or more hydrogen atoms are replaced by halogen. For example, the term "halo $C_{1-6}$ alkyl" refers to $C_{1-6}$ alkyl that optionally substituted with one or more (such as 1-3) halogen. Those skilled in the art should understand that, when halogen group is more than one, the halogens may be the same or different, and may be on the same or different carbon atoms. Specific examples include, but not limited to, $CH_2F$, $CHF_2$, $CF_3$, $CCl_3$, $C_2F_5$, $C_2Cl_5$, $CH_2CF_3$, $CH_2Cl$ or $CH_2CH_2CF_3$ or the like.

The term "$C_{1-4}$ alkylene" refers to a divalent alkyl group obtained by removing two hydrogen atoms from a linear or branched alkane which has 1-4 carbon atoms, for example $C_{1-3}$ alkylene, $C_{1-2}$ alkylene, $C_1$ alkylene, $C_2$ alkylene, $C_3$ alkylene, $C_4$ alkylene. Specific examples include, but not limited to, —$CH_2$—, —$CH_2CH_2$—, —$CH_2CH_2CH_2$—, —$CH(CH_3)CH_2$—, —$CH_2CH_2CH_2CH_2$—, —$CH(CH_3)CH_2CH_2$—, —$CH(CH_2CH_3)CH_2$—, —$C(CH_3)(CH_3)CH_2$—.

The term "5-6 membered heteroaryl" refers to a monocyclic aromatic group containing 5-6 ring members, wherein at least 1 and at most 4 (e.g. 1, 2, 3 or 4) of the ring members are heteroatoms selected from the group consisting of N, O and S. Examples include 5-membered heteroaryl group and 6-membered heteroaryl group. Specific examples include, but not limited to, furyl, thienyl, pyrrolyl, thiazolyl, isothiazolyl, thiadiazolyl, oxazolyl, isoxazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidinyl, pyridazinyl, pyrazinyl, 1,2,3-triazinyl, 1,3,5-triazinyl, 1,2,4,5-tetrazinyl, 1H-tetrazolyl or the like.

The term "amino acid residue" refers to a group formed by the removal of one hydrogen atom from the amino of the amino acid or the removal of one hydroxyl group from the carboxyl group of the amino acid. The amino acids of the present disclosure include natural occurring protein amino acids, stereoisomers and variants of natural protein amino acid, non-protein amino acids, post-translationally modified amino acids, enzymatically synthesized amino acids, derivatized amino acids, and constructs or structures designed to mimic amino acids. Specific examples include, but not limited to, glycine, alanine, valine, leucine, isoleucine, phenylalanine, tryptophan, tyrosine, aspartic acid, glutamic acid, lysine, glutamine, asparagine, serine, threonine, cysteine, proline, histidine, arginine, methionine.

The term "stereoisomer" refers to an isomer resulted from at least one asymmetric center. In a compound which have one or more (e.g. 1, 2, 3 or 4) asymmetric centers, it can produce a racemic mixture, a single enantiomer, a mixture of diastereomers and a single diastereomer. Specific individual molecules can also exist as geometric isomers (cis/trans). Similarly, the compound of the present disclosure may exist as a mixture of two or more rapidly equilibrating forms (commonly known as tautomers), wherein the rapidly equilibrating forms have different structures. Representative examples of tautomers include ketone-enol tautomers, phenol-ketone tautomers, nitroso-oxime tautomers, imine-enamine tautomers or the like. It is to be understood that, the scope of the present application covers all such isomers or mixture thereof in any ratio (e.g. 60%, 65%, 70%, 75%, 80%, 85%, 90%, 95%, 96%, 97%, 98%, 99%).

The chemical bond in the compound of the disclosure can be depicted herein with a solid line (———) solid wedge (◀━━), dashed wedge (⸳⸳⸳⫼⫼⫼⫼). A bond to an asymmetric carbon atom depicted with a solid line indicates that all possible stereoisomers at the carbon atom (e.g., specific enantiomers, racemic mixtures or the like) are contemplated. A bond to an asymmetric carbon atom depicted with a solid or dashed wedge indicates the existence of the stereoisomer that is shown. When present in a racemic mixture, a solid or dashed wedge is used to define relative stereochemistry rather than absolute stereochemistry. Unless otherwise indicated, it is intended that the compounds of the present disclosure can be present in the form of stereoisomers (including cis- and trans-isomers, optical isomers (e.g., R and S enantiomers), diastereomers, geometric isomers, rotamers, conformers, atropisomers, and mixtures thereof). The compounds of the present disclosure can exhibit one or more types of the above isomerism, and can be consisted of a mixture thereof (e.g., a racemic mixture and a diastereomeric pair).

All possible crystal forms or polymorphs of the compounds of the present disclosure are encompassed, which may be a single polymorph or a mixture of more than one polymorph in any ratio.

It will also be understood that for treatment, certain compounds of the present disclosure can exist in the free form, or where appropriate, in the form of a pharmaceutically acceptable derivative thereof. In the present disclosure, pharmaceutically acceptable derivatives include, but not limited to, pharmaceutically acceptable salts, esters, solvates, metabolites, isotopically labeled compounds or prodrugs, which can provide the compounds of the present disclosure or a metabolite or residue thereof directly or indirectly after administered to a patient in need thereof. Thus, when reference is made herein to "the compound of the disclosure," it is also intended to encompass the various derivative forms of the compound described above.

The term "substituted" refers to that one or more (e.g. 1, 2, 3 or 4) hydrogens on the designated atom are replaced by a selected group, provided that the designated atom does not exceed its normal valency in the current circumstances, and the substitution forms a stable compound. The number of selected alternative group is permissible only if such combinations result in stable compounds.

If a substituent is described as "optionally substituted", the substituent may be (1) unsubstituted, or (2) substituted. If a carbon in a substituent is described as being optionally substituted by one or more substituents from a list of substituents, one or more hydrogens on the carbon may be replaced individually and/or together by optional substituent(s), wherein the optional substituent(s) is/are independently selected. If a nitrogen in a substituent is described as being optionally substituted by one or more substituents from a list of substituents, one or more hydrogens on the nitrogen may be each replaced by optional substituent(s), wherein the optional substituent(s) is/are independently selected.

If a substituent is described as "independently selected from", each substituent may be the same or different with another substituent (other substituents).

The term "one or more", as used herein, means one, or more than one, e.g. 2, 3, 4, 5 or 10, under reasonable conditions. Similarly, "at least one" may refer to e.g. 1, 2, 3, 4, 5, 6, 7, 8, 9, 10 or more.

Unless otherwise indicated, as used herein, a substituent can be attached at any suitable position thereof.

The present disclosure also includes all pharmaceutically acceptable isotopically labeled compounds, which are identical to the compounds of the disclosure except that one or more atoms are replaced by the atom(s) of the same atomic number but having atomic mass or mass number different from the atomic mass or mass number prevailing in nature. Examples of isotopes suitable for inclusion in the compounds of the present disclosure include (but not limited to) isotopes of hydrogen (e.g. deuterium (D, $^2$H)), tritium (T, $^3$H); isotopes of carbon (e.g. $^{11}$C, $^{13}$C and $^{14}$C); isotopes of chlorine (e.g. $^{36}$Cl); isotopes of fluorine (e.g. $^{18}$F); isotopes of iodine (e.g. $^{123}$I and $^{125}$I); isotopes of nitrogen (e.g. $^{13}$N and $^{15}$N); isotopes of oxygen (e.g. $^{15}$O, $^{17}$O and $^{18}$O); isotopes of phosphorus (e.g. $^{32}$P); and isotope of sulfur (e.g. $^{35}$S). Some isotopically labeled compounds of the present disclosure can be used in tissue distribution studies (e.g. assays) of drug and/or substrate. The pharmaceutically acceptable solvates of the present disclosure include those in which crystalline solvent can be isotopically substituted, e.g., $D_2O$, acetone-$d_6$ or DMSO-$d_6$.

In addition, groups that are not defined herein may conform to the common definitions in the art.

A pharmaceutically acceptable salt of the compound of the present disclosure includes acid addition salts and base addition salts. Examples include salts formed by alkali metals, alkaline earth metals, ammonium, alkylammonium, or the like, salts formed by inorganic or organic acids. Examples of such salts include formates or the like.

The term "ester", as used herein, refers to an ester derived from a compound of any general formula of the disclosure, which includes a physiologically hydrolyzable ester (which can be hydrolyzed under physiological conditions to release the compound of the disclosure in the form of a free acid or alcohol). The compound of the present disclosure per se can also be an ester.

The compound of the present disclosure can be present in the form of a solvate (preferably a hydrate) wherein the compound of the present disclosure contains a polar solvent, particularly e.g., water, methanol or ethanol, as a structural element of the crystal lattice of the compound. The polar solvent, particularly water, can be present in an amount of a stoichiometric or non-stoichiometric ratio.

Also included within the scope of the present disclosure are metabolites of the compound of the disclosure, i.e., substances formed in vivo upon administration of the compound of the disclosure. Such products can be generated, e.g., by the oxidation, reduction, hydrolysis, amidation, deamidation, esterification, delipidization, enzymatic hydrolysis or the like of the compound administered. Accordingly, the present disclosure contemplates metabolites of the compound of the present disclosure, including compounds prepared by contacting the compound of the present disclosure with a mammal for a time sufficient to produce a metabolite thereof.

Further included within the scope of the present disclosure are prodrugs of the compound of the present disclosure, which are certain derivatives of the compound of the present disclosure that have less or no pharmacological activity themselves but when administered into or onto the body, can be converted to the compound of the disclosure having the desired activity by, e.g., hydrolytic cleavage. Typically, such prodrugs will be functional group derivatives of the compound that are readily converted in vivo to the desired therapeutically active compound. Additional information on the use of prodrugs can be found in J. Rautio et al., Nature Reviews Drug Discovery (2008) 7, 255-270 and Prodrugs: Challenges and Rewards (V. Stella et al. ed., Springer, 2007).

The present disclosure also encompasses the compound of the present disclosure containing a protective group. In any process for preparing the compound of the present disclosure, it may be necessary and/or desirable to protect sensitive or reactive groups on any of a relevant molecule, thereby forming a chemically protected form of the compound of the present disclosure. This can be achieved by conventional protective groups, for example, those described in Protective Groups in Organic Synthesis (Greene et al, 4th Ed, Wiley-Interscience (2006)), the references are incorporated herein by reference. The protective groups can be removed at suitable subsequent stage using methods known in the art.

The term "room temperature" (abbreviated as RT), as used herein, refers to about 20-30° C., preferably about 25° C. "Low temperature" refers to the temperature of the reaction system which is lowered below the ambient temperature by means of cooling measures such as ice water bath, ice salt bath or the like.

Compounds

An object of the present disclosure is to provide a compound of formula (I) or a pharmaceutically acceptable salt, ester, stereoisomer, tautomer, polymorph, solvate, isotopically labeled compound, metabolite or prodrug thereof,

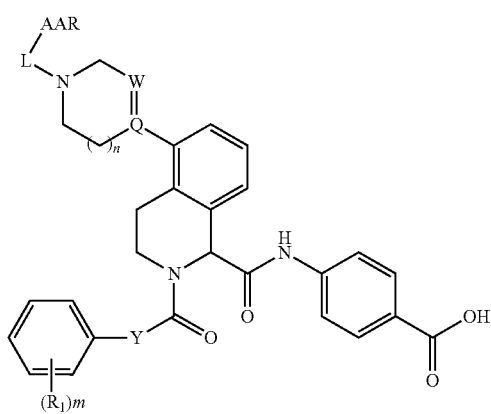

(I)

wherein:
" $=\!=\!=\!=$ " represents a single bond or a double bond;
each $R_1$, at each occurrence, is independently selected from the group consisting of halogen, halo $C_{1-6}$ alkyl, nitro, cyano and 5-6 membered heteroaryl;
Y is selected from the group consisting of

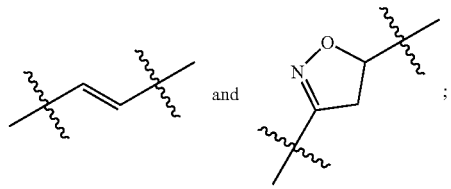

W is selected from the group consisting of $CR_2$, $CR_{2a}R_{2b}$ and $C(=O)$;
Q is selected from the group consisting of N, C and $CR_3$;
each $R_2$, $R_{2a}$, $R_{2b}$ and $R_3$ is independently selected from the group consisting of H and $C_{1-6}$ alkyl;
L is selected from the group consisting of chemical bond, $C_{1-4}$ alkylene and a bivalent radical formed by any combination of 1-4 groups selected from the group consisting of —$CH_2$—, —C(=O)— and —NH—;
AAR represents amino acid residue;
or
AAR is selected from the group consisting of

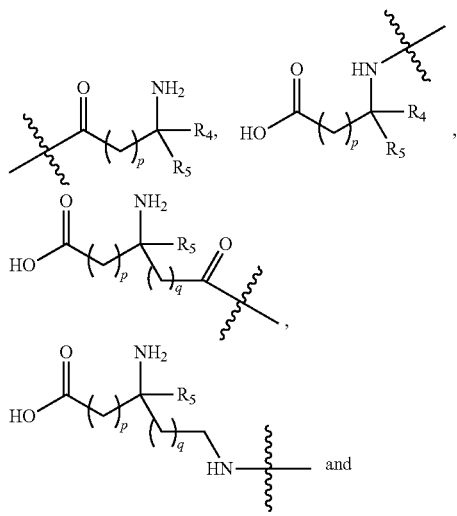

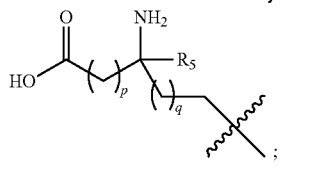

wherein
$R_4$ is selected from the group consisting of H, $C_{1-6}$ alkyl, wherein the alkyl is optionally substituted with 1, 2 or 3 groups selected from the group consisting of $OR_x$, NR—$R_y$ and $COOR_x$;
$R_5$ is selected from the group consisting of H and $C_{1-6}$ alkyl;
each $R_x$ and $R_y$, at each occurrence, is independently selected from the group consisting of H and $C_{1-6}$ alkyl;
p is 0 or 1;
q is 0, 1, 2, 3 or 4;

m is 1, 2, 3, 4 or 5;
n is 0, 1, 2, 3, 4 or 5.

In one embodiment, each $R_1$, at each occurrence, is independently selected from the group consisting of halogen, cyano and 5-6 membered heteroaryl. In a preferred embodiment, each $R_1$, at each occurrence, is independently selected from the group consisting of fluorine, chlorine, bromine, cyano and 5-membered heteroaryl. In a more preferred embodiment, each $R_1$, at each occurrence is independently selected from the group consisting of fluorine, chlorine, cyano and

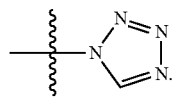

In one embodiment, W is selected from the group consisting of CH, $CH_2$ and C(=O). In another embodiment, Q is selected from the group consisting of C, CH and N.

In one embodiment, "=====" represents a single bond. In another embodiment, Q is selected from the group consisting of N and $CR_3$. In a preferred embodiment, Q is selected from the group consisting of N and CH. In a more preferred embodiment, Q is N. In a further embodiment, W is selected from the group consisting of $CR_{2a}R_{2b}$ and C(=O). In a preferred embodiment, W is selected from the group consisting of $CH_2$ and C(=O). In a more preferred embodiment, W is C(=O).

In one embodiment, "=====" represents a double bond. In another embodiment, Q is C. In a further embodiment, W is $CR_2$. In a preferred embodiment, W is CH.

In a preferred embodiment, "=====" represents a single bond, and Q is N. In another preferred embodiment, "=====" represents a double bond, and Q is C.

In a preferred embodiment, "=====" represents a single bond, and W is C(=O). In another preferred embodiment, "=====" represents a double bond, and W is CH.

In a more preferred embodiment, when "=====" represents a single bond, Q is N, W is C(=O); when "=====" represents a double bond, Q is C, W is CH.

In one embodiment, Y is selected from the group consisting of

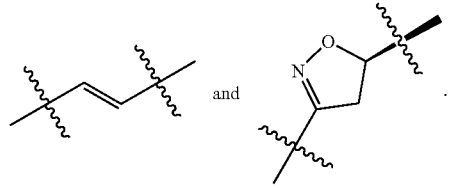

In one embodiment, Y is

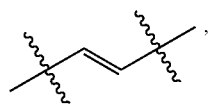 [SMILES: */C=C/*]

each $R_1$, at each occurrence, is independently selected from the group consisting of halogen and 5-membered heteroaryl; preferably, one $R_1$ is 5-membered heteroaryl, if m is not 1, other $R_1$, at each occurrence, is each independently selected from the group consisting of halogen; more preferably, one $R_1$ is

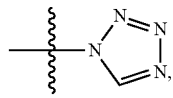 [SMILES: *n1cnnn1]

if m is not 1, other $R_1$, at each occurrence, is each independently selected from the group consisting of fluorine and chlorine.

In one embodiment, Y is

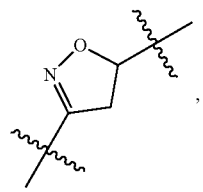 [SMILES: *C1=NOC(*)C1]

each $R_1$, at each occurrence, is independently selected from the group consisting of halogen; preferably, each $R_1$, at each occurrence, is independently selected from the group consisting of fluorine and chlorine.

In one embodiment, L is selected from the group consisting of chemical bond and $C_{1-4}$ alkylene. In another embodiment, L is selected from the group consisting of chemical bond and a bivalent radical formed by any combination of 1-4 groups selected from the group consisting of —$CH_2$—, —C(=O)— and —NH—. In one embodiment, L is chemical bond, AAR is directly attached to N atom. In another embodiment, L is a bivalent radical formed by any combination of 1-4, e.g. 1, 2, 3 or 4 groups selected from the group consisting of —$CH_2$—, —C(=O)— and —NH—. In a preferred embodiment, L is a bivalent radical formed by any combination of 1-4 groups selected from the group consisting of —$CH_2$— and —C(=O)—. In one embodiment, L is selected from the group consisting of chemical bond, methylene, ethylene, —$CH_2$—NH—, —NH—C(=O)— and —C(=O)—$CH_2$—. In a preferred embodiment, L is selected from the group consisting of chemical bond, ethylene and —C(=O)—$CH_2$—. In a more preferred embodiment, L is selected from the group consisting of chemical bond and —C(=O)—$CH_2$—.

In one embodiment, AAR represents amino acid residue. In preferred embodiments, AAR is selected from the group consisting of natural amino acid residues. In a more preferred embodiment, the amino acid is selected from the group consisting of glycine, alanine, valine, leucine, isoleucine, phenylalanine, tryptophan, tyrosine, aspartic acid, glutamic acid, lysine, glutamine, asparagine, serine, threonine, cysteine, proline, histidine, arginine and methionine. In further preferred embodiments, the amino acid is selected from the group consisting of glycine, alanine, valine, leucine, isoleucine, aspartic acid, glutamic acid, lysine, serine, threonine. In a more preferred embodiment, the amino acid is selected from the group consisting of glycine, alanine, valine, leucine, isoleucine, aspartic acid, glutamic acid and lysine. In a particularly preferred embodiment, the amino acid is selected from the group consisting of alanine, valine, glutamic acid and lysine.

In another embodiment, AAR is selected from the group consisting of

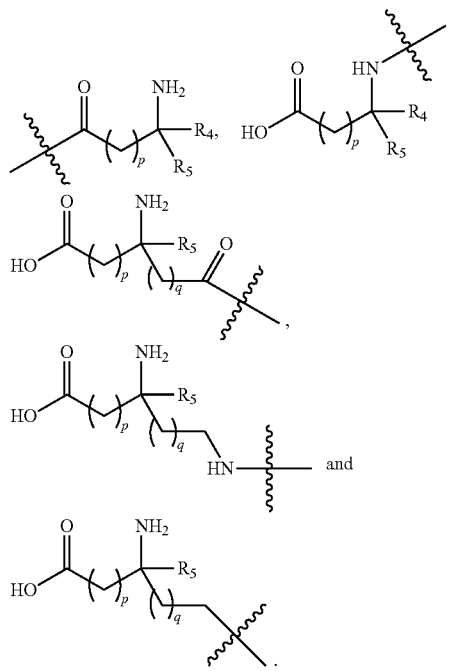

In a preferred embodiment, AAR is selected from the group consisting of

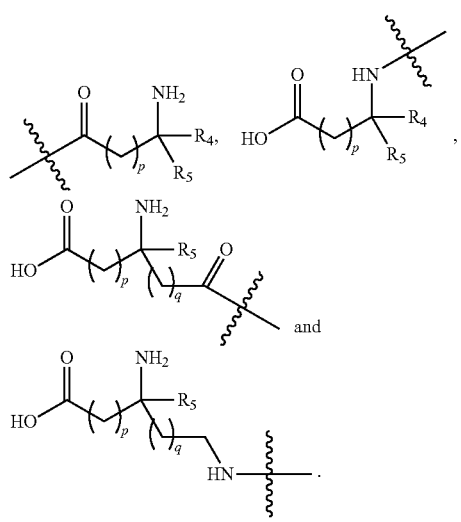

In one embodiment, p is 0, and $R_4$ is $C_{3-6}$ alkyl, preferably $C_{3-4}$ alkyl, wherein the alkyl is optionally substituted with 1 or 2 groups selected from the group consisting of OH, $NH_2$ and COOH; or $R_4$ is —$CH_2CH_2COOH$;

$R_5$ is H;

q is 2, 3 or 4.

In another embodiment, p is 1 and $R_4$ is $C_{2-6}$ alkyl, preferably $C_{2-4}$ alkyl, wherein the alkyl is optionally substituted with 1 or 2 groups selected from the group consisting of OH, $NH_2$ and COOH; or $R_4$ is —$CH_2COOH$; $R_5$ is H;

q is 1, 2, 3 or 4.

In one embodiment, $R_5$ is selected from the group consisting of H and $C_{1-3}$ alkyl. In a preferred embodiment, $R_5$ is H.

In one embodiment, p is 0.

In one embodiment, AAR is selected from the group consisting of:

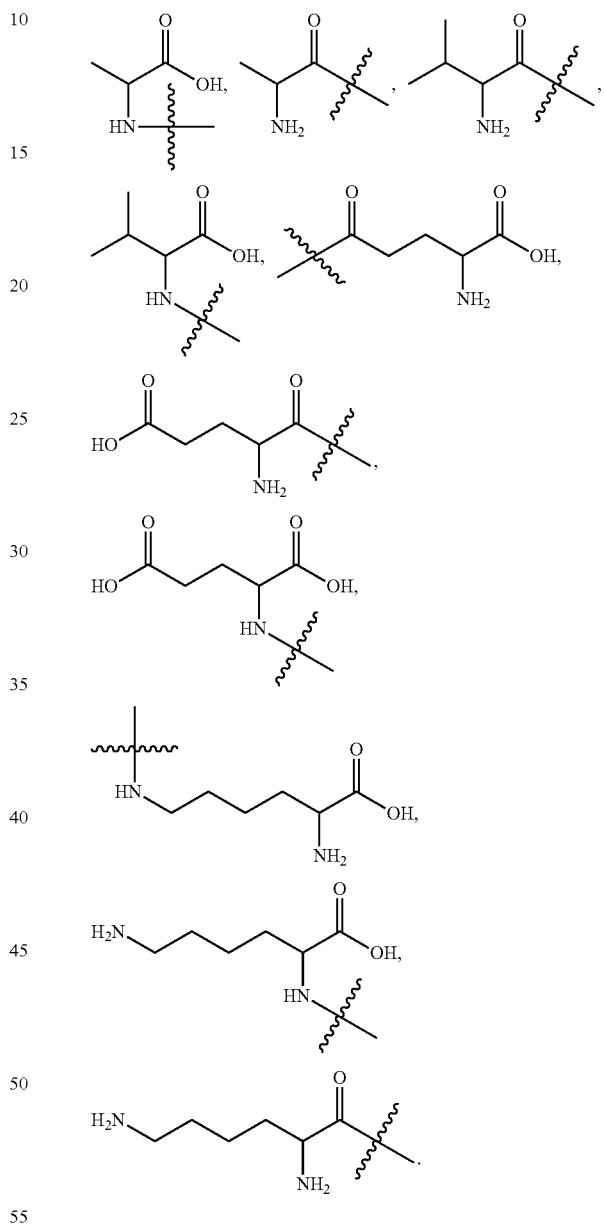

In a preferred embodiment, AAR is selected from the group consisting of:

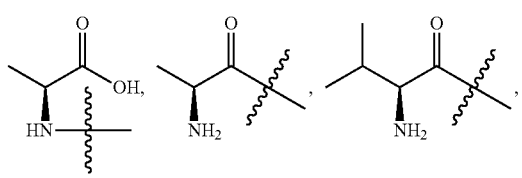

-continued
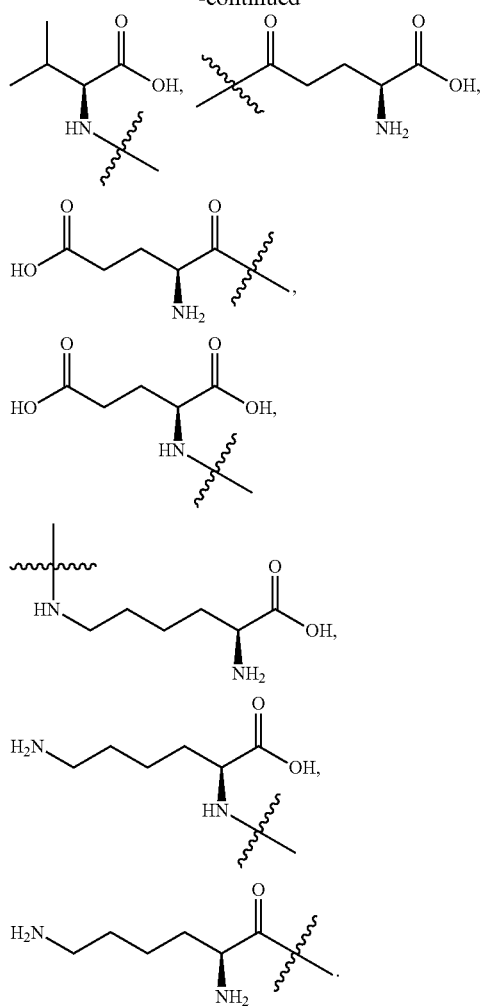
In a particularly preferred embodiment, AAR is selected from the group consisting of:
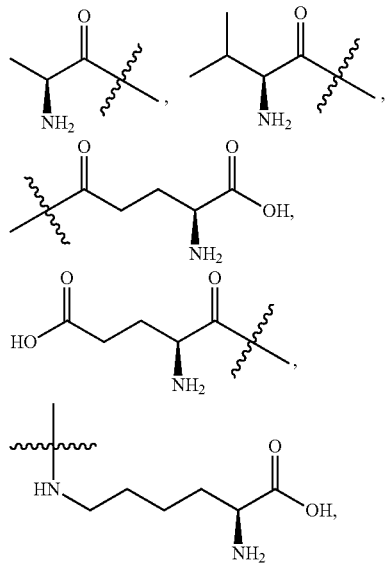
-continued
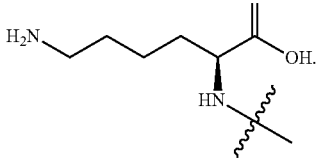
In a further embodiment, -L-AAR is selected from the group consisting of:
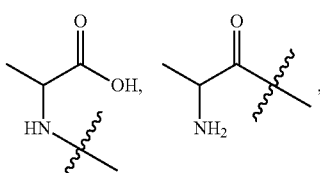
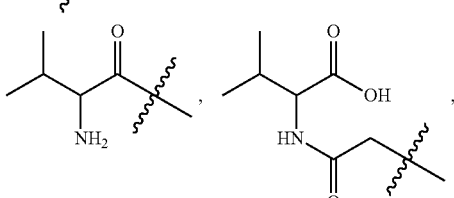
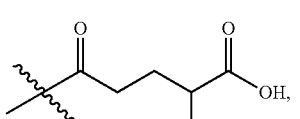
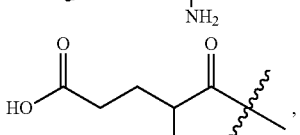
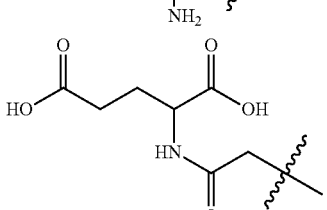
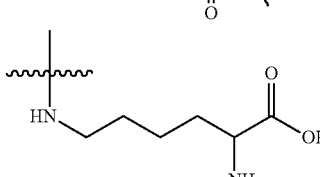
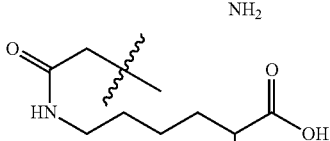
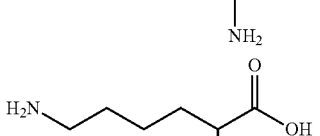

-continued

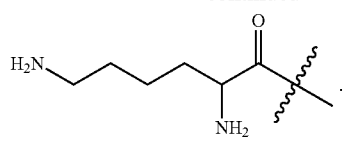

In a preferred embodiment, -L-AAR is selected from the group consisting of:

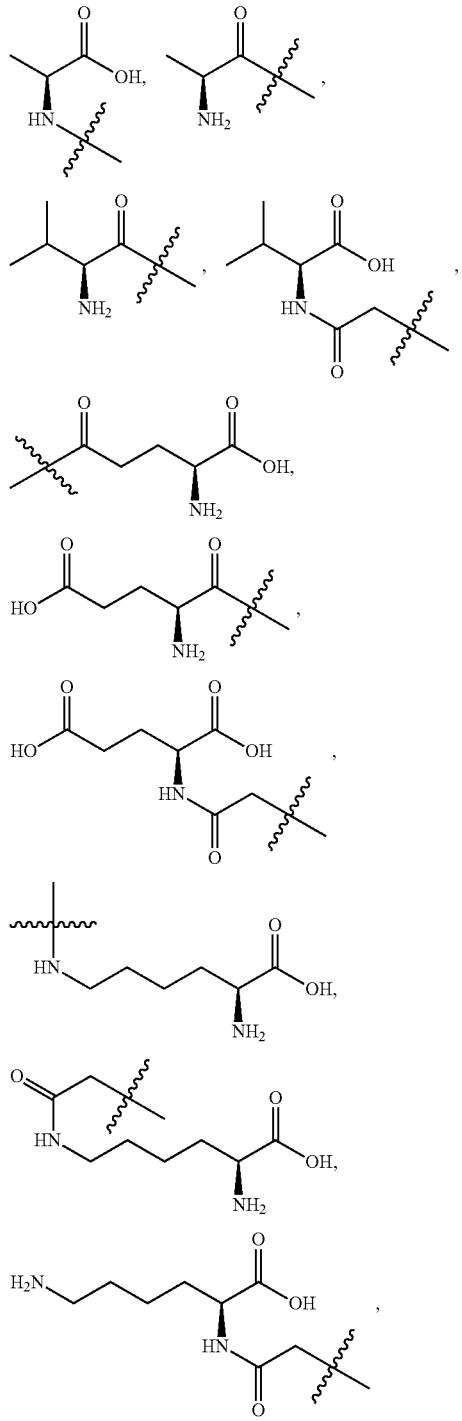

-continued

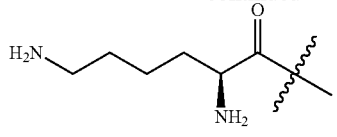

In a particularly preferred embodiment, -L-AAR is selected from the group consisting of:

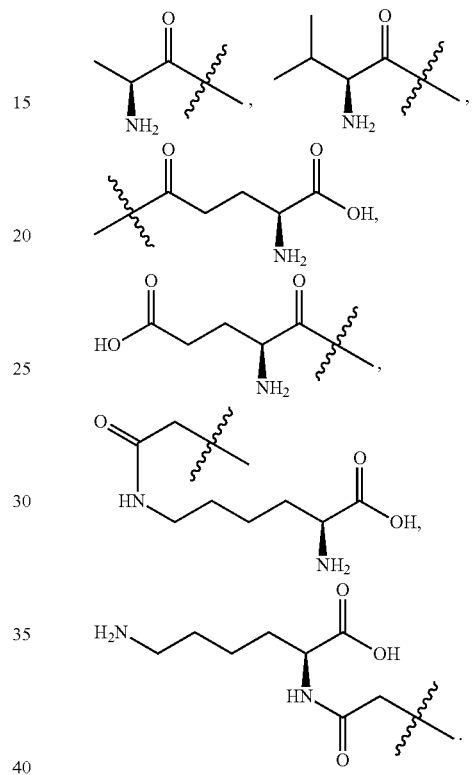

In one embodiment, n is 0, 1, 2. In a preferred embodiment, n is 1.

In one embodiment, m is 2, 3, 4 or 5. In a preferred embodiment, m is 2 or 3.

In a preferred embodiment, the compound of the present disclosure has the structure of formula (II):

(II)

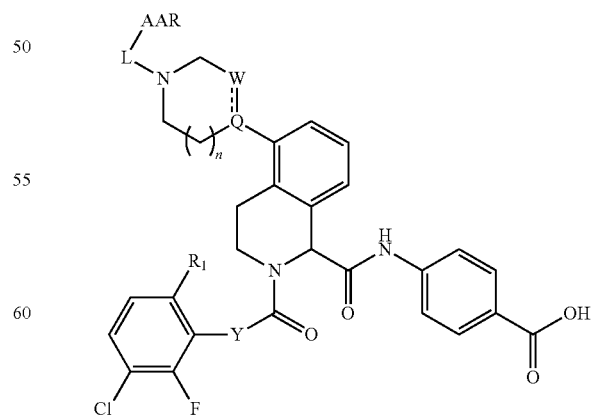

wherein, ====, $R_1$, Y, W, Q, L, AAR and n are as defined above.

In preferred embodiments, the compound of the present disclosure has the structure of formula (III):

(III)

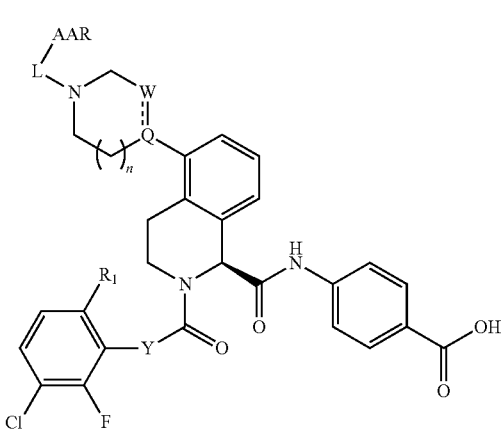

wherein, ═══, $R_1$, Y, W, Q, L, AAR and n are as defined above.

In preferred embodiments, the compound of the present disclosure has the structure of formula (IVa) or formula (IVb):

(IVa)

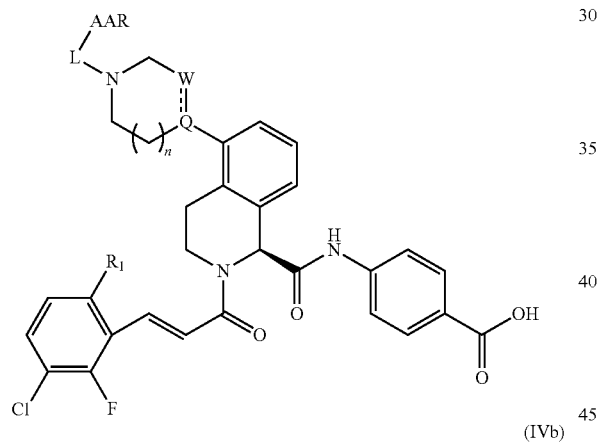

(IVb)

wherein, ═══, $R_1$, W, Q, L, AAR and n are as defined above.

The present disclosure encompasses a compound obtained by any combination of each embodiment. In preferred embodiments, provided is a compound or a pharmaceutically acceptable salt, ester, stereoisomer, tautomer, polymorph, solvate, isotopically labeled compound, metabolite or prodrug thereof, wherein the compound is selected from:

1-a

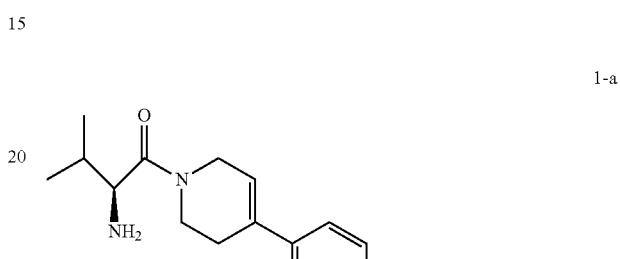

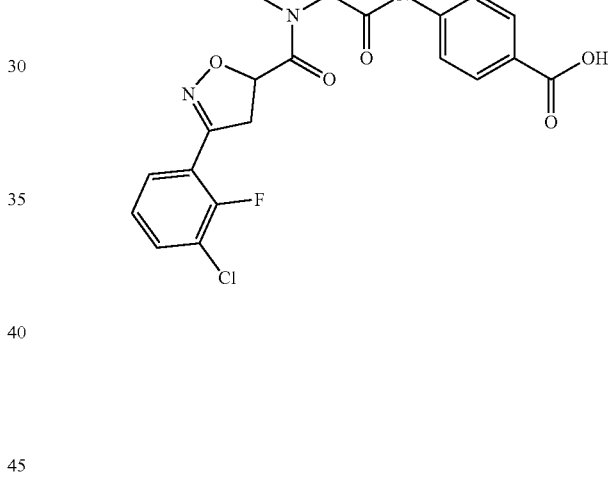

2-a

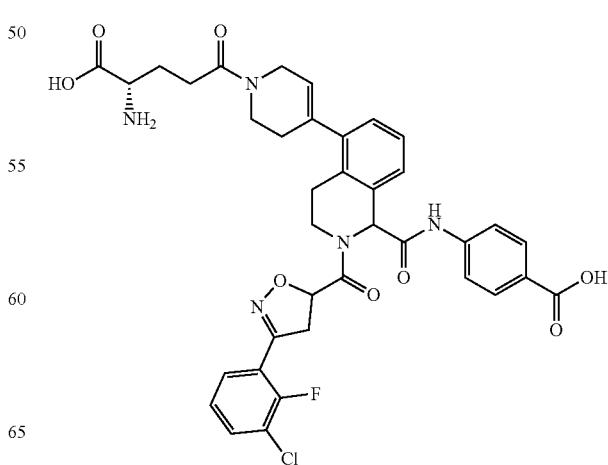

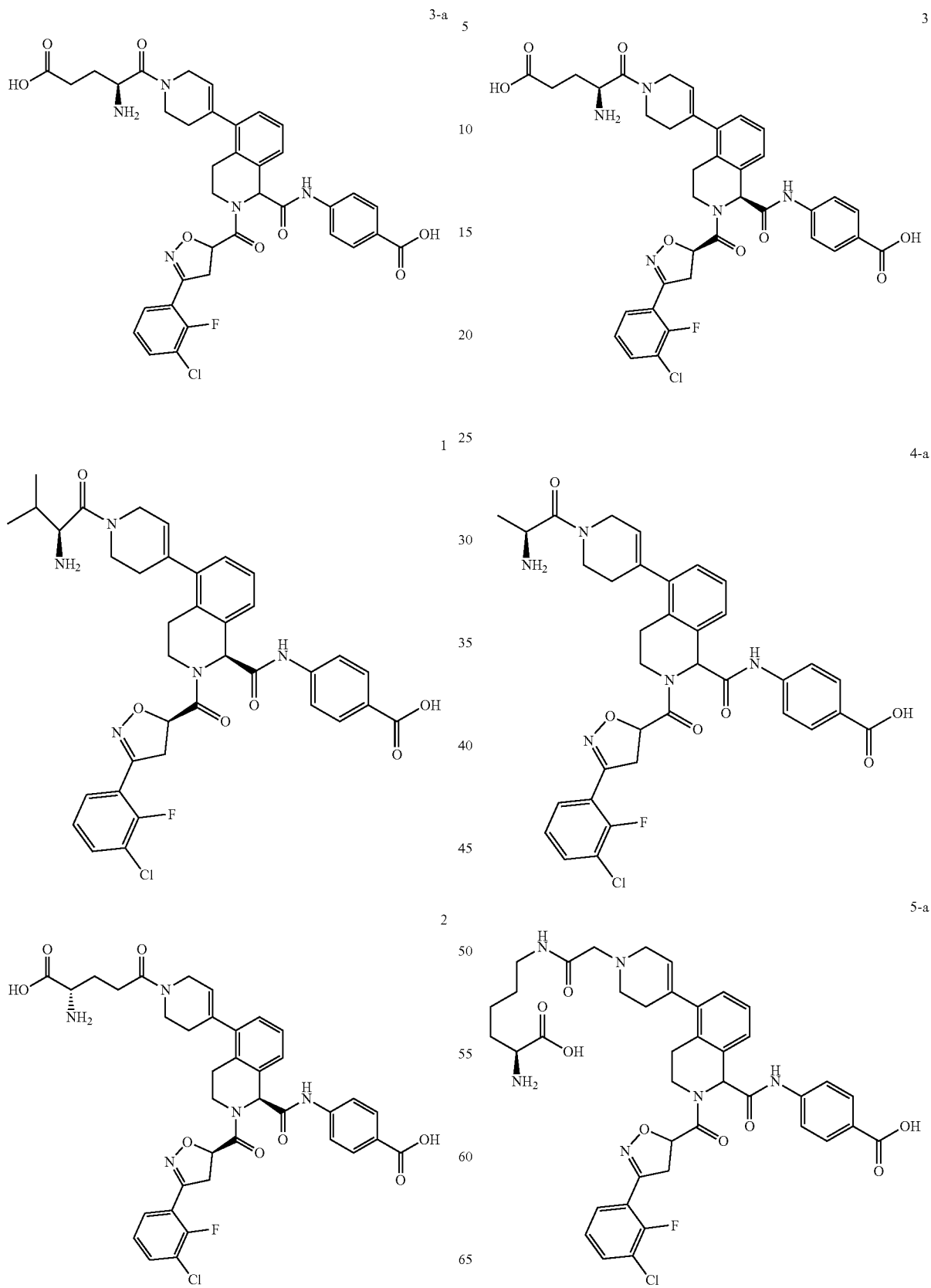

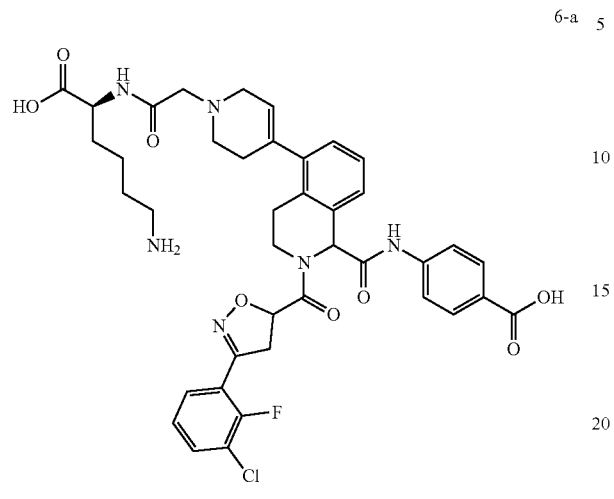
6-a
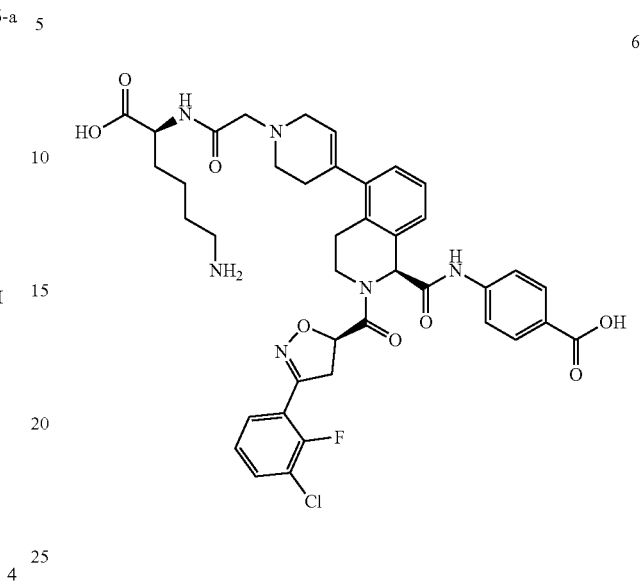
6
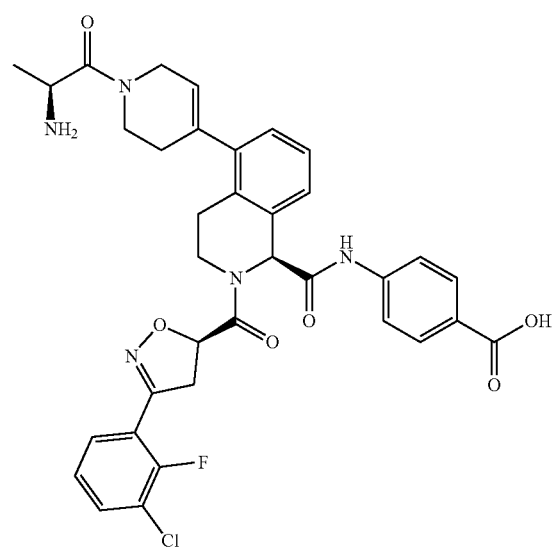
4
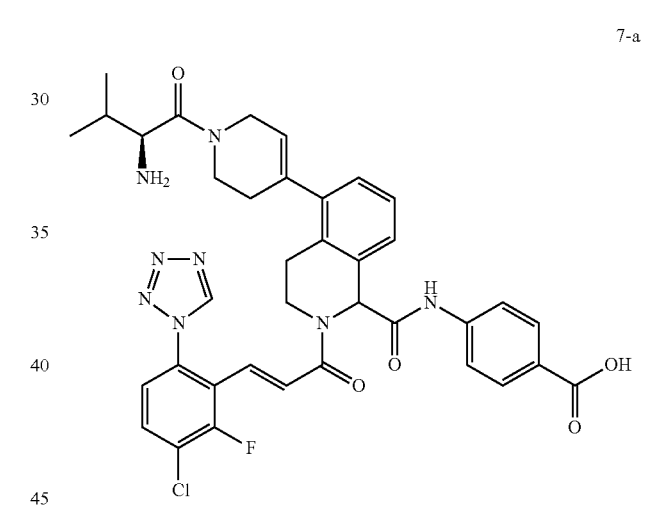
7-a
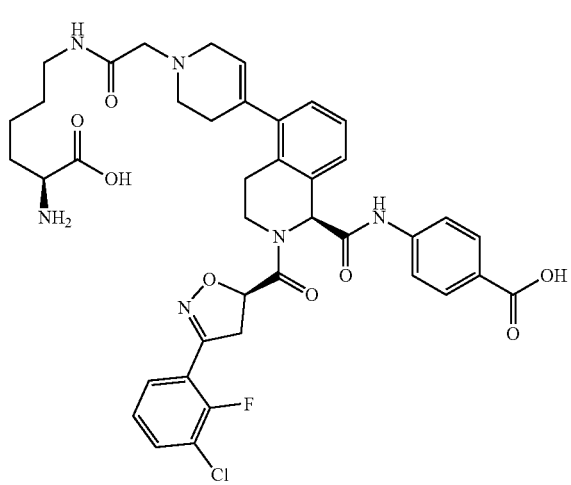
5
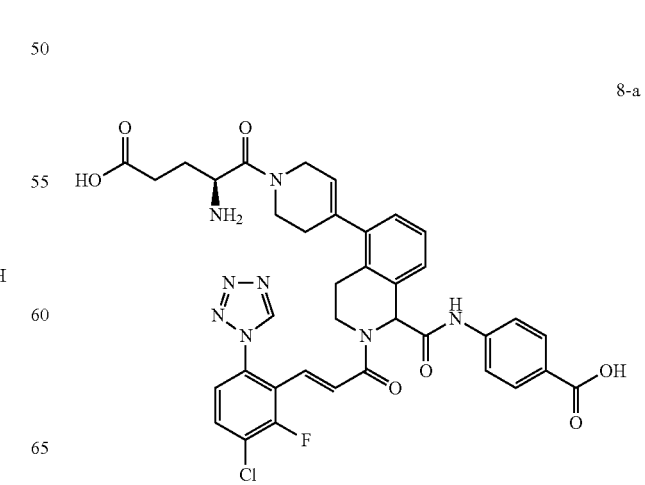
8-a 9-a
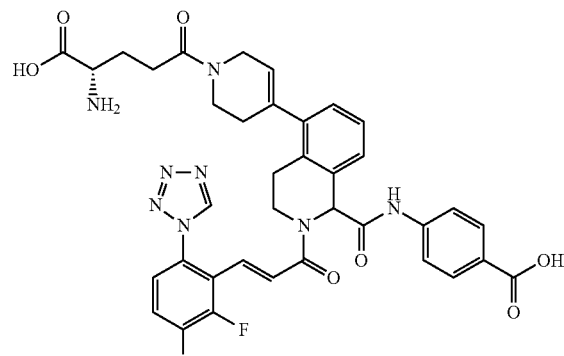
8
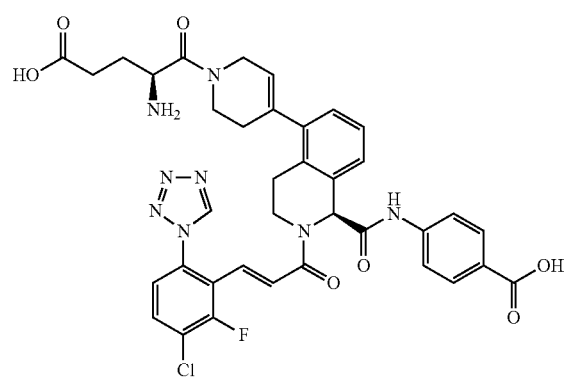
9
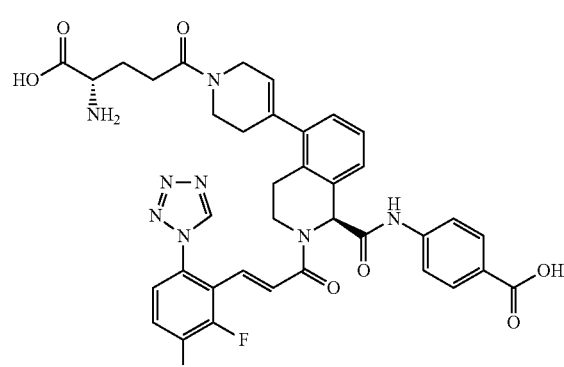
10-a
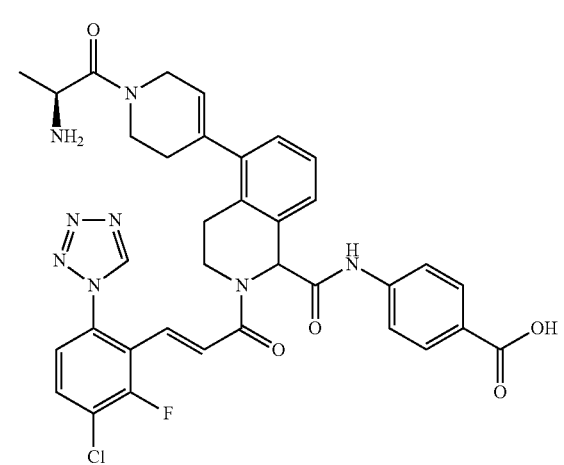
11-a
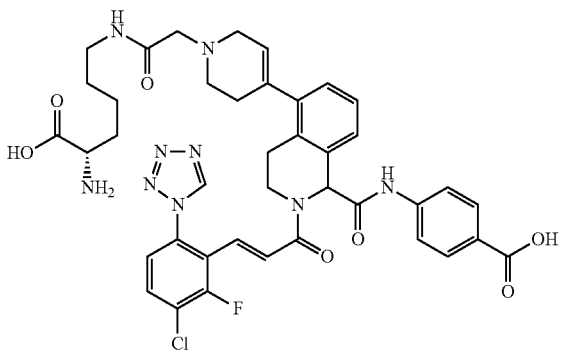
12-a
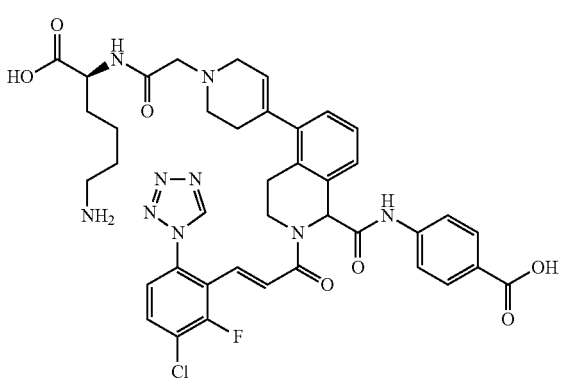
11
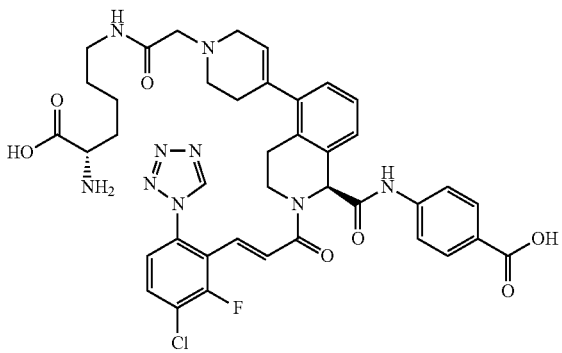
12
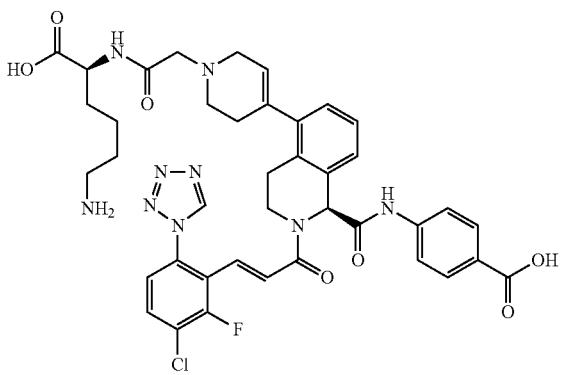

13-a
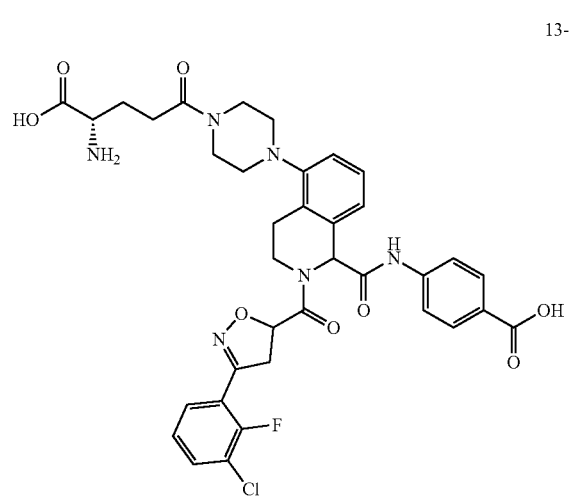
13
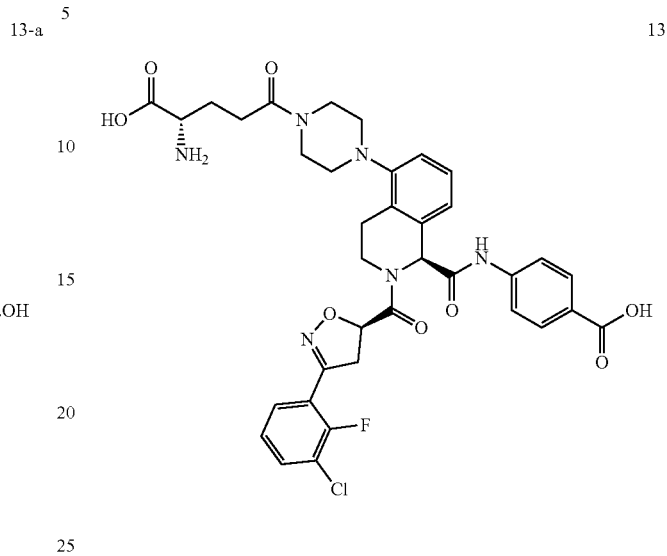
14-a
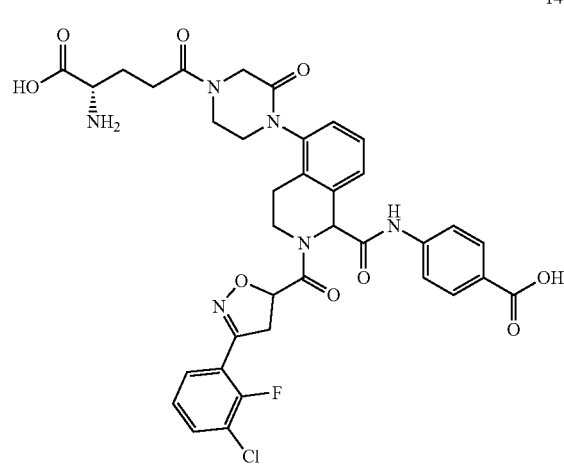
14
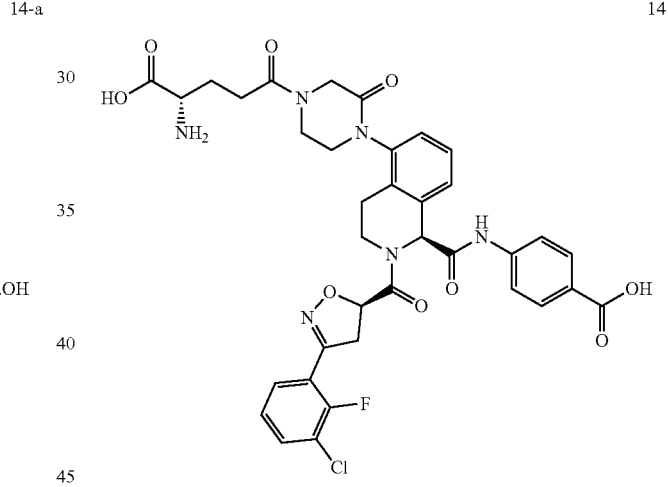
15-a
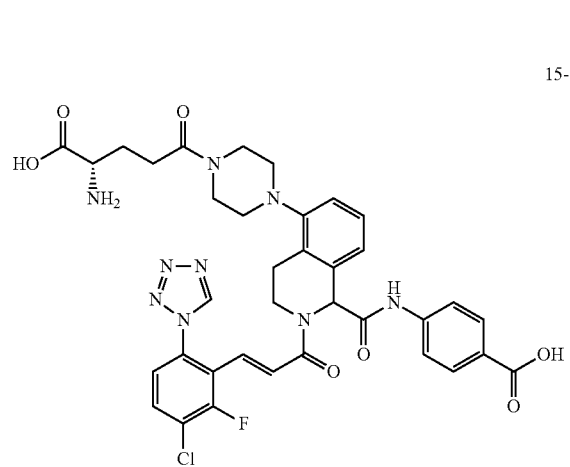
15
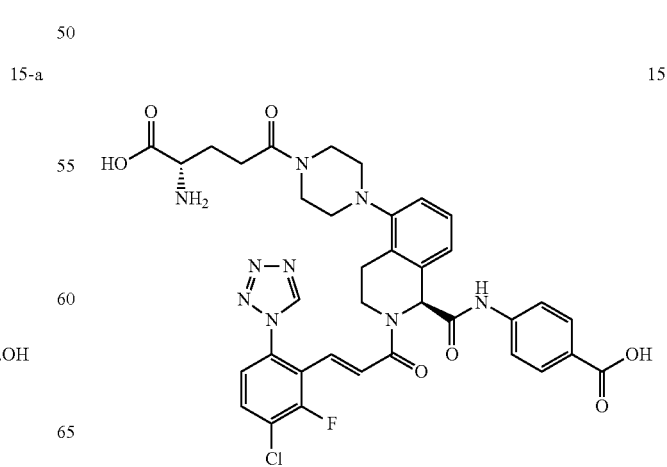

-continued
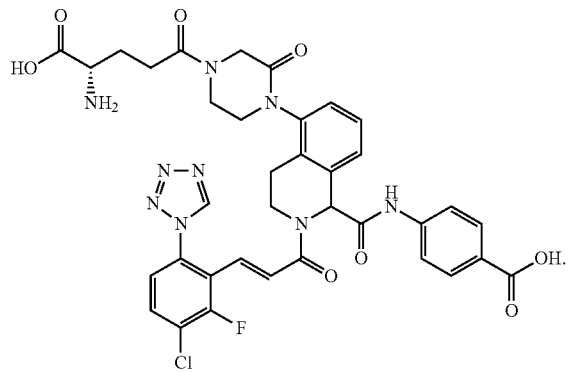
16-a
In preferred embodiments, provided is a compound or a pharmaceutically acceptable salt, ester, stereoisomer, tautomer, polymorph, solvate, isotopically labeled compound, metabolite or prodrug thereof, wherein the compound is selected from:
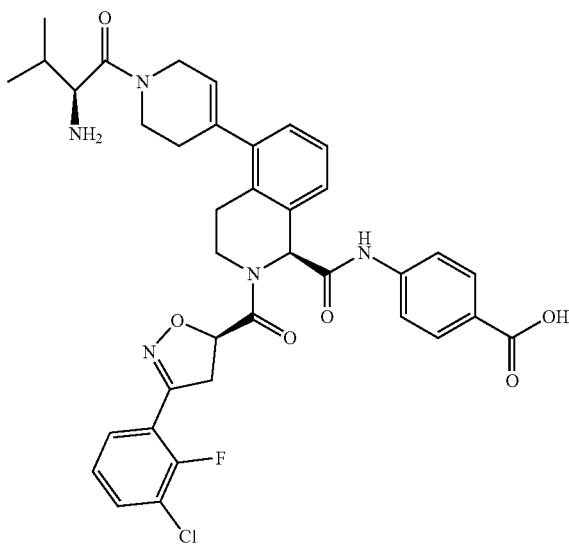
1
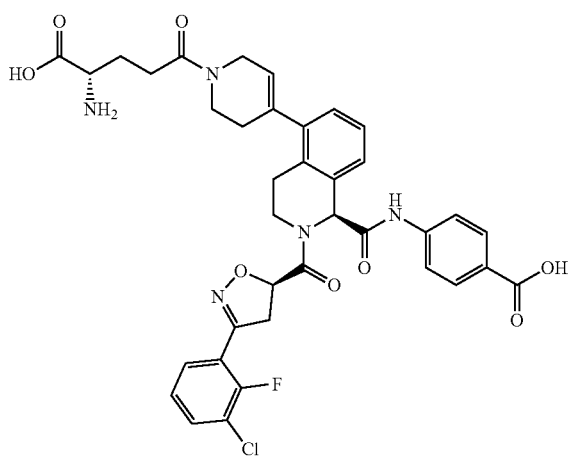
2
-continued
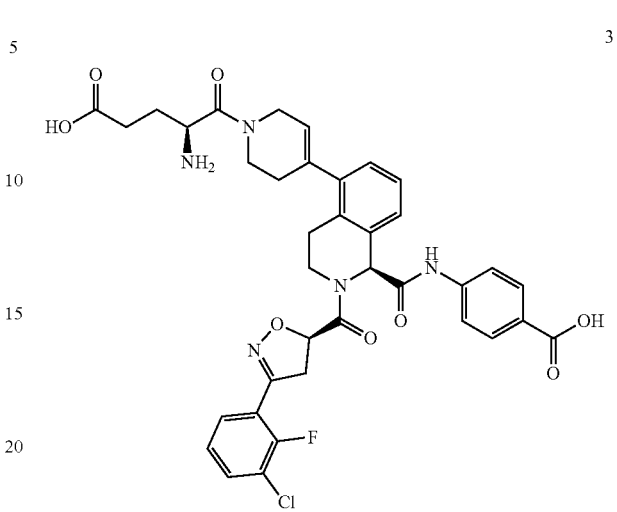
3
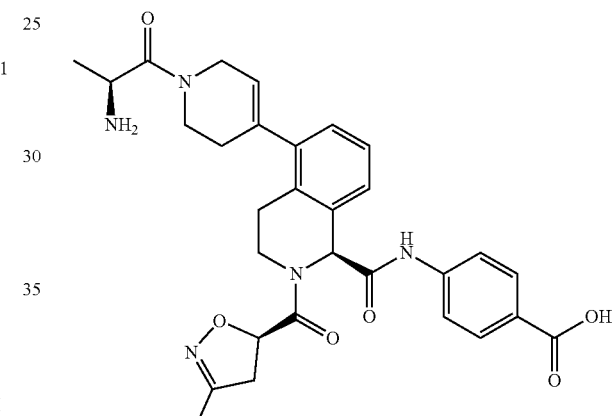
4
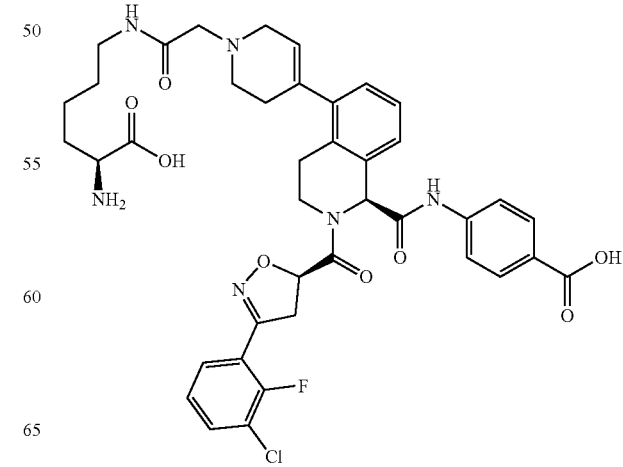
5

6
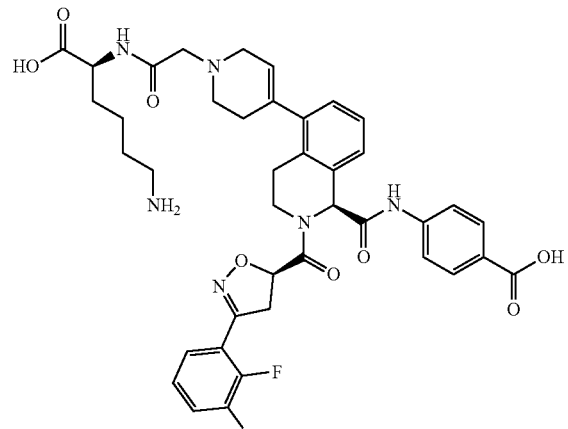
7-a
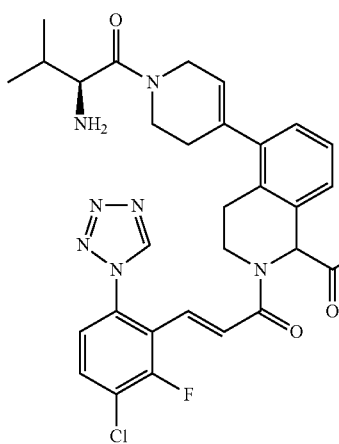
8
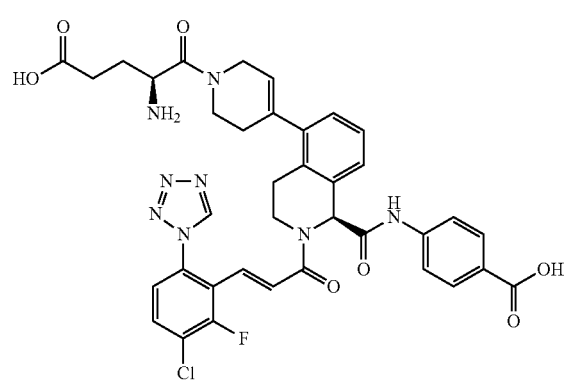
9
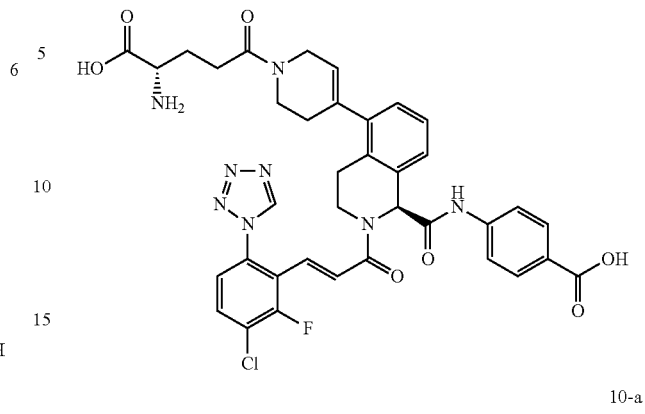
10-a
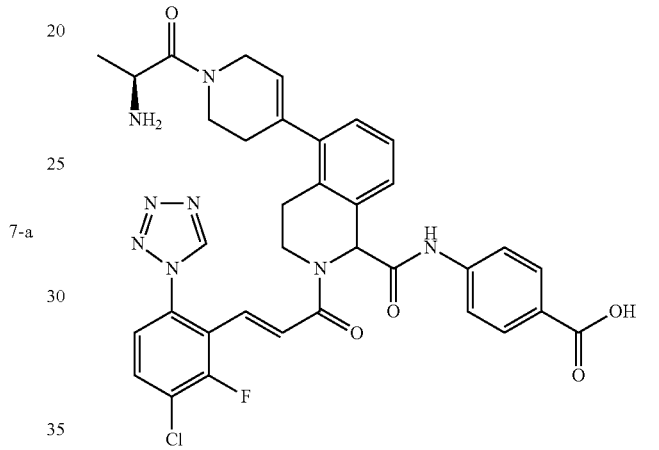
11
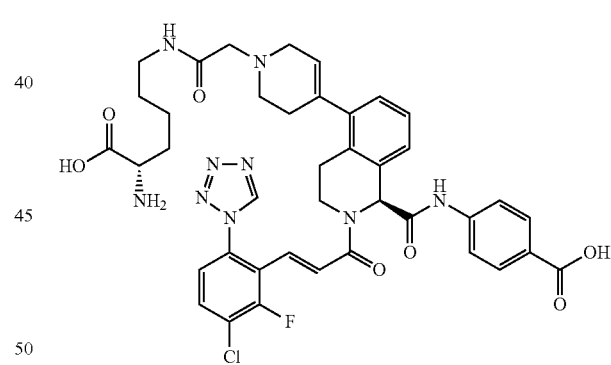
12
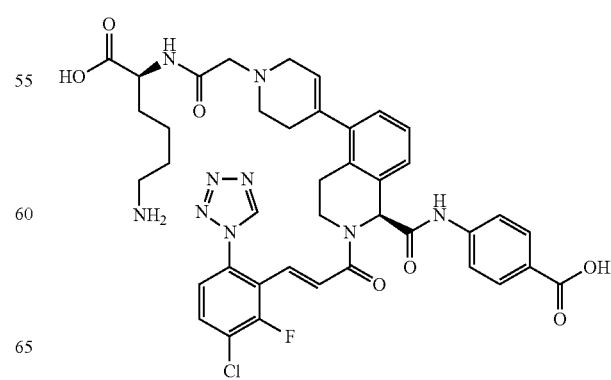

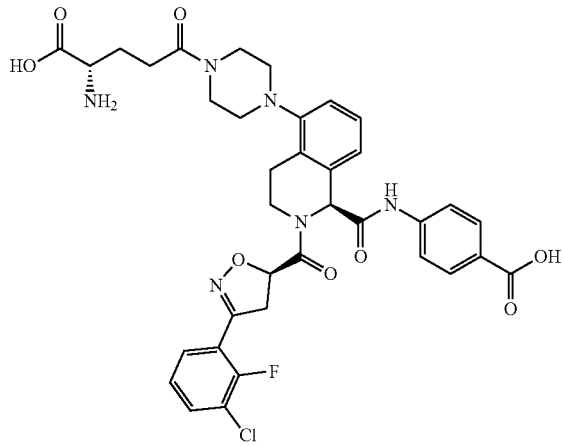

13

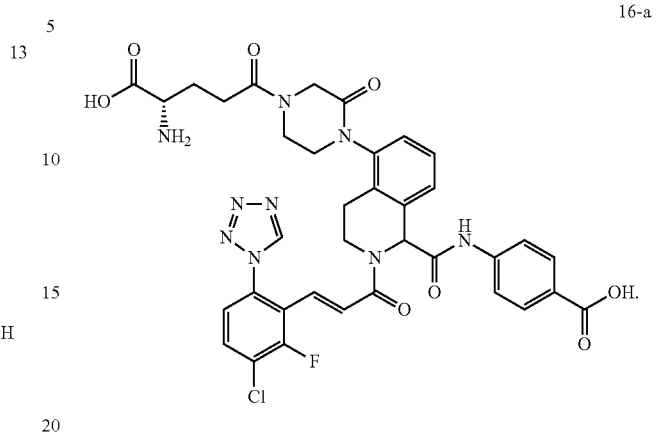

5

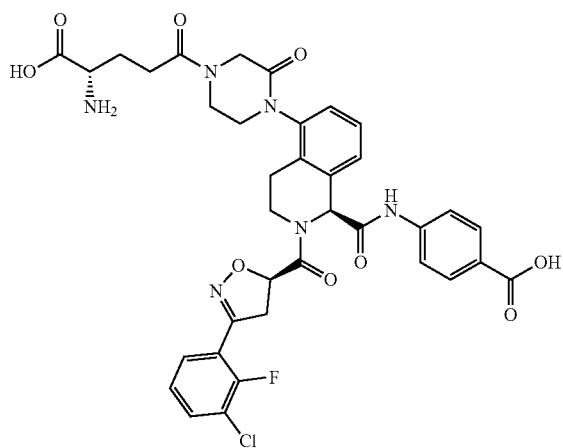

14

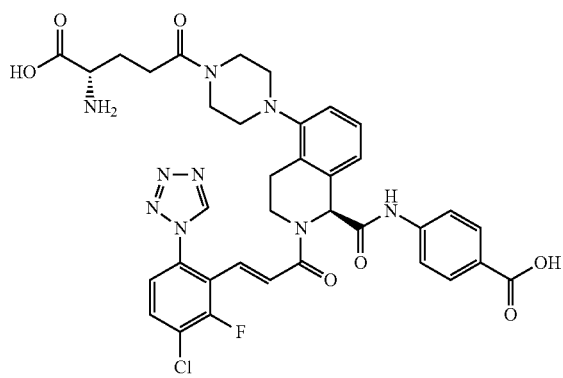

15

16-a

Further provided is a compound of formula (I), formula (II), formula (III), formula (IVa), formula (IVb) or a pharmaceutically acceptable salt of any one of the specific compounds listed above, wherein the pharmaceutically acceptable salt is an acid addition salt, and the acid forming the acid addition salt is selected from the group consisting of formic acid, acetic acid, trifluoroacetic acid, hexane diacid, aspartic acid, benzoic acid, benzenesulfonic acid, carbonic acid, sulfuric acid, boric acid, camphorsulfonic acid, citric acid, cyclamic acid, ethylenedisulfonic acid, ethanesulfonic acid, fumaric acid, glucoheptoic acid, gluconic acid, glucuronic acid, hexafluorophosphoric acid, hydrobromic acid, hydroiodic acid, isethionic acid, lactic acid, malic acid, maleic acid, malonic acid, methanesulfonic acid, methylsulfuric acid, naphthoic acid, 2-naphthalenesulfonic acid, nicotinic acid, nitric acid, orotic acid, oxalic acid, palmitic acid, pamoic acid, phosphoric acid, pyroglutamic acid, aldaric acid, stearic acid, succinic acid, tannic acid, tartaric acid and toluenesulfonic acid; preferably, the acid forming the acid addition salt is selected from the group consisting of formic acid, acetic acid and trifluoroacetic acid. In a particularly preferred embodiment, the acid forming the acid addition salt is formic acid; the acid addition salt is formate.

In one embodiment, the pharmaceutically acceptable salt of the compound of the present disclosure can be expressed, for example, in the following manner:

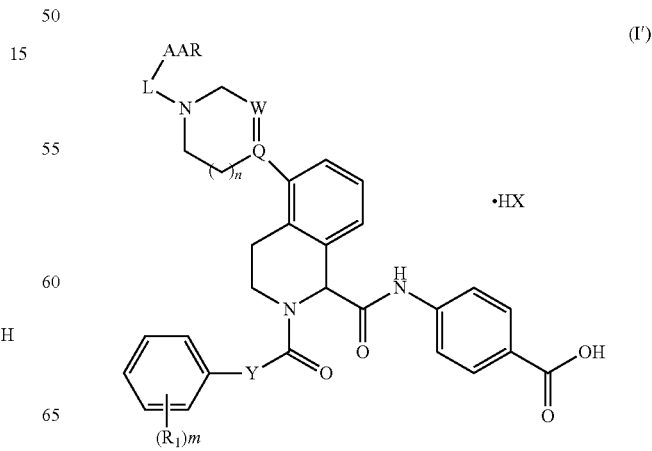

(I')

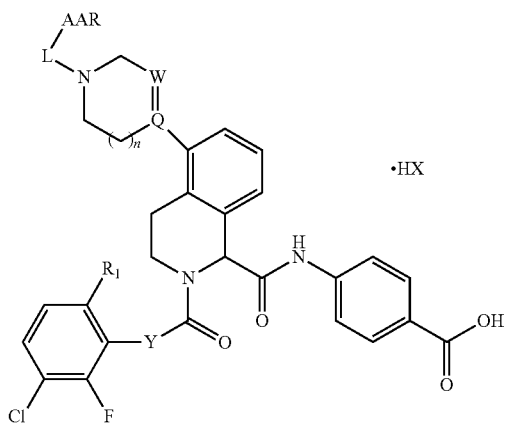

(II')

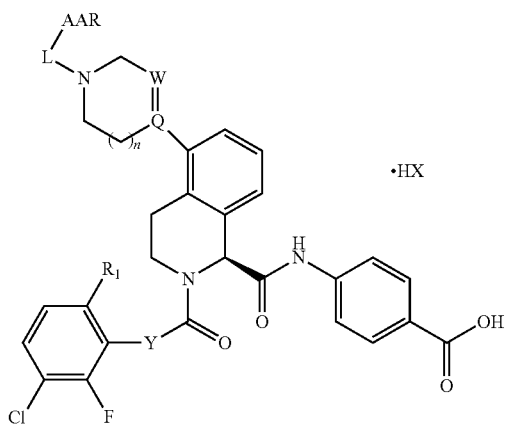

(III')

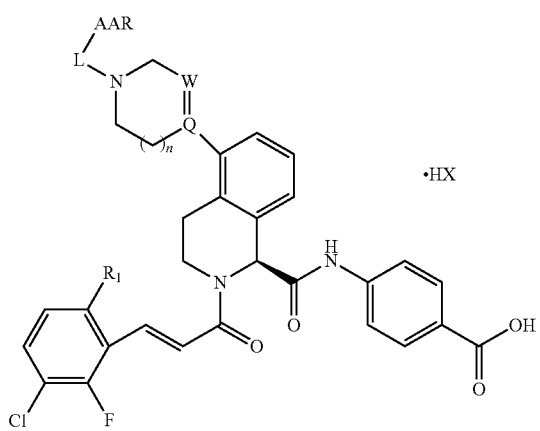

(IVa')

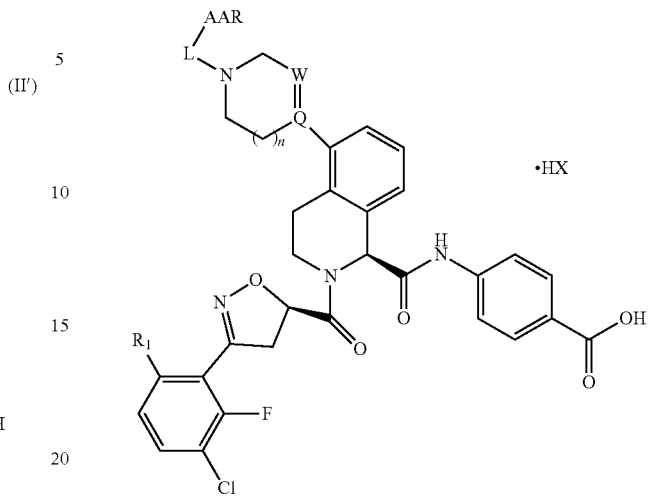

(IVb')

wherein, each of the groups is as defined above.

HX in the formula (I'), (II'), (III'), (IVa'), (IVb') is selected from the group consisting of formic acid, acetic acid, trifluoroacetic acid, hexane diacid, aspartic acid, benzoic acid, benzenesulfonic acid, carbonic acid, sulfuric acid, boric acid, camphorsulfonic acid, citric acid, cyclamic acid, ethylenedisulfonic acid, ethanesulfonic acid, fumaric acid, glucoheptoic acid, gluconic acid, glucuronic acid, hexafluorophosphoric acid, hydrobromic acid, hydroiodic acid, isethionic acid, lactic acid, malic acid, maleic acid, malonic acid, methanesulfonic acid, methylsulfuric acid, naphthoic acid, 2-naphthalenesulfonic acid, nicotinic acid, nitric acid, orotic acid, oxalic acid, palmitic acid, pamoic acid, phosphoric acid, pyroglutamic acid, aldaric acid, stearic acid, succinic acid, tannic acid, tartaric acid and toluenesulfonic acid; preferably, HX is selected from the group consisting of formic acid, acetic acid and trifluoroacetic acid, particularly formic acid.

In a particularly preferred embodiment, HX is formic acid; the salt is formate, for example can be expressed in the following manner:

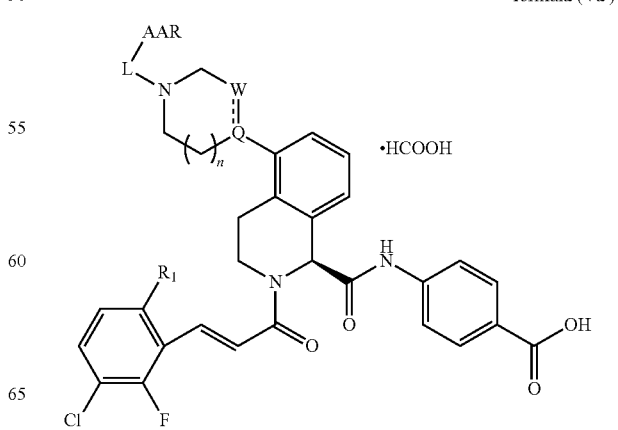

formula (Va')

formula (Vb')
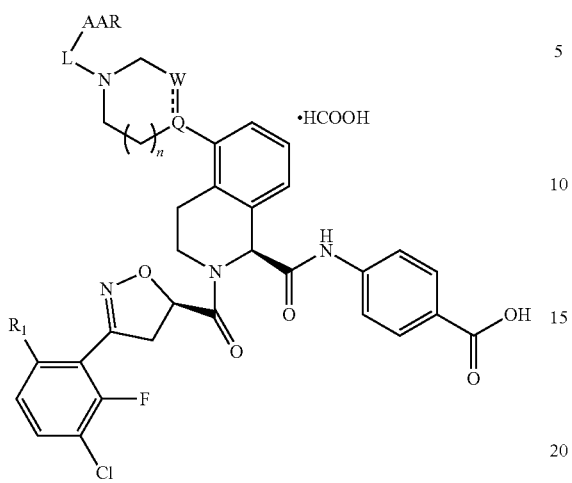
wherein, each group is defined as above.
In a particularly preferred embodiment, pharmaceutically acceptable salt of the compound of the present disclosure can be expressed, for example, in the following manner:
TM-1-a
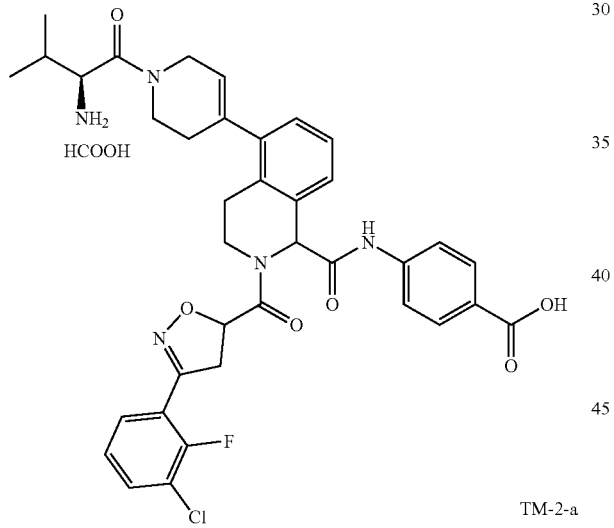
TM-2-a
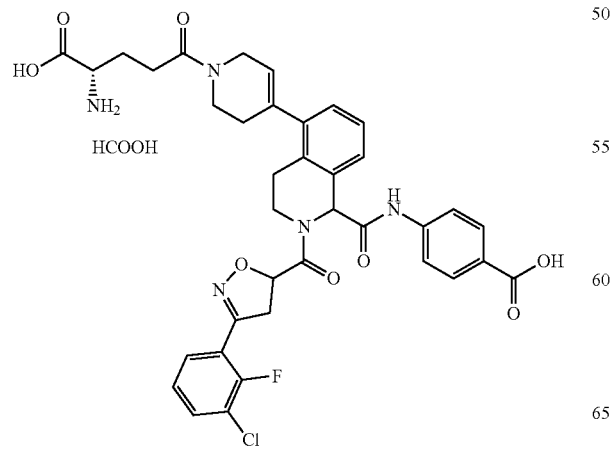
TM-3-a
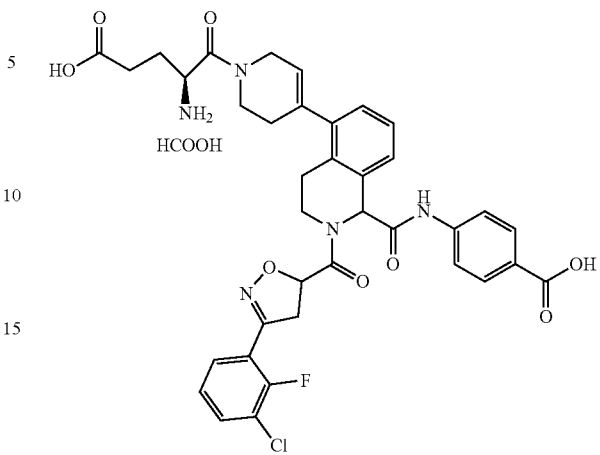
TM-1
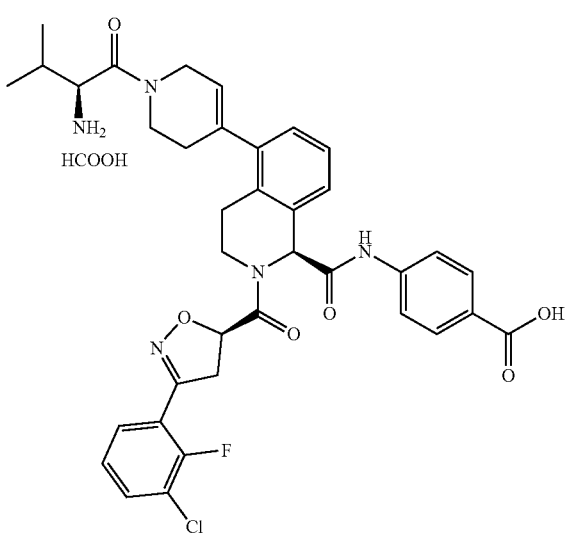
TM-2
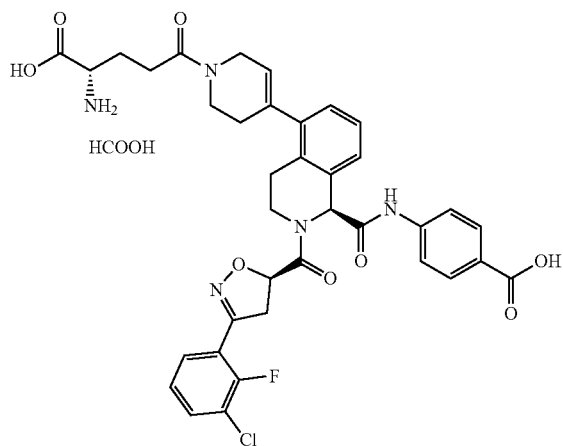

TM-3
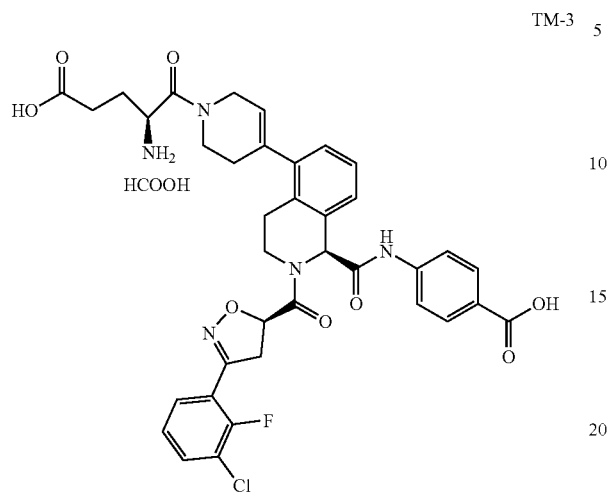
TM-6-a
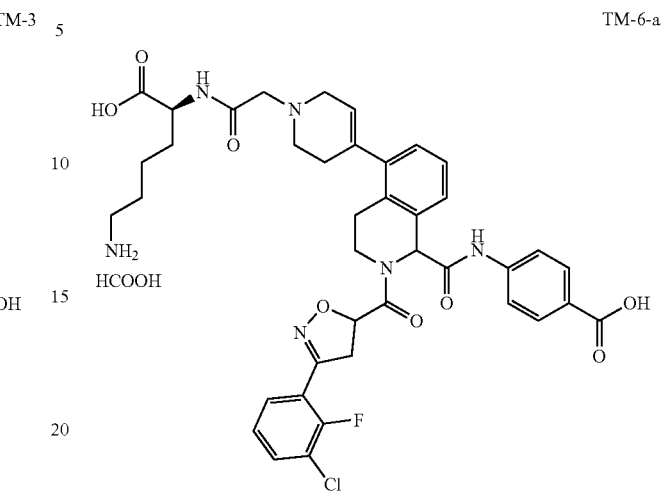
TM-4-a
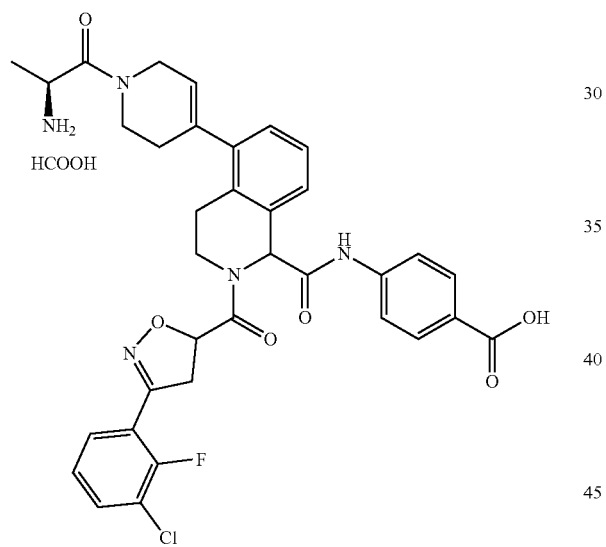
TM-4
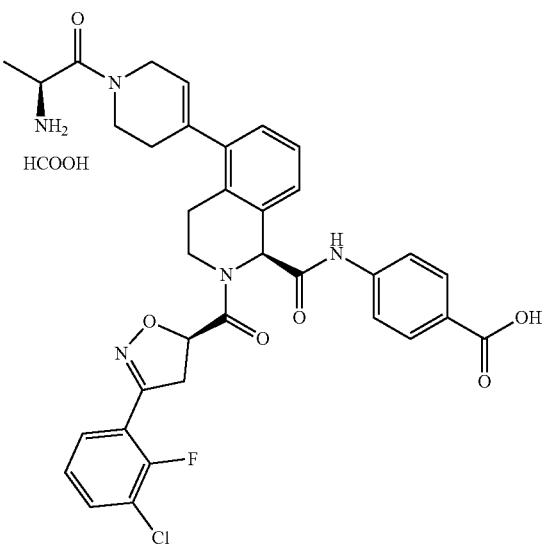
TM-5-a
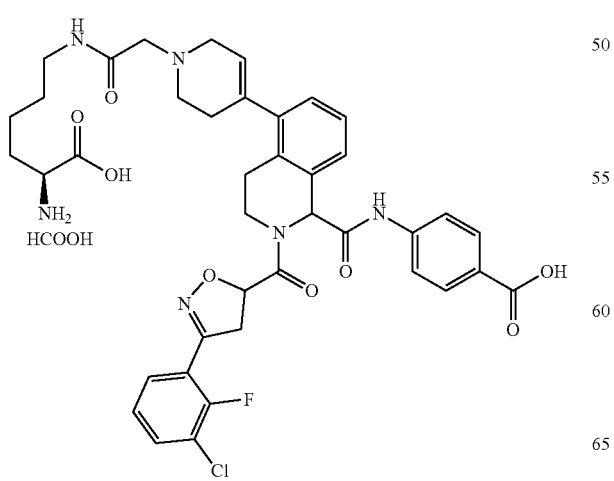
TM-5
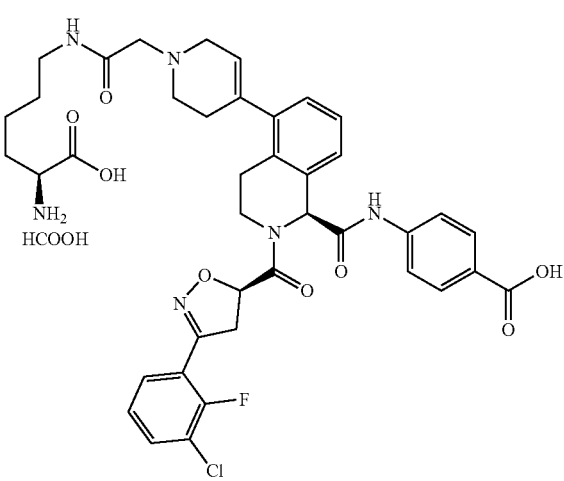

-continued
TM-6
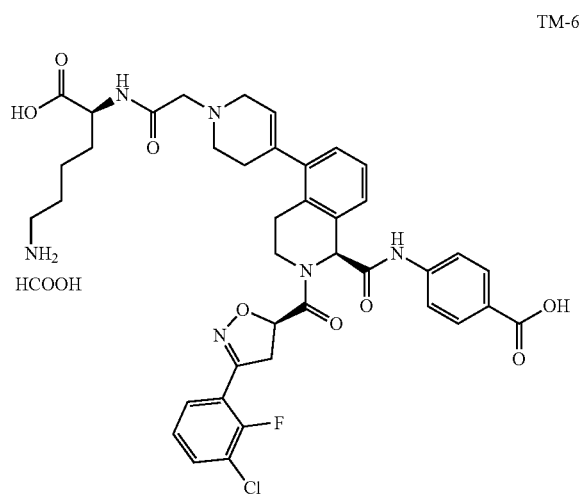
TM-7-a
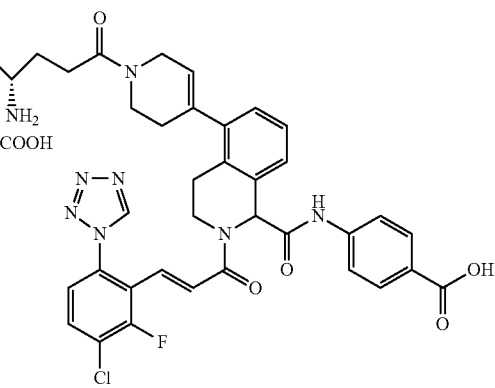
TM-8-a
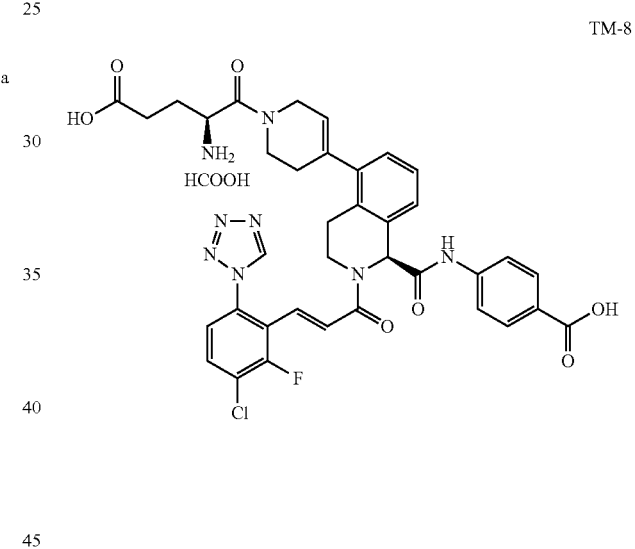
-continued
TM-9-a
TM-8
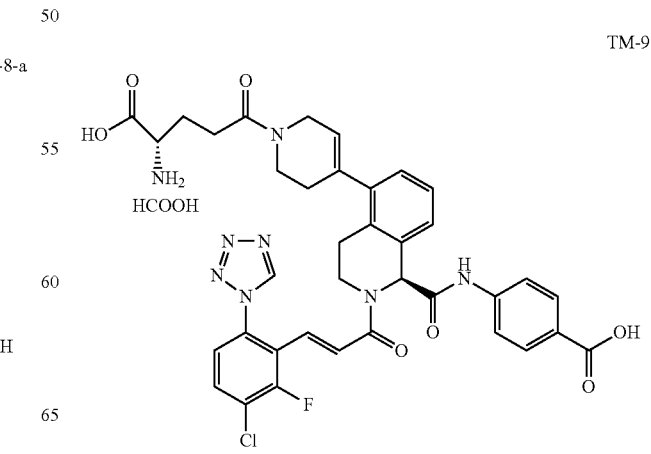
TM-9

45
-continued
TM-10-a
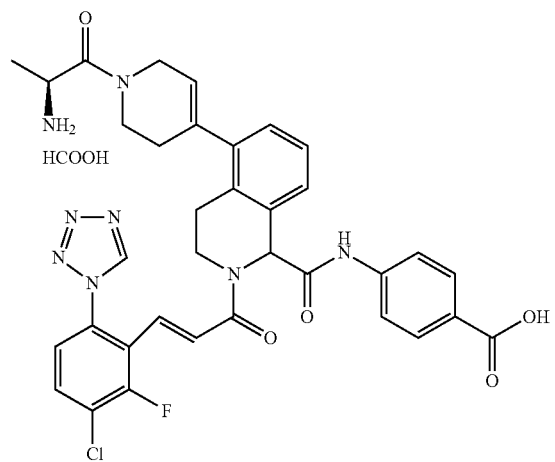
TM-11-a
TM-12-a
TM-11
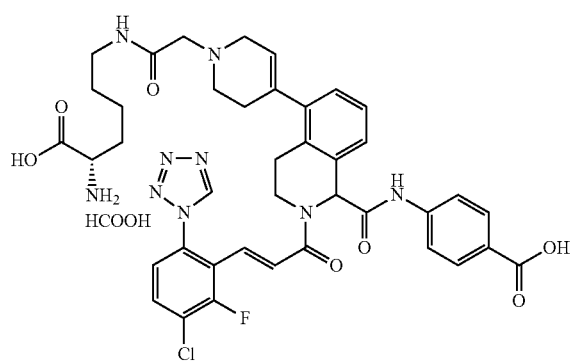
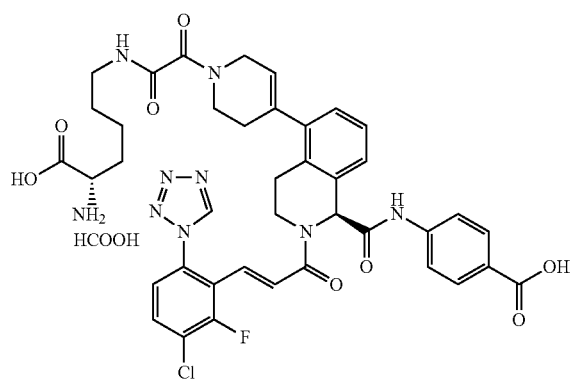
46
-continued
TM-12
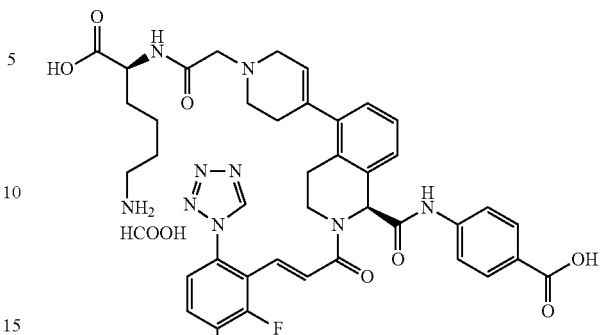
TM-13-a
TM-14-a
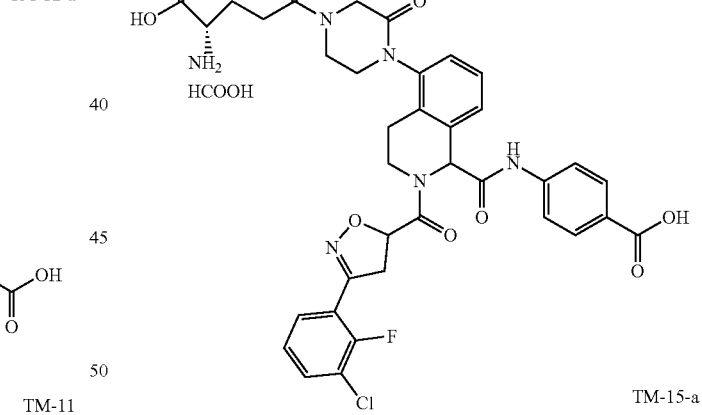
TM-15-a
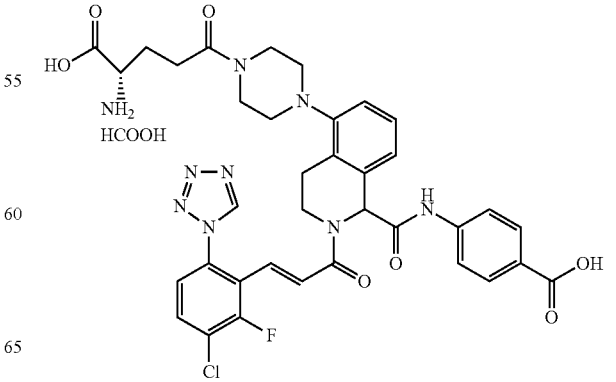

TM-13
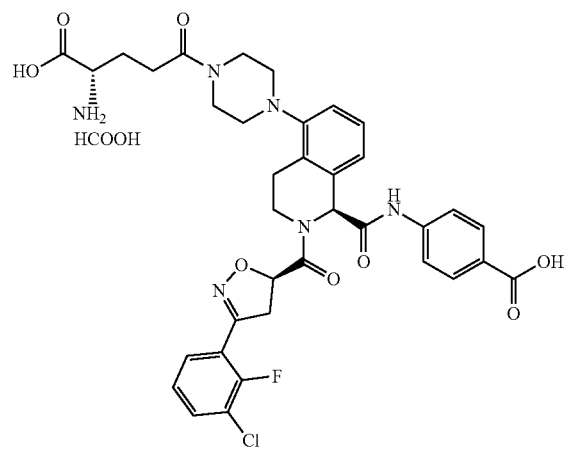
TM-14
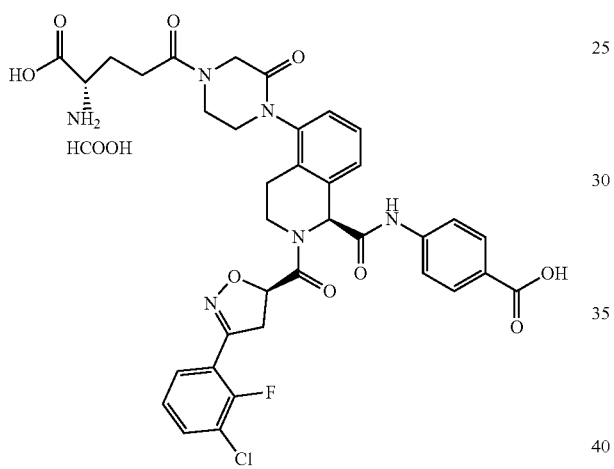
TM-15
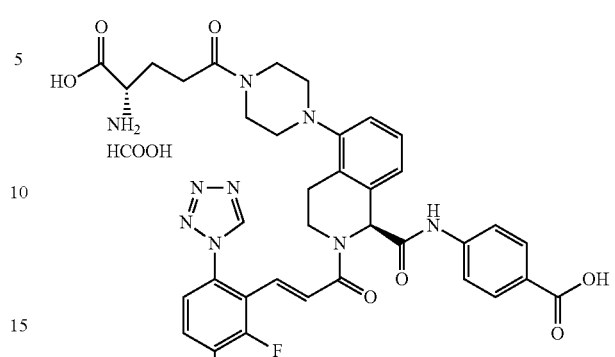
TM-16-a
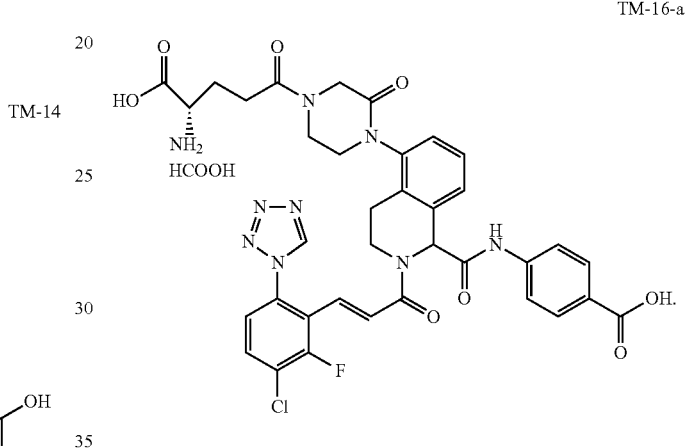
Preparation Process
Another object of the present disclosure is to provide a preparation process of a compound of formula (I) or a pharmaceutically acceptable salt thereof, comprising following steps:
(1) Preparation of Intermediate E:
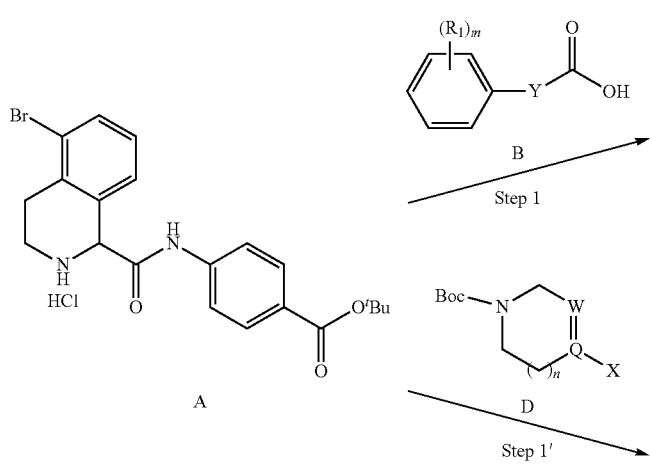

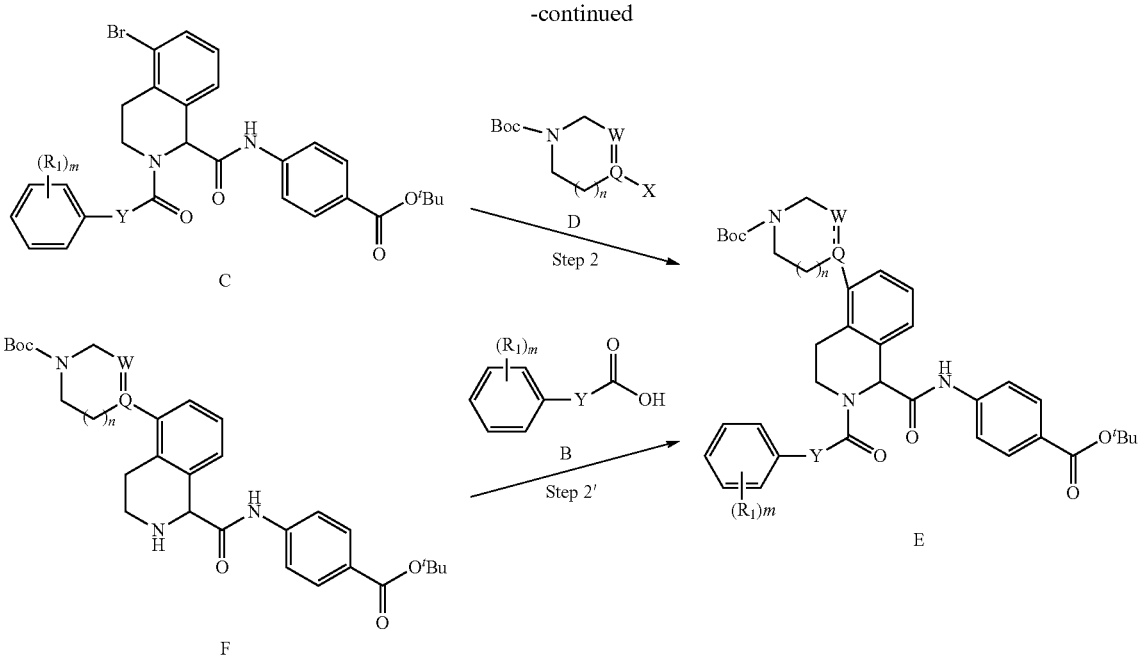

-continued wherein, X is hydrogen, boric acid or borate ester group, preferably —B(OH)$_2$ or

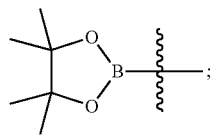

====, R$_1$, Y, W, Q, n and m are as defined above;

Route 1:

Step 1: reacting compound A with compound B through condensation reaction to obtain compound C;

Step 2: reacting compound C with compound D through coupling reaction to obtain compound E;

Route 2: Step 1': reacting a compound A with compound D through coupling reaction to obtain compound F.

Step 2': reacting compound F with compound B through condensation reaction to obtain compound E.

The condensation reaction is carried out in the presence of condensing agent and organic base. The condensing agent used herein may be HATU, HBTU, HCTU, HOBt/EDCI, DMC, DCC, DIC, EDCI, BOP, PyBOP, PyAOP or the like, preferably HATU, HOBt/EDCI, EDCI. The organic base used herein may be TEA, DMAP, DIEA, pyridine or the like, preferably DIEA, TEA, pyridine. The condensation reaction may be carried out in an organic solvent. Suitable organic solvents include DMF, halohydrocarbon (e.g. chloroform, dichloromethane, dichloroethane), ethers (e.g. 1,4-dioxane, tetrahydrofuran, dimethyl ether, diethyl ether, methyl tert-butyl ether). The reaction temperature may be 0 to 100° C., preferably 0° C. and room temperature. The reaction time is in the range of 1-24 hours, preferably 1-3 hours.

The coupling reaction is carried out in the presence of metal catalyst and base. The metal catalyst is palladium metal catalyst, e.g. tetra (triphenylphosphine)palladium, [1,1'-bis (diphenylphosphine)ferrocene] palladium dichloride, [1,1'-bis(diphenylphosphine)ferrocene] palladium dichloride dichloromethane complex, bis(triphenylphosphine)palladium dichloride, palladium acetate, preferably [1,1'-bis(diphenylphosphine)ferrocene]palladium dichloride dichloromethane complex. The base is inorganic base, for example cesium carbonate, potassium carbonate, sodium carbonate, potassium hydrogen carbonate, sodium hydrogen carbonate, preferably cesium carbonate. The coupling reaction may be carried out in a suitable organic solvent or a mixed solvent of an organic solvent and water. The organic solvent may be selected from the group consisting of 1,4-dioxane, N,N-dimethylformamide and a mixed solvent of an organic solvent above and water, for example a mixed solvent of 1,4-dioxane and water. The coupling reaction is carried out in a suitable protective atmosphere (for example nitrogen atmosphere). The reaction temperature may be 0-150° C., preferably 100-130° C.; the reaction time is in the range of 2-48 hours, preferably 8-12 hours.

(2) Preparation of a compound of formula (I) or a pharmaceutically acceptable salt thereof:

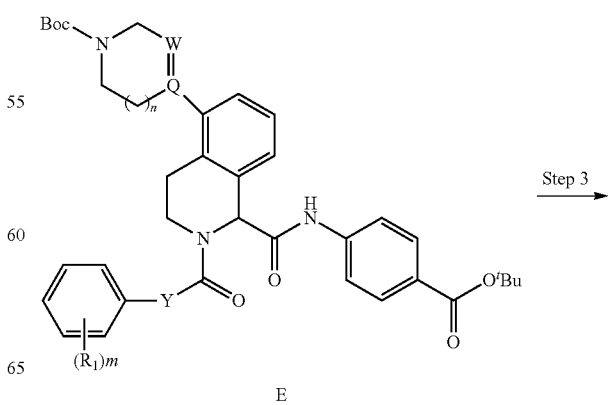

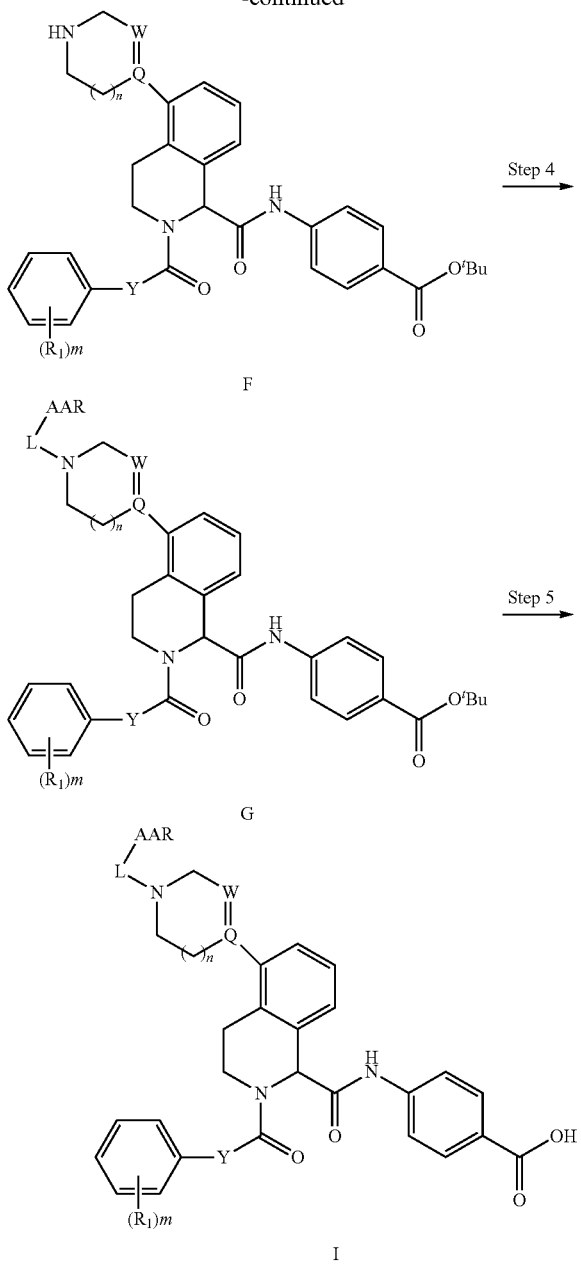

wherein, ====, $R_1$, L, AAR, Y, W, Q, n and m are as defined above;

Step 3: deprotecting compound E under acidic conditions to obtain compound F;

Step 4: reacting compound F with a carboxylic acid, carboxylic acid derivative or halohydrocarbon to connect with a -L-AAR group, then obtaining compound G;

Step 5: deprotecting compound G under acidic conditions, purifying and optionally generating the free form and/or generating the salt form, then obtaining a compound of formula (I) or a pharmaceutically acceptable salt thereof.

The deprotection reaction is carried out in the presence of deprotecting reagent, under the condition of low temperature, room temperature or heating. The deprotecting reagent used herein may be trifluoroacetic acid, sulfuric acid or the like, preferably trifluoroacetic acid. Suitable organic solvents include halohydrocarbon (e.g. chloroform, dichloromethane, dichloroethane), ethers (e.g. 1,4-dioxane, tetrahydrofuran, dimethyl ether, diethyl ether, methyl tert-butyl ether), DMF or the like, preferably dichloromethane, tetrahydrofuran, 1,4-dioxane. The reaction temperature may be 0-100° C., preferably 0-50° C. The reaction time is in the range of 0.5-24 hours, preferably 0.5-3 hours. More detailed operation procedures can be found, for example, in Protective Groups in Organic Synthesis (Greene et al, 4th Ed, Wiley-Interscience (2006)).

The condensation reaction of the carboxylic acid is carried out in the presence of an organic base. The condensing agent used herein may be HATU, HBTU, HCTU, HOBt/EDCI, DMC, DCC, DIC, EDCI, BOP, PyBOP, PyAOP or the like, preferably HATU, HOBt/EDCI, EDCI. The organic base used herein may be TEA, DMAP, DIEA, pyridine or the like, preferably DIEA, TEA, pyridine. The condensation reaction may be carried out in an organic solvent. Suitable organic solvents include DMF, halohydrocarbon (e.g. chloroform, dichloromethane, dichloroethane), ethers (e.g. 1,4-dioxane, tetrahydrofuran, dimethyl ether, diethyl ether, methyl tert-butyl ether). The reaction temperature may be 0 to 100° C., preferably 0° C. and room temperature. The reaction time is in the range of 1-24 hours, preferably 1-3 hours.

The substitution reaction of halohydrocarbon is carried out in the presence of base. The base used herein may be inorganic base $K_2CO_3$, $Na_2CO_3$, $Cs_2CO_3$, KOtBu or the like, preferably $K_2CO_3$. The base used herein may be organic base DBU, DIEA, TEA, pyridine or the like, preferably DBU. The substitution reaction may be carried out in an organic solvent. Suitable organic solvents include DMF, halohydrocarbon (e.g. chloroform, dichloromethane, dichloroethane), ethers (e.g. 1,4-dioxane, tetrahydrofuran, dimethyl ether, diethyl ether, methyl tert-butyl ether). The reaction temperature may be 0 to 100° C., preferably room temperature and 80° C. The reaction time is in the range of 1-96 hours, preferably 3-8 hours.

The purification process includes HPLC purification, column chromatography, recrystallization. The HPLC purification uses preparative HPLC. The mobile phase is acid/methanol/water, and the acid used herein may be formic acid or trifluoroacetic acid. Column chromatography is also called chromatography, of which the separation principle is based on the differences in adsorption capacity of the substances to the stationary phase. Generally, the substance with high polarity tends to be adsorbed onto the stationary phase, and the substance with low polarity is more difficult to be adsorbed to the stationary phase. The column chromatography process is a process of adsorption, desorption, readsorption and desorption. Recrystallization is the process of recrystallizing from a solution or a melt after dissolving the crystals in the solvent or melting the crystals.

In addition, the compounds of the present disclosure can further be prepared in a variety of ways known to those skilled in the art of organic synthesis. The compounds of the present disclosure can be synthesized using the processes described below as well as synthetic processes known in the art of organic chemistry or variations thereof understood by those skilled in the art. Preferred processes include (but not limited to) those described above. The reaction can be carried out in a solvent or solvent mixture that is suitable for the reagents and materials used herein and suitable for the conversion. Those skilled in the art of organic synthesis should understand that the functional groups present on the molecule should be consistent with the proposed conversion. Sometimes, this will require following judgements: modifying the sequence of the synthetic steps or choosing another specific synthetic route than one synthetic route to obtain the desired compounds of the present disclosure.

It should be further understood that another primary consideration of designing any synthetic route in the art is the correct selection of protective group for protecting the reactive functional group in the compound of the present disclosure. An authoritative description of many alternative proposals is Protective Groups in Organic Synthesis (Greene et al, 4th Ed, Wiley-Interscience (2006)).

Unless otherwise stated, the substituents of the compound in the routes above are as defined in the present disclosure. Those skilled in the art will understand that one or more steps in the routes above may be omitted according to the structure of the desired product. Those skilled in the art can also adjust the sequence of the steps, if necessary.

Pharmaceutical Composition and Pharmaceutical Formulation

Another object of the present disclosure is to provide a pharmaceutical composition comprising a prophylactically or therapeutically effective amount of the compound of the present disclosure or a pharmaceutically acceptable salt, ester, stereoisomer, tautomer, polymorph, solvate, isotopically labeled compound, metabolite or prodrug thereof, or a mixture of the foregoing, and one or more pharmaceutically acceptable carriers.

"Pharmaceutically acceptable carrier" in the present disclosure refers to a diluent, adjuvant, excipient or vehicle with which the treatment reagent is administered, and which is suitable for contacting humans and/or other animals within the scope of reasonable medical judgment without excessive toxicity, irritation, anaphylactic response or other problems or complications corresponding to a reasonable benefit/risk ratio.

The pharmaceutically acceptable carriers which can be employed in the pharmaceutical composition of the present disclosure include, but are not limited to, sterile liquids, such as water and oils, including those of petroleum, animal, vegetable or synthetic origin, such as peanut oil, soybean oil, mineral oil, sesame oil or the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol or the like. The pharmaceutical composition, if desired, can also contain minor amounts of wetting or emulsifying agents, or pH buffering agents. Oral formulations can include standard carriers such as mannitol, lactose, starch, magnesium stearate, sodium saccharine, cellulose, magnesium carbonate, etc., of pharmaceutical grade.

The pharmaceutical composition of the disclosure may act systemically and/or locally. For this purpose, they may be administered in a suitable route, for example by injection (e.g. intravenous, intraarterial, subcutaneous, intraperitoneal, intramuscular injection, including dripping) or transdermal administration; or by the form of oral, buccal, per nasal, transmucosal, topical, ophthalmic formulation or by inhalation.

For these administration routes, the pharmaceutical composition of the present disclosure may be administered in a suitable dosage form. The dosage forms include, but not limited to, tablets, capsules, troches, hard candy, powders, sprays, creams, ointments, suppositories, gels, pastes, lotions, ointments, aqueous suspensions, injectable solution, elixirs, syrups or the like.

The content or amount of the compound of the present disclosure in the pharmaceutical composition may be about 0.01 mg to about 1000 mg, suitably 0.1-500 mg. preferably 0.5-300 mg, more preferably 1-150 mg, particularly preferably 1-50 mg, e.g. 1.5 mg, 2 mg, 4 mg, 10 mg, 25 mg.

According to some embodiments of the present disclosure, the pharmaceutical composition may further comprise one or more other treatment reagents, for example other treatment reagents for preventing or treating a coagulation factor XIa inhibition associated disease.

Another object of the present disclosure is to provide a process for preparing a pharmaceutical composition of the present disclosure, which comprises combining the compound of the present disclosure, or the pharmaceutically acceptable salt, ester, stereoisomer, tautomer, polymorph, solvate, isotopically labeled compound, metabolite or prodrug thereof, or a mixture thereof with one or more pharmaceutically acceptable carriers.

Another object of the present disclosure is to provide a pharmaceutical formulation, which comprises the compound of the present disclosure or the pharmaceutically acceptable salt, ester, stereoisomer, tautomer, polymorph, solvate, isotopically labeled compound, metabolite or prodrug thereof, or a mixture thereof, or the pharmaceutical composition of the present disclosure. The formulation is in the form of solid formulation, semisolid formulation, liquid formulation or gaseous formulation.

Method of Treatment and Use

Another object of the present disclosure is to provide a compound of the present disclosure or a pharmaceutically acceptable salt, ester, stereoisomer, tautomer, polymorph, solvate, isotopically labeled compound, metabolite or prodrug thereof, or a mixture thereof, or use of a pharmaceutical composition of the present disclosure in the preparation of a medicament for treating a coagulation factor XIa inhibition associated disease.

According to some embodiments of the present disclosure, the compounds of the present disclosure can be used for preventing or treating a coagulation factor XIa inhibition associated disease, or a disease that responds to coagulation factor XIa inhibition, which include, but not limited to, thromboembolic disorder, wherein the thromboembolic disorder preferably incudes arterial cardiovascular thromboembolic disorder, venous cardiovascular thromboembolic disorder or thromboembolic disorder of the heart chamber.

More preferably, the thromboembolic disorder includes unstable angina pectoris, acute coronary syndrome, atrial fibrillation, first attack of myocardial infarction, recurrent myocardial infarction, ischemic sudden death, transient ischemic attack, stroke, atherosclerosis, occlusive peripheral arterial disease, phlebothrombosis, deep venous thrombosis, thrombophlebitis, arterial thrombosis, coronary thrombosis, cerebral artery thrombosis, cerebral embolism, kidney embolism, pulmonary embolism, or thrombosis caused by (a) artificial valves or other implants, (b) indwelling catheter, (c) frame, (d) extracorporeal circulation, (e) hemodialysis, or (0 exposure of blood to artificial surface that is prone to form thrombosis.

The term "effective amount" refers to the amount of a compound that, after administration, will alleviate to certain extent one or more symptoms of the condition being treated.

The optimal desired response can be provided by adjusting administration regimen. For example, a single bolus may be administered, several partial doses may be administered over time, or the doses may be reduced or increased proportionally as indicated by the urgent need for treatment. It is noted that, the dosage may vary with the type and severity of the condition to be alleviated, and single or multiple doses can be included. It is to be further understood that, for any particular individual, the specific administration regimen should be adjusted over time according to the individual needs and the professional judgment of the person administering the composition or supervising the administration of the composition.

The amount of the compound of the present disclosure administered will depend on the subject to be treated, the severity of the disorder or condition, the rate of administration, the disposition of the compound and the discretion of the prescribing physician. Generally, an effective dosage is in the range of about 0.0001 mg to about 50 mg per kg body weight per day, for example about 0.01 mg/kg/day to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, larger doses can still be employed without causing any harmful side effect, provided that such larger doses are first divided into several small doses for administration throughout the day.

Unless otherwise stated, the term "treatment" as used herein refers to reversing, alleviating, inhibiting the progression of a disorder or condition to which the term applies or the progression of one or more symptoms of such a disorder or condition, or preventing such a disorder or condition or one or more symptoms of such a disorder or condition.

"Individual" as used herein includes human or non-human animals. Exemplary human individuals include a human individual (called a patient) having a disease (for example the disease described herein) or a normal individual. "Non-human animals" in the present disclosure include all vertebrates, for example non-mammals (e.g. birds, amphibians, reptiles) and mammals, for example non-human primates, domestic animals, and/or domesticated animals (e.g. sheep, dogs, cats, cows, pigs).

Beneficial Effect

The compounds of the present disclosure are capable of achieving at least one of the following technical effects:

(1) having high solubility;

(2) having low membrane permeability, which on the one hand reduces the penetration of compound into other tissues and cells, and on the other hand makes the drug to mainly distribute in the blood after injection into blood vessels, resulting in lower apparent volume of distribution, and can thereby reduce the drug dosage, and reduce the side effects unrelated to the anticoagulant effect. The toxicity is reduced;

(3) having strong inhibitory effect on coagulation factor XIa, and has no inhibitory effect on coagulation factor Xa and VIIa. Therefore, it has higher selectivity and reduced side effects;

(4) having improved safety.

EXAMPLES

Preparation Example

In order to make the objects and technical solutions of the present disclosure clearer, the present disclosure will be further described below in combination with specific examples. It should be understood that the examples are only used for illustrative purpose and not intended to limit the scope of the present disclosure. Moreover, specific experimental processes that are not mentioned in the following examples are carried out in accordance with a conventional experimental process.

The structure of the compound described in the following examples is determined by nuclear magnetic resonance ($^1$H NMR) or mass spectrometry (MS).

The $^1$H NMR shift (δ) is given in parts per million (ppm). $^1$H NMR is determined by JEOL Eclipse 400 Spectrometer, and the determination solvents are deuteromethanol ($CD_3OD$), deuterochloroform ($CDCl_3$), hexadeuterated dimethyl sulfoxide (DMSO-$d_6$), internal standard is tetramethylsilane (TMS), chemical shift is given in unit of $10^{-6}$ (ppm).

The abbreviations in the nuclear magnetic resonance (NMR) data used in the examples are shown below:

s: single peak, d: doublet, t: triplet, q: quartet, dd: double doublet, qd: quartet doublet, ddd: double double doublet, ddt: double double triplet, dddd: double double double doublet, m: multiplet, br: broad, J: coupling constant, Hz: Hertz.

MS is measured by Agilent (ESI) mass spectrometer, manufacturer: Agilent; model: Agilent 6120B;

Preparative high-performance liquid chromatography uses Shimadzu LC-8A preparative liquid chromatography (YMC, ODS, 250×20 mm column).

Thin layer chromatography silica gel plate (TLC) uses aluminum plates (20×20 cm) manufactured by Merck. Separation and purification of thin layer chromatography uses GF 254 (0.4~0.5 mm) manufactured in Yantai.

The reaction is monitored by thin layer chromatography (TLC) or LCMS, and the developing solvent systems used herein are: system of dichloromethane and methanol, system of n-hexane and ethyl acetate system, system of petroleum and ethyl acetate. The volume ratio of the solvent is adjusted according to different polarities of compounds or by adding triethylamine or the like.

Microwave reaction is carried out using a BiotageInitiator+(400 W, RT~300° C.) microwave reactor.

Column chromatography generally uses Qingdao Ocean 200~300 mesh silica gel as carrier. Eluent systems include: system of dichloromethane and methanol, system of n-hexane and ethyl acetate system. Volume ratio of the solvent is adjusted according to different polarities of compounds, and may also be adjusted by adding a small amount of triethylamine.

Unless specially stated in the examples, the temperature of reaction is room temperature (20° C.~30° C.).

The reagents in the present disclosure are purchased from companies such as Acros Organics, Aldrich Chemical Company, Topbiochem.

In conventional synthesis processes, examples, and intermediate synthesis examples, the meanings of abbreviations are as follows.

DMA: N,N-dimethylacetamide; DMSO: dimethyl sulfoxide; NMP: N-methyl pyrrolidone; DIBAL-H: diisobutylaluminum hydride; DIPEA: N,N-diisopropylethylamine; THF: tetrahydrofuran; Boc: tert-butoxycarbonyl; NBS: N-bromosuccinimide; Cbz-Cl: benzyl chloroformate; TFA: trifluoroacetic acid; Et$_2$O: diethyl ether; EtOH: ethanol; Dioxane: 1,4-dioxane; TLC: thin layer chromatography; Me: methyl; MTBE: methyl tertiary butyl ether; HATU: O-(7-aza benzotriazole-1-yl)-N,N,N',N'-tetramethylurea hexafluorophosphate; DCM: dichloromethane; EA: ethyl acetate; Xphos: 2-dicyclohexylphosphine-2',4',6'-triisopropylbiphenyl; PE: petroleum ether; Hexane: n-hexane; HOAc: acetic acid; tBu: tert-butyl; DMF: N,N-dimethylformamide; DIPEA: N,N-diisopropylethylamine; MeCN: acetonitrile; HEPES: 4-hydroxyethyl piperazine ethanesulfonic acid.

Example 1
4-((S)-5-(1-((S)-2-amino-3-methylbutanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid
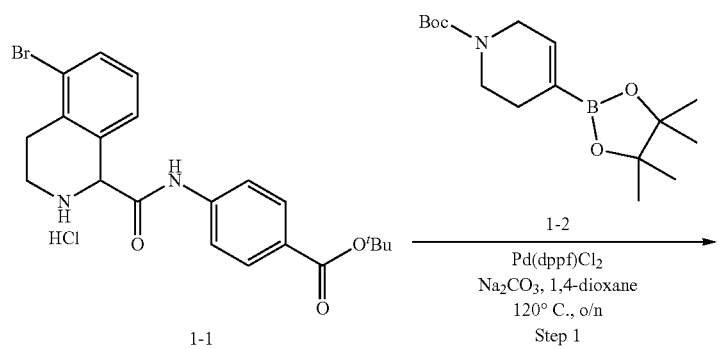
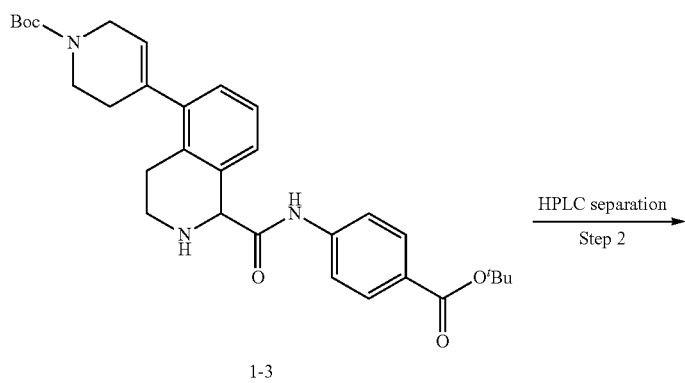
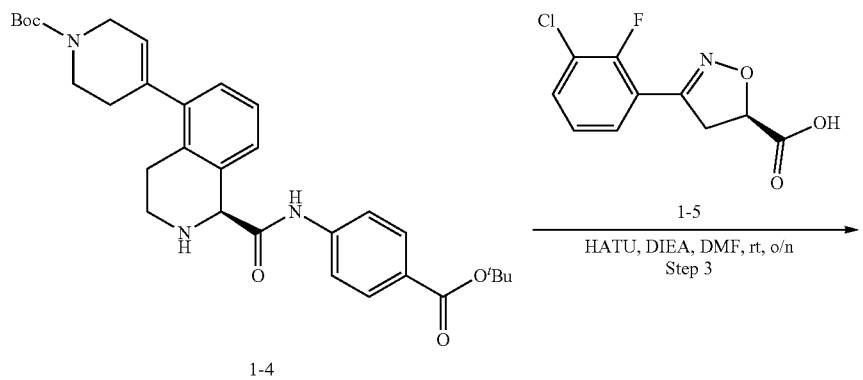

-continued
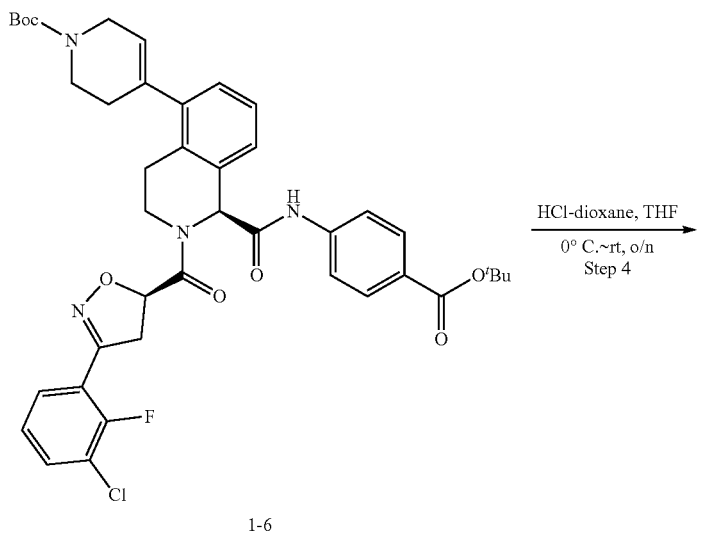
1-6
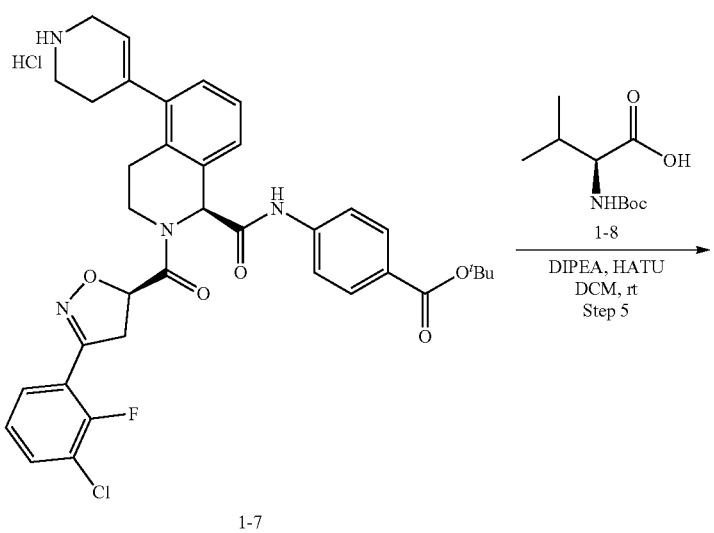
1-7
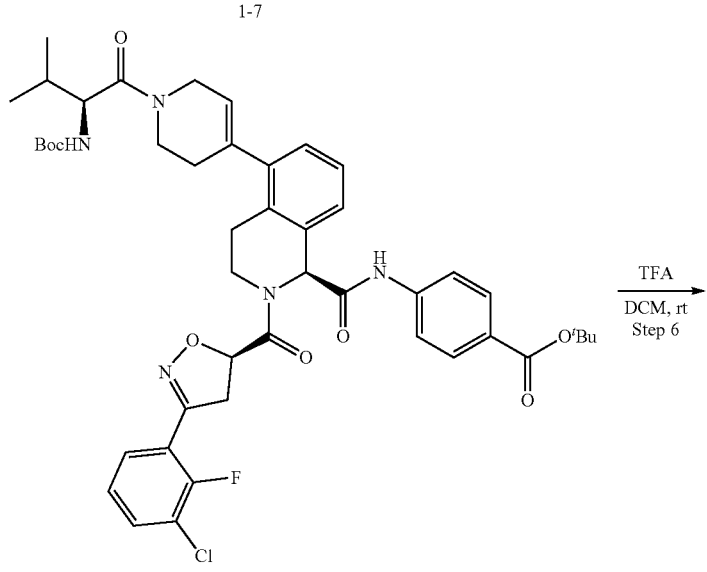
1-9

-continued

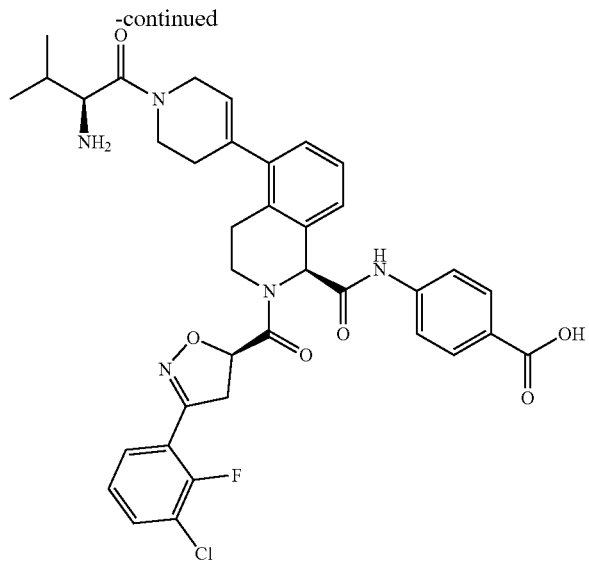

Step 1: Preparation of 4-(1-((4-(tert-butoxycarbonyl) phenyl) carbamoyl)-1,2,3,4-tetrahydroisoquinolin-5-yl)-3,6-dihydropyridine-1(2H)-carboxylic acid tert-butyl ester (1-3)

Compound 4-(5-bromo-1,2,3,4-tetrahydroisoquinoline-1-carboxamido)benzoic acid tert-butyl ester hydrochloride (synthesis process can be referred to CN107540659A, 20 g, 43 mmol), 4-(4,4,5,5-tetramethyl-1,3,2-dioxaborolan-2-yl)-3,6-dihydropyridine-1 (2H)-carboxylate tert-butyl ester (1-2, 14.6 g, 47.3 mmol). Sodium carbonate (29 g, 215 mmol) were dissolved in a mixed solvent of 1,4-dioxane/water (5/1) (180 mL). Pd(dppf)Cl$_2$(3.1 g, 4.3 mmol) was added under N$_2$ atmosphere. Then the reaction was conducted overnight in an oil bath at 120° C. The reaction was cooled to room temperature and then quenched with water. The reaction mixture was extracted with ethyl acetate, then concentrated, and separated by column chromatography to obtain the title compound (1-3, 20.7 g, yield: 90.3%).

MS m/z (ESI): 534 [M+H]$^+$

Step 2: Preparation of (S)-4-(1-((4-(tert-butoxycarbonyl) phenyl) carbamoyl)-1,2,3,4-tetrahydroisoquinolin-5-yl)-3,6-dihydropyridine-1(2H)-carboxylic acid tert-butyl ester (1-4)

Compound 1-3 (32.6 g) was separated by chiral HPLC (chromatographic column: IF Column; mobile phase: Hexane/EtOH/HOAc=80/20/0.1 (V/V/V); flow rate: 1.0 ml/min; detection wavelength: 214 nm; retention time: 11.97 min) to obtain the title compound (1-4, 11.7 g, yield: 35.9%).

MS m/z (ESI): 534 [M+H]$^+$

Step 3: Preparation of 4-((S)-1-((4-(tert-butoxycarbonyl) phenyl) carbamoyl)-2-((R)-3-(3-chloro-2-fluorophenyl)-4,5-dihydroisoxazole-5-carbonyl)-1,2,3,4-tetrahydroisoquinolin-5-yl)-3,6-dihydropyridine-1(2H)-carboxylic acid tert-butyl ester (1-6)

Compound 1-4 (10 g, 19 mmol), (R)-3-(3-chloro-2-fluorophenyl)-4,5-dihydroisoxazole-5-carboxylic acid (synthesis process can be referred to CN107540659A, 4.6 g, 19 mmol) were dissolved in DMF (25 mL), DIPEA (7.4 g, 57 mmol) and HATU (8.7 g, 23 mmol) were added. After addition, the mixture was stirred at room temperature overnight, then the reaction mixture was added to water, stirred for 10 minutes, filtered, and the filter cake was dried then purified through silica gel column to obtain the title compound (1-6, 12.6 g, yield: 85.4%).

$^1$H NMR (400 MHz, DMSO-d$_6$) δ 10.95-10.92 (s, 1H), 7.87-7.86 (d, 2H), 7.77-7.56 (m, 4H), 7.57-7.56 (d, 1H), 7.36-7.26 (m, 2H), 7.15-7.13 (s, 1H), 5.83 (s, 1H), 5.79-5.75 (s, 1H), 5.63 (s, 1H), 4.29-4.23 (m, 1H), 4.00 (s, 1H), 3.91-3.86 (m, 1H), 3.75-3.68 (m, 2H), 3.58 (m, 2H), 3.16-3.10 (m, 1H), 3.00-2.95 (m, 1H), 2.39-2.26 (m, 2H), 2.02 (s, 1H), 1.55 (s, 9H), 1.47 (s, 9H).

MS m/z (ESI): 759 [M+H]$^+$

Step 4: Preparation of 4-((S)-2-((R)-3-(3-chloro-2-fluorophenyl)-4,5-dihydroisoxazole-5-carbonyl)-5-(1,2,3,6-tetrahydropyridin-4-yl)-1,2,3,4-tetrahydroisoquinoline-1-carboxamido) benzoic acid tert-butyl ester hydrochloride (1-7)

Compound 4-((S)-1-((4-(tert-butoxycarbonyl) phenyl) carbamoyl)-2-((R)-3-(3-chloro-2-fluorophenyl)-4,5-dihydroisoxazole-5-carbonyl)-1,2,3,4-tetrahydroisoquinolin-5-yl)-3,6-dihydropyridine-1(2H)-carboxylic acid tert-butyl ester (1-6, 200 mg, 0.26 mmol) was dissolved in THF (5 mL), cooled to 0° C. in ice bath. Hydrochloric acid/1,4-dioxane solution (4 M, 3 mL) was added dropwise. After addition, the reaction stirred at room temperature for 2 hours. The reaction was monitored by LC-MS. After completion, ethyl ether (50 mL) was added. The reaction mixture was cooled to 0° C., stirred for 30 minutes, then filtered. The filter cake was dried to obtain the title compound (1-7, 103 mg, yield: 56.3%).

MS m/z (ESI): 659 [M+H]$^+$

Step 5: Preparation of 4-((S)-5-(1-((S)-2-((tert-butoxycarbonyl) amino)-3-methylbutanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid tert-butyl ester (1-9)

Under $N_2$, 0° C., Boc-valine (15 mg, 0.07 mmol) was dissolved in DCM (3 mL), DIPEA (27 mg, 0.2 mmol), HATU (39 mg, 0.1 mmol) and 4-((S)-2-((R)-3-(3-chloro-2-fluorophenyl)-4,5-dihydroisoxazole-5-carbonyl)-5-(1,2,3,6-tetrahydropyridin-4-yl)-1,2,3,4-tetrahydroisoquinoline-1-carboxamido)benzoic acid methyl ester hydrochloride (1-7, 48 mg, 0.07 mmol) were added sequentially. Then after warming to room temperature, the reaction was conducted for 2 h, and the reaction process was monitored by LC-MS. After the completion of the reaction, the reaction system can be directly used in the next step of reaction.

MS m/z (ESI): 858 $[M+H]^+$

Step 6: Preparation of 4-((S)-5-(1-((S)-2-amino-3-methylbutanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid Under 0° C., TFA (3 mL) was added to the reaction system of the previous step. Then after warming to room temperature, the reaction was conducted for 1 h. The reaction process was monitored by LC-MS. After the completion of the reaction, the excess TFA and solvent were removed under reduced pressure, and the obtained residue was separated by HPLC (formic acid/methanol/water) to obtain the formate of the title compound (11 mg, yield for two steps 22.7%).

$^1$H NMR (400 MHz, DMSO-$d_6$) δ 10.82 (s, 1H), 8.33 (s, 1H), 7.86 (d, J=8.7 Hz, 2H), 7.76-7.69 (m, 2H), 7.65 (d, J=8.8 Hz, 2H), 7.57 (d, J=7.7 Hz, 1H), 7.32 (t, J=8.0 Hz, 2H), 7.10 (d, J=7.5 Hz, 1H), 5.81 (s, 1H), 5.76-5.72 (m, 1H), 5.63 (m, 1H), 4.29-4.17 (m, 2H), 3.89-3.83 (m, 1H), 3.70-3.65 (m, 4H), 3.10-2.99 (m, 5H), 2.47-2.33 (m, 2H), 2.15-1.80 (m, 3H), 0.97-0.86 (m, 6H).

MS m/z (ESI): 702 $[M+H]^+$

Example 2: 4-((S)-5-(1-((S)-4-amino-4-carboxybutanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid

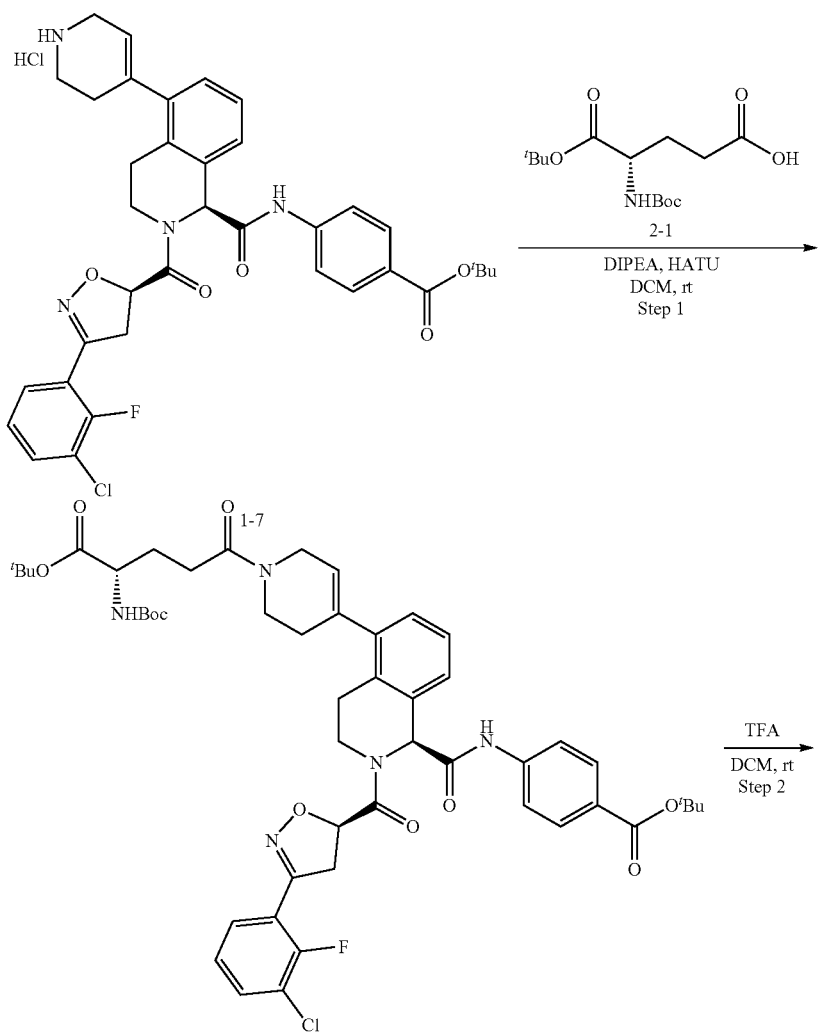

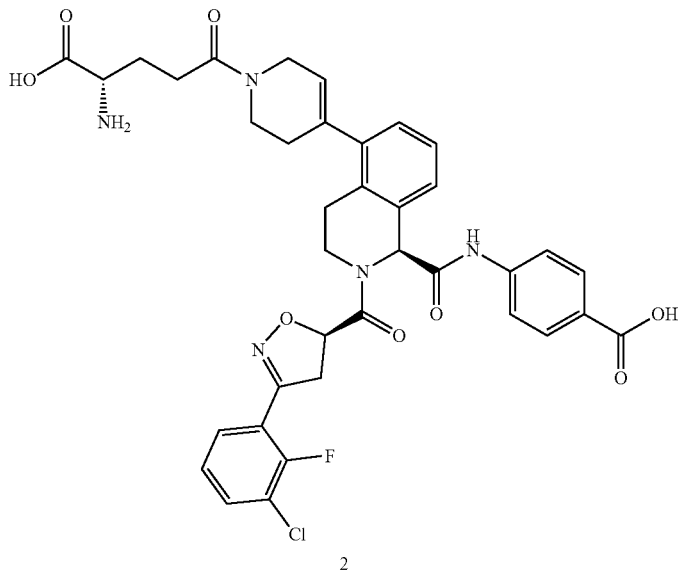

2

The formate of the title compound was obtained through procedures similar to Example 1, except that (S)-5-(tert-butoxy)-4-((tert-butoxycarbonyl) amino)-5-oxopentanoic acid was used in the first step of this Example instead of Boc-valine in step 5 of Example 1.

$^1$H NMR (400 MHz, DMSO-d$_6$) δ 10.88 (s, 1H), 8.16 (s, 1H), 7.87 (d, J=8.7 Hz, 2H), 7.77-7.65 (m, 4H), 7.58 (d, J=7.8 Hz, 1H), 7.32-7.26 (m, 2H), 7.12 (d, J=7.5 Hz, 1H), 5.80-5.62 (s, 3H), 4.28-4.16 (m, 1H), 3.89-3.61 (m, 7H), 3.26-2.99 (m, 5H), 2.47-2.33 (m, 4H), 1.89-1.85 (m, 3H), 1.92 (m, 1H).

MS m/z (ESI): 732 [M−H]$^+$

Example 3

4-((S)-5-(1-((S)-2-amino-4-carboxybutanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid

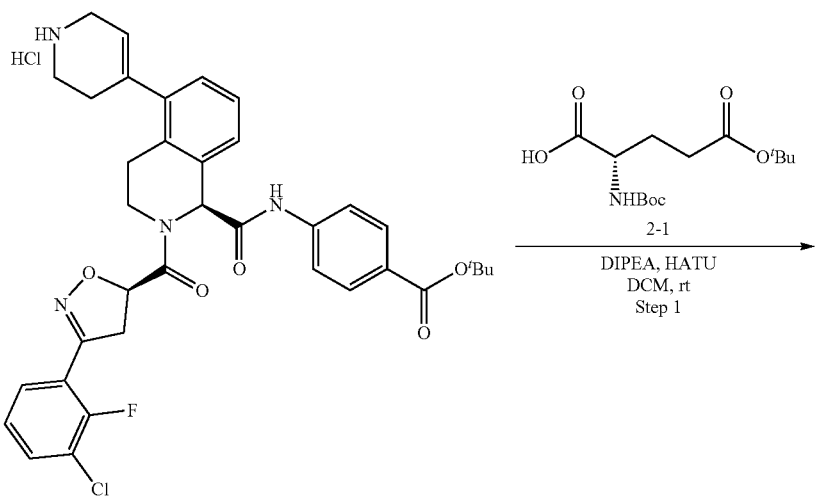

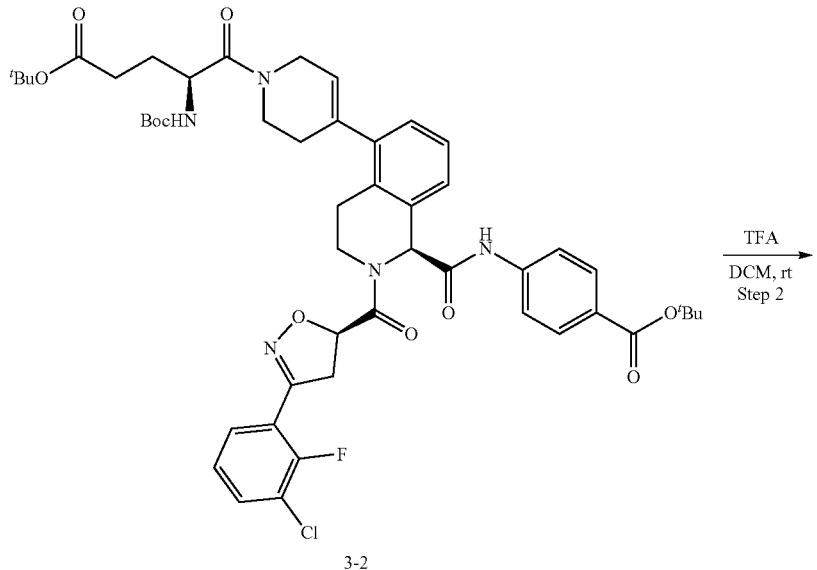
3-2
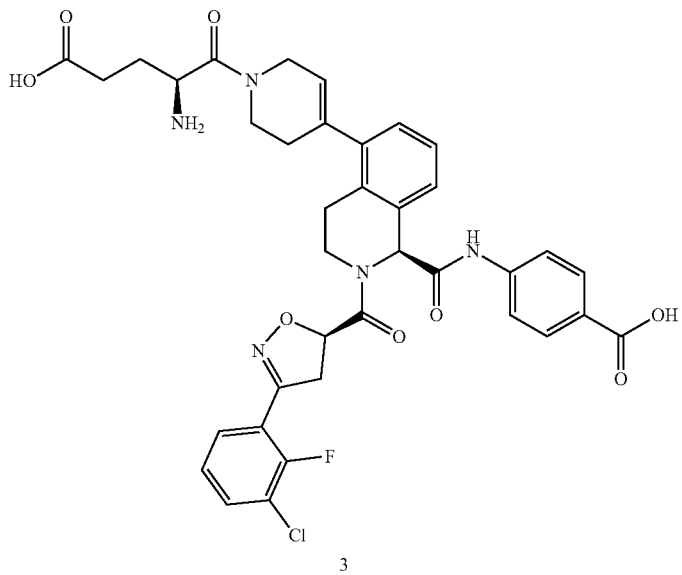
3
The formate of the title compound was obtained through procedures similar to Example 1, except that (S)-5-(tert-butoxy)-2-((tert-butoxycarbonyl) amino)-5-oxopentanoic acid was used in the first step of this Example instead of Boc-valine in step 5 of Example 1.
$^1$H NMR (400 MHz, DMSO-d$_6$) δ 10.91 (s, 1H), 8.15 (s, 1H), 7.86 (d, J=8.7 Hz, 2H), 7.76-7.66 (m, 4H), 7.57 (d, J=7.5 Hz, 1H), 7.32-7.25 (m, 2H), 7.11 (d, J=7.6 Hz, 1H), 5.81 (s, 1H), 5.78-5.69 (m, 1H), 5.64 (s, 1H), 4.24 (d, J=12.2 Hz, 1H), 3.89-3.84 (m, 1H), 3.67-3.61 (m, 6H), 3.13 (m, 3H), 3.02-2.99 (m, 2H), 2.47-2.33 (m, 4H), 2.09-2.04 (m, 3H), 1.92 (s, 1H).
MS m/z (ESI): 732 [M−H]$^+$

Example 4

4-((S)-5-(1-((S)-2-aminopropanoyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid

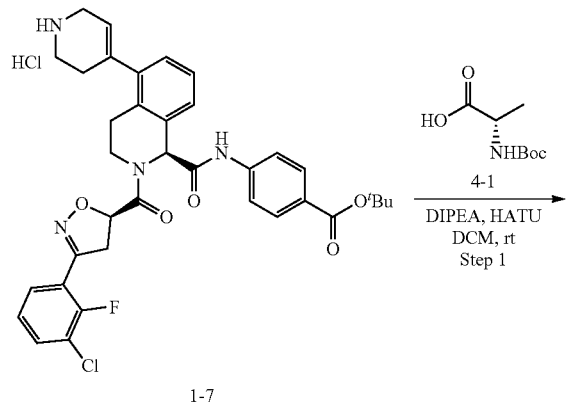

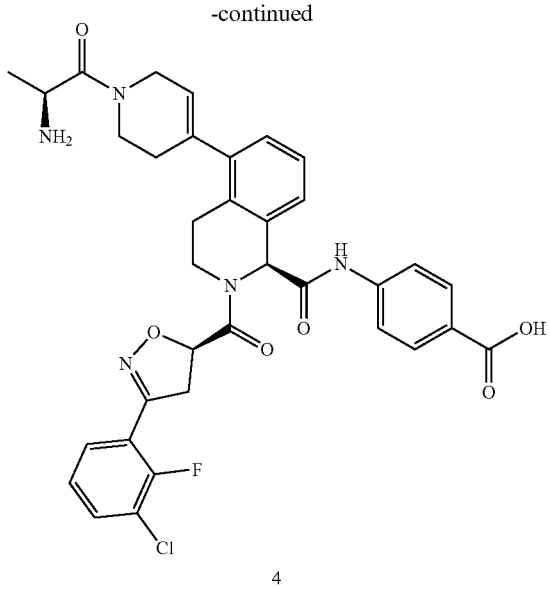

The formate of the title compound was obtained through procedures similar to Example 1, except that Boc-alanine was used in the first step of this Example instead of Boc-valine in step 5 of Example 1.

$^1$H NMR (400 MHz, DMSO-d$_6$) δ 10.83 (s, 1H), 8.15 (s, 1H), 7.86 (d, J=8.7 Hz, 2H), 7.76-7.68 (m, 2H), 7.66 (d, J=8.8 Hz, 2H), 7.55 (d, J=7.7 Hz, 1H), 7.33-7.25 (m, 2H), 7.10 (d, J=7.5 Hz, 1H), 5.80 (s, 1H), 5.76-5.72 (m, 1H), 5.62 (s, 1H), 4.28-4.16 (m, 1H), 3.89-3.94 (m, 1H), 3.77-3.62 (m, 7H), 3.26 (s, 3H), 3.18-2.99 (m, 2H), 1.54-1.43 (m, 2H), 1.17 (m, 3H).

MS m/z (ESI): 674 [M−H]$^+$

Example 5: 4-((S)-5-(1-(2-(((S)-5-amino-5-carboxypentyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid

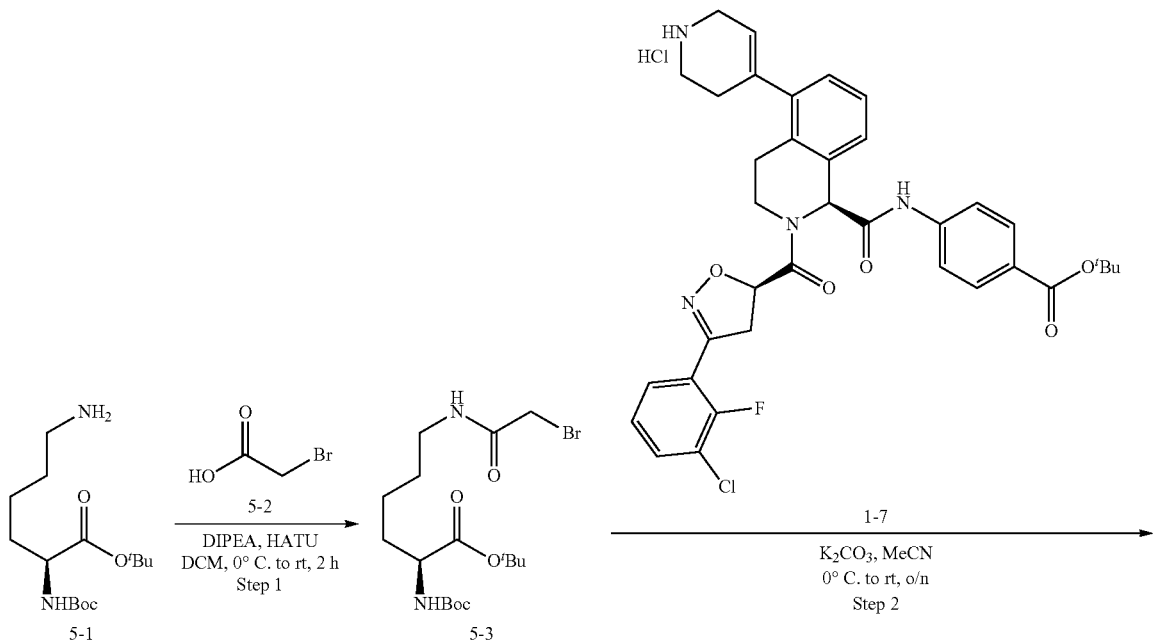

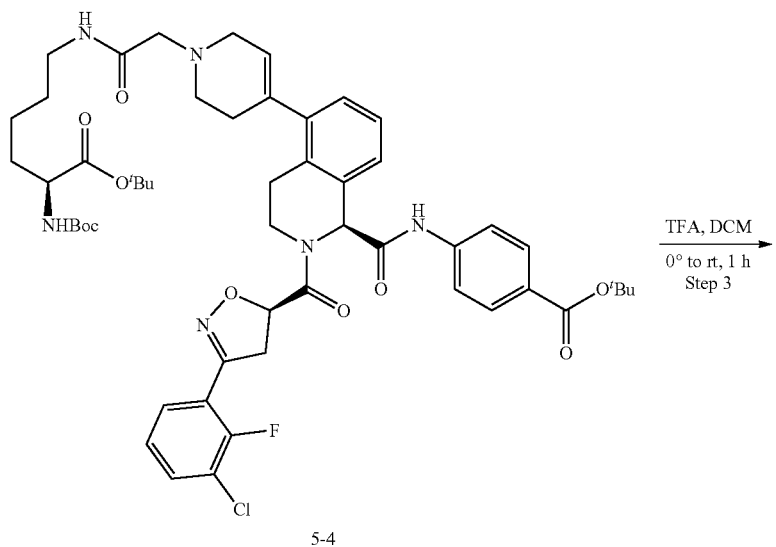

5-4

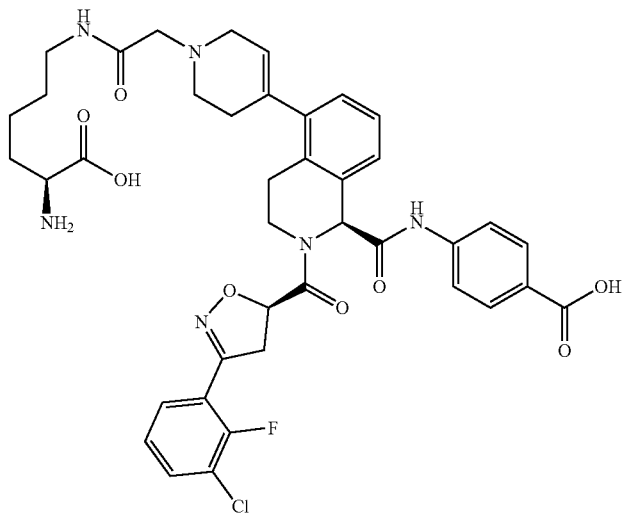

5

Step 1: Preparation of N⁶-(2-bromoacetyl)-N²-(tert-butoxycarbonyl)-L-lysine tert-butyl Ester (5-3)

Under condition of $N_2$, compound (tert-butoxycarbonyl)-L-lysine tert-butyl ester (5-1, 1.51 g, 5 mmol) was dissolved in DCM (10 mL). DIPEA (1.94 g, 15 mmol), HATU (2.85 g, 7.5 mmol) and 2-bromoacetic acid (5-2, 759 mg, 5.5 mmol) were added at 0° C. Then the reaction was warmed up to room temperature, and the reaction was monitored by LC-MS. After the completion of the reaction, water (5 mL) was added to quench the reaction. The reaction mixture was extracted with DCM (3×20 mL). The organic phase was concentrated and the residue obtained was separated by column chromatography to obtain the title compound (5-3, 1.15 g, yield: 54.3%).

MS m/z (ESI): 423 [M+H]⁺

Step 2: Preparation of 4-((S)-5-(1-(2-4(S)-6-(tert-butoxy)-5-((tert-butoxycarbonyl) amino)-6-oxohexyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid tert-butyl ester (5-4)

Compound 4-((S)-2-((R)-3-(3-chloro-2-fluorophenyl)-4,5-dihydroisoxazole-5-carbonyl)-5-(1,2,3,6-tetrahydropyridin-4-yl)-1,2,3,4-tetrahydroisoquinoline-1-carboxamido) benzoic acid tert-butyl ester hydrochloride (1-7, 203 mg, 0.31 mmol) and N⁶-(2-bromoacetyl)-N²-(tert-butoxycarbonyl)-L-lysine tert-butyl ester (5-3, 130 mg, 0.31 mmol) were dissolved in MeCN (5 mL). Potassium carbonate (86 mg, 0.62 mmol) was added in portions at 0° C. Then the reaction was warmed up to room temperature. The reaction was monitored by LC-MS. After completion of the reaction, water (5 mL) was added to quench the reaction. The mixture was extracted with ethyl acetate (3×10 mL). The organic phase was concentrated and the residue obtained was separated by column chromatography to obtain the title compound (5-4, 242 mg, yield: 78.1%).

MS m/z (ESI): 1001 [M+H]$^+$

Step 3: Preparation of 4-((S)-5-(1-(2-4(S)-5-amino-5-carboxypentyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid Compound ((S)-5-(1-(2-(((S)-6-(tert-butoxy)-5-((tert-butoxycarbonyl)amino)-6-oxohexyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid tert-butyl ester (5-4, 242 mg, 0.24 mmol) was dissolved in DCM (2 mL), TFA (2 mL) was slowly added dropwise at 0° C.

Then the reaction was warmed up to room temperature. The reaction was monitored by LC-MS. After the completion of the reaction, the excess TFA and solvent were removed under reduced pressure, and the obtained residue was separated by HPLC (formic acid/methanol/water) to obtain the formate of the title compound (49 mg, yield: 25.9%).

$^1$H NMR (400 MHz, DMSO-d$_6$) δ 10.90 (s, 1H), 8.25 (s, 1H), 7.90 (d, J=8.7 Hz, 2H), 7.76-7.64 (m, 5H), 7.57 (d, J=7.6 Hz, 1H), 7.33-7.25 (m, 2H), 7.13 (d, J=7.6 Hz, 1H), 5.83 (s, 1H), 5.82-5.75 (m, 1H), 5.62-5.41 (m, 2H), 4.28-4.16 (m, 2H), 3.89-3.94 (m, 1H), 3.77-3.65 (m, 5H), 3.18-2.97 (m, 3H), 2.72 (s, 3H), 2.47-2.20 (m, 4H), 2.01 (m, 1H), 1.72-1.60 (m, 2H), 1.59-1.19 (m, 5H).

MS m/z (ESI): 790 [M+H]$^+$

Example 6: 4-((S)-5-(1-(2-(((R)-5-amino-1-carboxypentyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid

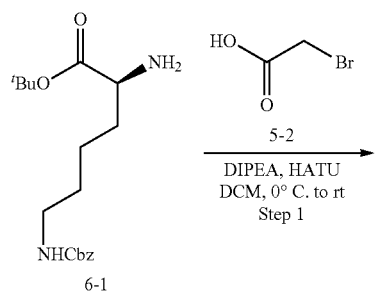

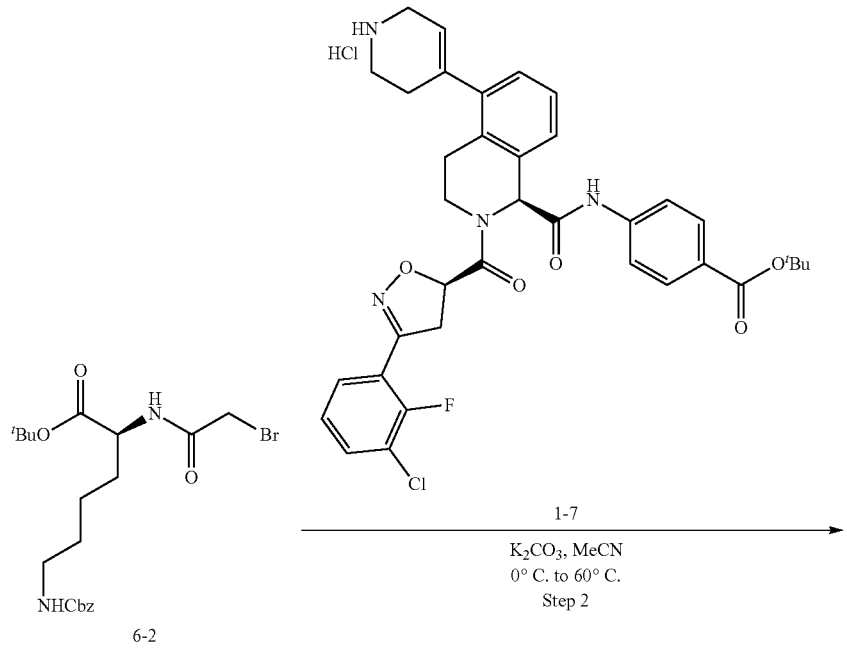

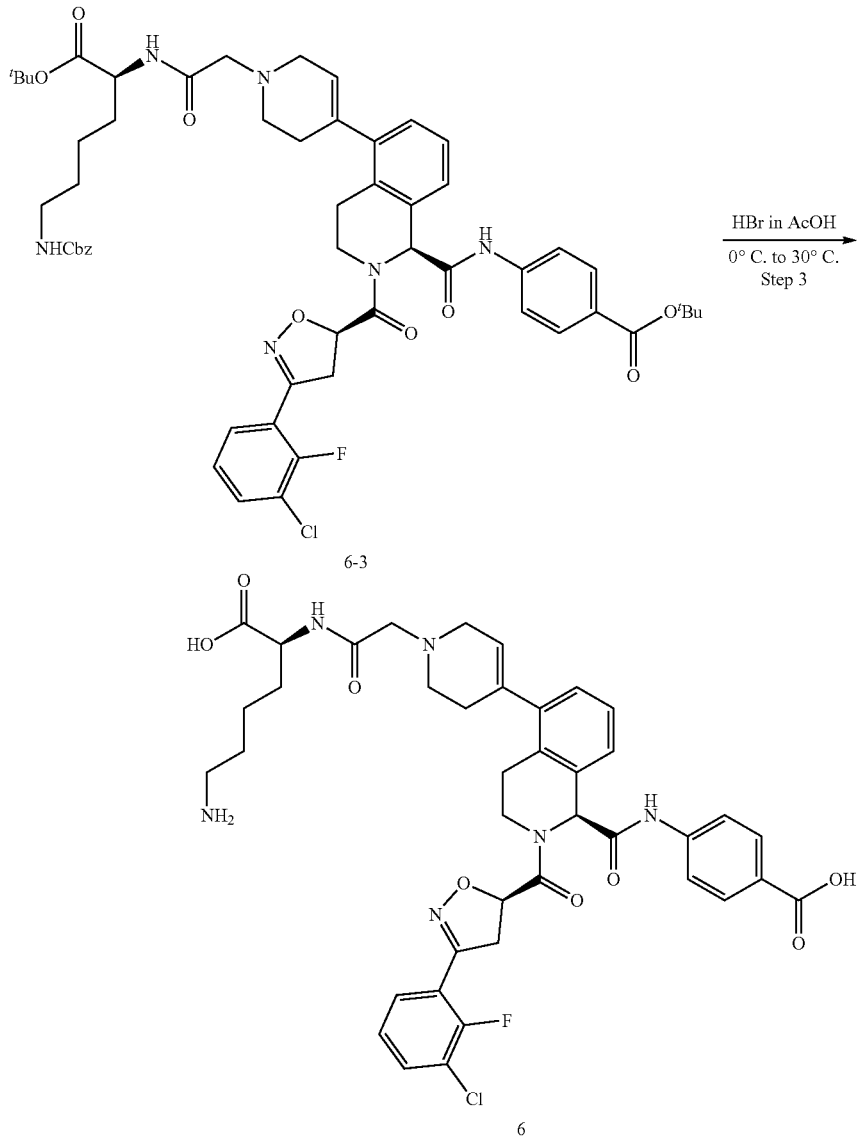

Step 1: Preparation of N⁶-((Benzyloxy) Carbonyl)-N²-(2-Bromoacetyl)-L-Lysine Tert-Butyl Ester (6-2)

Under condition of N$_2$, compound N⁶-((benzyloxy) carbonyl)-L-lysine tert-butyl ester (6-1, 1.68 g, 5 mmol) was dissolved in DCM (10 mL). DIPEA (1.94 g, 15 mmol), HATU (2.85 g, 7.5 mmol) and 2-bromoacetic acid (5-2, 759 mg, 5.5 mmol) were added at 0° C. Then the reaction was warmed up to room temperature, and the reaction was monitored by LC-MS. After the completion of the reaction, water (5 mL) was added to quench the reaction, reaction mixture is extracted with DCM (3×20 mL). The organic phase was concentrated and the residue obtained was separated by column chromatography to obtain the title compound (6-2, 1.38 g, yield: 60.5%).

MS m/z (ESI): 457 [M+H]⁺

Step 2: Preparation of ((S)-5-(1-(2-(((S)-6-(((benzyloxy) carbonyl) amino)-1-(tert-butoxy)-1-oxohexan-2-carboxylic acid tert-butyl ester) amino)-2-oxoethyl)-1,2,3,6-tetrahydropyridin-4-yl)-2-4R)-3-(3-chloro-2-fluorophenyl)-4,5-dihydroisoxazole-5-carbonyl)-1,2,3,4-tetrahydroisoquinoline-1-carboxamido)benzoic acid methyl ester (6-3)

Compound 4-((S)-2-((R)-3-(3-chloro-2-fluorophenyl)-4,5-dihydroisoxazole-5-carbonyl)-5-(1,2,3,6-tetrahydropyridin-4-yl)-1,2,3,4-tetrahydroisoquinoline-1-carboxamido) benzoic acid tert-butyl ester hydrochloride (1-7, 203 mg, 0.31 mmol) and N⁶-(2-bromoacetyl)-N²-(tert-butoxycarbonyl)-L-lysine tert-butyl ester (6-2, 142 mg, 0.31 mmol) were dissolved in MeCN (5 mL). Potassium carbonate (86 mg, 0.62 mmol) was added in portions at 0° C. Then the reaction was warmed up to room temperature. The reaction was monitored by LC-MS. After completion of the reaction, water (5 mL) was added to quench the reaction. The mixture was extracted with ethyl acetate (3×10 mL). The organic phase was concentrated and the residue obtained was separated by column chromatography to obtain the title compound (6-3, 238 mg, yield: 74.3%).

MS m/z (ESI): 1035 [M+H]$^+$

Step 3: Preparation of 4-((S)-5-(1-(2-4(R)-5-amino-1-carboxypentyl) amino)-2-oxoethyl)-1,2,3,6-tetrahydropyridin-4-yl)-2-((R)-3-(3-chloro-2-fluorophenyl)-4,5-di hydroisoxazole-5-carbonyl)-1,2,3,4-tetrahydroisoquinoline-1-carboxamido)benzoic acid Compound ((S)-5-(1-(2-((S)-6-(((benzyloxy) carbonyl) amino)-1-(tert-butoxy)-1-oxohexan-2-carboxylic acid tert-butyl ester) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid methyl ester (6-3, 364 mg, 0.35 mmol) was dissolved in the acetic acid solution of HBr (2 mL, 33 wt. %) at 0° C., then the reaction was warmed up to 30° C. The reaction was monitored by LC-MS. After the completion of the reaction, excess ethyl ether was added to the system until no solid precipitated. The obtained solid was filtered, the filtered cake was washed with ethyl ether (3×5 mL). The obtained solid was separated by HPLC (formic acid/methanol/water) to obtain the formate of the title compound (61 mg, yield: 21.8%).

MS m/z (ESI): 790 [M−H]$^+$

Example 7

4-(5-(1-((S)-2-amino-propanoyl)-1,2,3,6-tetrahydropyridin-4-yl)-2-((E)-3-(3-chloro-2-fluoro-6-(phenyl) acryloyl)-1,2,3,4-tetrahydroisoquinoline-1-carboxamido) benzoic acid

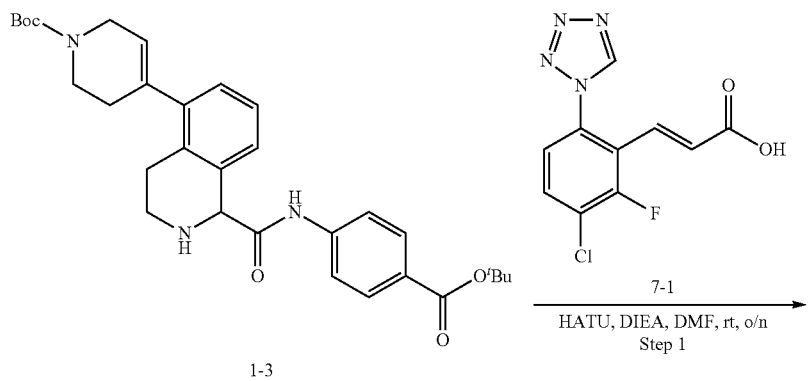

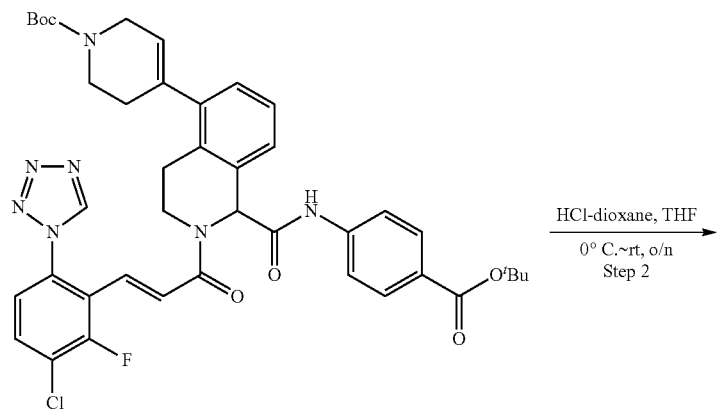

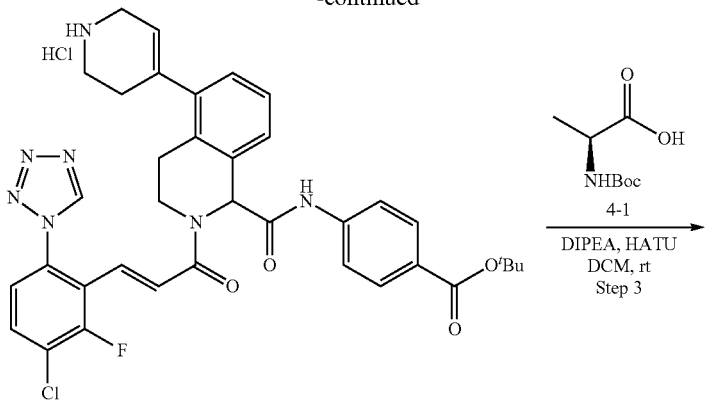

7-3

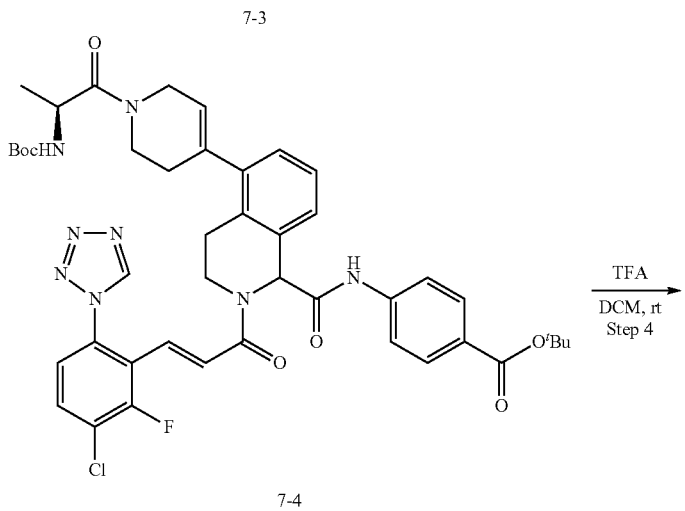

7-4

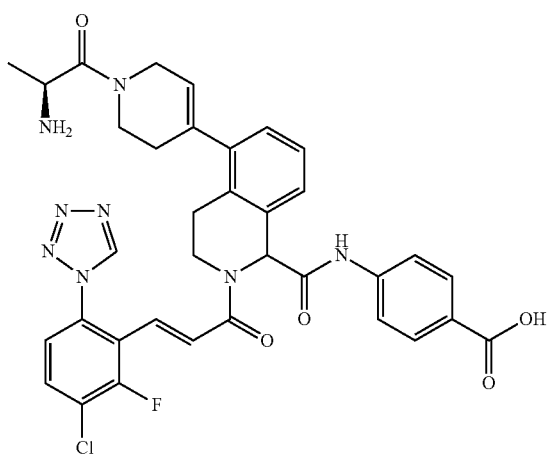

7-a

The formate of the title compound was obtained through procedures similar to Example 4, except that (E)-3-(3-chloro-2-fluoro-6-(1H-tetrazol-1-yl) phenyl) acrylic acid was used in the first step of this Example instead of (R)-3-(3-chloro-2-fluorophenyl)-4,5-dihydroisoxazole-5-carboxylic acid in step 3 of Example 1

MS m/z (ESI): 699 [M+H]+

Example 8: 4-((S)-5-(1-(2-(((S)-5-Amino-5-carboxypentyl) amino)-2-oxoethyl)-1,2,3,6-tetrahydropyridin-4-yl)-2-((R)-3-(3-chloro-2-fluorophenyl)-4,5-dihydroisoxazole-5-carbonyl)-1,2,3,4-tetrahydroisoquinoline-1-carboxamido)benzoic acid To 50 ml of aqueous solution of 20% ethanol, formate of compound 5 (2.5 g, 2.99 mmol) obtained in example 5 was added. Formic acid solution (in 20% ethanol) was added under stirring. The pH was adjusted to 3.2 until complete dissolution (as long as complete dissolution is achieved). After 10 min, saturated sodium hydrogen carbonate solution (in 20% ethanol) was added slowly dropwise. The pH was adjusted to 6.05 (between 6.0-6.1). A large amount of precipitated white solid was observed. After stirring for 1 h, the solids were filtered, dried, and collected. The title compound was obtained (1.8 g, yield: 76.2%).

$^1$H NMR (400 MHz, DMSO-$d_6$) δ 10.82 (s, 1H), 7.85-7.83 (d, J=8.6 Hz, 2H), 7.73-7.63 (m, 5H), 7.55-7.53 (d, J=7.6 Hz, 1H), 7.33-7.21 (m, 2H), 7.11-7.09 (d, J=7.4 Hz, 1H), 5.79 (s, 1H), 5.77-5.74 (m, 1H), 5.56 (s, 1H), 4.26-4.23 (s, 1H), 3.88-3.69 (m, 4H), 3.14-3.04 (m, 9H), 2.68 (s, 2H), 2.36-2.32 (m, 2H), 1.72-1.33 (m, 6H).

MS m/z (ESI): 790 [M+H]$^+$

Reference compound in the experimental examples is BMS-962212:

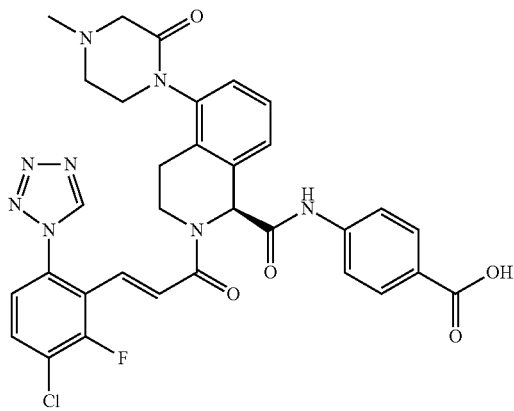 [SMILES: CN1CCN(c2cccc3c2CCN(C(=O)/C=C/c2c(-n4cnnn4)ccc(Cl)c2F)[C@@H]3C(=O)Nc2ccc(C(=O)O)cc2)C(=O)C1]

Experimental Example 1. Inhibition of Coagulation Factor XIa

The following procedures can be used to determine the in vitro inhibition of human coagulation factor XIa by the compound of the present disclosure, as indicated by IC$_{50}$.

Reagents:
Enzyme: human coagulation factor XIa; manufacturer: Haemtech;
Substrate: Boc-Ile-Glu-Gly-Arg-AMC Acetate salt; manufacturer: Bachem;
Reaction buffer: 50 mM HEPES, 145 mM NaCl, 5 mM KCl, 0.1% BSA, pH 7.4;
Detection Method:

The test compounds were dissolved in reaction buffer at different concentrations. 4 μl of coagulation factor XIa and 4 μl of the test compound were added to a 384 well plate, incubated at room temperature for 10 minutes after mixed thoroughly, and then 4 μl of substrate was added to initiate the reaction. For reading fluorescence signal value, enzyme kinetic mode was used. The wavelength of excitation light was selected to be 380 nm, and the wavelength of emission light was selected to be 460 nm. Read once per 30 seconds, and continuously read 20 cycles. Linear regression analysis of signal value-time was performed during the linear reaction period, and the slope was the reaction rate, and the enzyme activity inhibition rate was calculated according to the following formula. The half inhibitory concentration IC$_{50}$ values of the compound were fitted using GraphPad Prism 5 software, and results are shown in Table 1.

Inhibition rate %=$(V_0-V_i)/(V_0-V_{blank})\times 100$.

In the formula: $V_0$ is the reaction rate of the control well (using the same volume of reaction buffer without adding test compound), $V_i$ is the reaction rate of test compound, $V_{blank}$ is a blank well (using the same volume of reaction buffer without adding either enzyme or test compound).

TABLE 1

| Inhibition of compounds to coagulation factor XIa | |
|---|---|
| Example No. | IC$_{50}$ (nM) |
| 1 | 0.33 ± 0.06 |
| 2 | 0.21 ± 0.02 |
| 3 | 0.29 ± 0.04 |
| 4 | 0.85 ± 0.03 |
| 5 | 0.16 ± 0.02 |

As can be seen from Table 1, the compound of the present disclosure has a significant inhibitory effect on coagulation factor XIa Experimental Example 2. Determination of Inhibition of Coagulation Factor VIIa, Coagulation Factor Xa Reagents:
Enzyme: human coagulation factor VIIa; manufacturer: Haematologic Technologies;
Substrate: Boc-VPR-AMC; R&D System;
Tissue factor: tissue factor F3; manufacturer: Sino Biological;
Enzyme: human coagulation factor Xa; manufacturer: R&D System;
Substrate: Mca-RPKPVE-Nval-WRK(Dnp)-NH$_2$; manufacturer: R&D;
Determination of Inhibition of Factor VIIa:

The test compounds were dissolved in assay buffer (50 mM Hepes, 150 mM NaCl, 5 mM CaCl$_2$, pH 7.4) at a final concentration of 10 μM and 1 μM. Coagulation factor VIIa and tissue factor were mixed at an equimolar concentration. After incubation at 37° C. for 15 minutes, the test compound was further added. Incubation was conducted at room temperature for 10 minutes. Then the substrate (Boc-VPR-AMC) was added to initiate the reaction. For reading fluorescence signal value, enzyme kinetic mode was used. The wavelength of excitation light was 380 nm, and the wavelength of emission light was 460 nm. The IC$_{50}$ was calculated in a similar manner to experimental Example 1.

Determination of inhibition of factor Xa:
The test compounds were dissolved in assay buffer (50 mM Tris, 150 mM NaCl, 10 mM CaCl$_2$, 0.05% Brij35, pH 7.5) at a final concentration of 10 μM and 1 μM. Coagulation factor Xa and test compound were added to the well plate, and incubation was conducted at room temperature for 10 minutes after mixed thoroughly. The substrate (Mca-RPKPVE-Nval-WRK(Dnp)-NH$_2$) was added to initiate the reaction. For reading fluorescence signal value, enzyme kinetic mode was used. The wavelength of excitation light was 320 nm, and the wavelength of emission light was 400 nm. The IC$_{50}$ was calculated in a manner similar to experimental Example 1.

TABLE 2

Inhibition of test compound to coagulation factor Xa and VIIa

| Example No. | Xa IC$_{50}$ (M) | VIIa IC$_{50}$ (μM) |
|---|---|---|
| 5 | About 10 | >10 |

The test compound of the present disclosure (for example compound of Example 5) has no significant inhibitory effect on coagulation factor Xa and coagulation factor VIIa. As can be seen from tables 1-2, the compound of the present disclosure (for example compound of Example 5) has a good selectivity. While having a high affinity for coagulation factor XIa, the compound of the present disclosure does not inhibit coagulation factor Xa or VIIa.

Experimental Example 3. Effect of Compounds on Coagulation In Vitro

Reagent:
aPTT reagent (purchased from Sysmex);
PT reagent (purchased from Sysmex);
The coagulation pathway includes the extrinsic coagulation pathway and the intrinsic coagulation pathway. The parameter associated with the extrinsic coagulation pathway is prothrombin time, expressed as PT; the parameter associated with the intrinsic coagulation pathway is activated partial thromboplatin time, expressed as aPTT.
Detection methods of aPTT (activated partial thromboplatin time) and PT (prothrombin time):
After anticoagulation, blood of different species (rabbit, human) was subjected to centrifugation. The upper layer of plasma was collected and divided into several aliquots. The test compounds were added to make the final concentration of test compound to be 10$_N$M. Incubation was conducted at 37° C. after mixed thoroughly. Then the samples were put into a coagulation analyzer (Sysmex CA1500, Sysmex, Japan) for the aPTT and PT assays. Blank plasma (without test compound) was used as a reference, and the ratio values of aPTT and PT of all samples and blank plasmas were analyzed, the results are shown in table 3.

TABLE 3

Effect of compound of example 5 on aPTT and PT in different species (n = 3)

|  | Rabbit | Human |
|---|---|---|
| Ratio of aPTT to that of blank plasma | 1.84 | 2.95 |
| Ratio of PT to that of blank plasma | 1.00 | 1.03 |

As shown in table 3, compared with blank plasma without addition of test compound, the aPTT was significantly prolonged after addition of the compound of example 5. This indicates that effect of intrinsic coagulation can be achieved through the selective inhibition of XIa of the compound of the present disclosure. Compared with blank plasma without addition of test compound, there is no significant change in the PT value after addition of the compound of example 5 of the present disclosure, wherein the PT value is associated with the extrinsic pathway coagulation. The compound of the present disclosure had no effect on the extrinsic coagulation pathway.

Experimental Example 4. Solubility Test

The test compound was dissolved in a buffer (pH 7.4) at room temperature until the solution reached supersaturation. The solution was shaken at 25° C. by a constant temperature mixer for 4 hours, filtered through a 0.45 μm aqueous membrane filter, and the concentration was measured by UPLC. 1 mg of the test compound was accurately weighed, and dissolved in 10 mL volumetric flask as the reference substance. The reference substance was measured using the same process. The solubility of the test compound was calculated according to external standard process, and the results are shown in table 4.

TABLE 4

Solubilities of compounds in pH 7.4 buffer

| Example No. | Solubility (mg/ml) |
|---|---|
| 5 | 10.8 |
| Reference compound (BMS-962212) | 1.5$^a$ |

$^a$Data according to the reference (J. Med. Chem. 2017, 60, 9703-9723).

As shown in table 4, the compounds of the present disclosure have good solubilities in pH 7.4 buffer.

Experimental Example 5. Pharmacokinetics (PK) Study on Rats, Rabbits and Beagle Dogs Pharmacokinetics characteristics were examined by administering compound of the present disclosure and the reference compound (BMS-962212) to male SD rats through intravenous injection (IV). Blood was collected at various time points after administration. The blood was anticoagulated with EDTA-K2. Plasma samples were obtained by centrifugation within 30 min after blood collection, and retained at −80° C. The plasma samples were processed to precipitate the proteins and then analyzed by LC-MS/MS.

The pharmacokinetic parameters were calculated using WinNonlin 6.3 software by employing a non-compartmental model. The results are shown in table 5.

TABLE 5

Pharmacokinetic parameters data in rats

| Example No. | Dosage (mg/kg) | AUC$_{INF}$ (h * ng/ml) | AUC$_{last}$ (h * ng/ml) | Cl (ml/min/kg) | C$_{max}$ (ng/ml) | T$_{1/2}$ (h) |
|---|---|---|---|---|---|---|
| 5 | 1 | 2892 ± 473 | 2886 ± 473 | 5.88 ± 1.07 | 2993 ± 629 | 0.78 ± 0.06 |
| Reference compound | 5 | 4090 ± 654 | 4089 ± 654 | 20.7 ± 2.7 | 11120 ± 1854 | 0.19 ± 0.03 |

Pharmacokinetics properties were examined by administering compound of the present disclosure and the reference compound (BMS-962212) to male rabbits through intravenous injection (IV). Blood was collected at various time points after administration. The blood was anticoagulated with EDTA-K2. Plasma samples were obtained by centrifugation, and retained at −80° C. The plasma samples were processed to precipitate the proteins and then analyzed by LC-MS/MS.

The pharmacokinetic parameters were calculated using WinNonlin 6.3 software by employing a non-compartmental model. The results are shown in table 6.

TABLE 6

Pharmacokinetic data in rabbits

| Example No. | Dosage (mg/kg) | $V_d$ (l/kg) | $AUC_{INF}$ (h * ng/ml) | $AUC_{last}$ (h * ng/ml) | Cl (ml/min/kg) | $C_{max}$ (ng/ml) | $T_{1/2}$ (h) |
|---|---|---|---|---|---|---|---|
| 5 | 1 | 0.30 ± 0.09 | 5735 ± 2268 | 5731 ± 2267 | 3.18 ± 1.06 | 6947 ± 1904 | 1.14 ± 0.26 |
| Reference compound | 1 | 1.28 ± 0.28 | 484 ± 38 | 476 ± 35 | 34.6 ± 2.8 | 1467 ± 145 | 0.43 ± 0.11 |

Pharmacokinetics properties were examined by administering compound of the present disclosure and the reference compound (BMS-962212) to Beagle dog through intravenous injection (IV). Blood was collected at various time points after administration. The blood was anticoagulated with EDTA-K$_2$. Plasma samples were obtained by centrifugation, and retained at −80° C. The plasma samples were processed to precipitate the proteins and then analyzed by LC-MS/MS.

The pharmacokinetic parameters were calculated using WinNonlin 6.3 software by employing a non-compartmental model. The results are shown in table 7.

TABLE 7

Pharmacokinetic data in Beagle dogs

| Example No. | Dosage (mg/kg) | $V_d$ (l/kg) | $AUC_{INF}$ (h * ng/ml) | $AUC_{last}$ (h * ng/ml) | Cl (ml/min/kg) | $C_{max}$ (ng/ml) | $T_{1/2}$ (h) |
|---|---|---|---|---|---|---|---|
| 5 | 0.5 | 0.24 ± 0.02 | 18118 ± 683 | 17243 ± 370 | 0.46 ± 0.02 | 3947 ± 808 | 6.02 ± 0.80 |
| Reference compound | 0.5 | 0.71 ± 0.04 | 846 ± 80 | 846 ± 80 | 9.91 ± 0.94 | 1477 ± 40 | 0.83 ± 0.05 |

As can be seen from table 5, after administrating intravenously 1 mg/kg of the compound of example 5 and 5 mg/kg of the reference compound to rat, and normalizing the dosage and performing comparison, it is found that the $AUC_{last}$ of compound of example 5 in vivo in rat plasma was 3.53 times that of the reference compound. And the $C_{max}$ was 1.35 times that of the reference compound. The $T_{1/2}$ was 4.11 times that of the reference compound. The pharmacokinetic properties of the compound of example 5 were superior over the reference compound in rats.

As can be seen from table 6, after intravenous administration of 1 mg/kg of the compound of example 5 and 1 mg/kg of the reference compound to rabbit, the $AUC_{last}$ of compound of example 5 in rabbits was 12.04 times that of the reference compound. And the $C_{max}$ was 4.74 times that of the reference compound. The $T_{1/2}$ was 2.65 times that of the reference compound. The pharmacokinetic properties of the compound of example 5 in rabbits were superior over the reference compound. Under the same dosage, the apparent volume of distribution of TM-5 is smaller, namely being 23% of that of the reference compound, suggesting that the compound of example 5 was more likely to be distributed in the blood circulation than the reference compound.

As can be seen from table 7, after administration of 0.5 mg/kg of the compound of example 5 and 0.5 mg/kg of the reference compound, the $AUC_{last}$ of compound of example 5 in Beagle dogs was 20.38 times that of the reference compound. And the $C_{max}$ was 2.67 times that of the reference compound. The $T_{1/2}$ was 7.25 times that of the reference compound. The pharmacokinetic properties of the compound of example 5 were superior over the reference compound in Beagle dogs. Under the same dosage, the apparent volume of distribution of the compound of example 5 is smaller, namely being 34% of that of the reference compound, suggesting that the compound of example 5 was more likely to be distributed in the blood circulation than the reference compound.

The present inventors have surprisingly found that, compared with the reference compound, the compounds of the present disclosure have significant advantages in pharmacokinetics. Coagulation factor XIa is an extracellular target in blood, and the compounds of the present disclosure are more primarily distributed in the blood. Therefore, the amount entering other tissues and cells is lower, and thereby the toxicity and side effects can be reduced.

Experimental Example 6. Toxicity Study of Single and Repeated Dose of SD Rats

Compound of example 5 and the reference compound were administered to SD rats through intravenous infusion, and the toxicity reaction after single dose and repeated dose was examined and compared.

The clinical observation was carried out for 7 days after a single dose, and the body weight of the animals were measured. On the 8th day, blood samples were taken after anesthesia for detection of hematology, blood biochemistry, coagulation and other indicators. Observation was also conducted by gross anatomy. The main experimental results are summarized in table 8.

TABLE 8

Result of the single dose study of compound of example 5 and the reference compound

| Example No. | Administration dosage (mg/kg) | Administration route | Single dose toxicity study in SD rats |
|---|---|---|---|
| 5 | 50, 75, 100, 150, 200 | Intravenous infusion (2 ml/min) | No abnormality was found in each dosage group after administration; Maximum tolerated dose (MTD) ≥200 mg/kg |

87

TABLE 8-continued

Result of the single dose study of compound of example 5 and the reference compound

| Example No. | Administration dosage (mg/kg) | Administration route | Single dose toxicity study in SD rats |
|---|---|---|---|
| Reference compound | 50, 70, 75 | Intravenous infusion (2 ml/min) | No abnormality was observed after administration of 50 mg/kg; obviously hypoactive behavior, lying on the stomach, and other adverse reactions observed at 70 mg/kg; Death of the animals were observed after administration at 75 mg/kg. MTD = 70 mg/kg |

The administration was repeated daily for 14 days, while clinical observation, body weight and food intake were recorded. On the 15th day, blood samples were taken after anesthesia for detection of hematology, blood biochemistry, coagulation and other indicators. Observation by gross anatomy and examination of histopathology were also conducted. The main experimental results are summarized in table 9.

TABLE 9

Result of repeated dose toxicity study of compound of example 5 and the reference compound

| Example No. | Administration dosage (mg/kg) | Administration route | Repeated dose toxicity study in SD rats |
|---|---|---|---|
| 5 | 20, 60, 150 | Intravenous infusion | The kidney had obvious lesions at the end of administration in high dosage group of 150 mg/kg, indicating that kidney is a toxic target organ under high dosage. No abnormality was observed in the remaining dosing groups. No-observed-adverse-effect level (NOAEL) = 60 mg/kg |
| Reference compound | 60 | Intravenous infusion | Significant weight loss during administration in female animals. Two females died on the 10th and 12th day of the administration NOAEL <60 mg/kg |

As can be seen from table 8 and table 9, in the single dose toxicity study in rats, the tolerated dose of the compound of Example 5 was superior over the reference compound. In the repeated dose toxicity study, the safety of the compound of Example 5 is also clearly superior over the reference compound.

The inventors have surprisingly found that, the compounds of the present disclosure have significant advantages in toxicology, and have improved safety.

In conclusion, the compounds of the present disclosure have high activities, high blood exposure and lower in vivo toxicity, and have significant advantages over the prior art.

88

The invention claimed is:

1. A compound or a pharmaceutically acceptable salt, stereoisomer, solvate, isotopically labeled compound, or prodrug thereof, wherein the compound has the structure of formula (I):

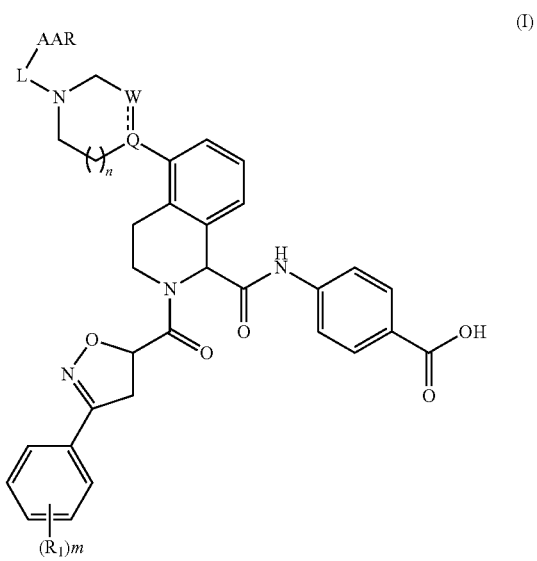

wherein:

" $\rlap{=}$ " represents a single bond or a double bond;

each $R_1$, at each occurrence, is independently selected from the group consisting of halogen, halo $C_{1-6}$ alkyl, nitro, and cyano;

W is selected from the group consisting of $CR_2$, $CR_{2a}R_{2b}$ and $C(=O)$;

Q is selected from the group consisting of N, C and $CR_3$;

each $R_2$, $R_{2a}$, $R_{2b}$ and $R_3$ is independently selected from the group consisting of H and $C_{1-6}$ alkyl;

L is selected from the group consisting of chemical bond, $C_{1-4}$ alkylene, and a bivalent radical formed by any combination of 1-4 groups selected from the group consisting of —$CH_2$—, —$C(=O)$— and —NH—;

AAR is selected from the group consisting of

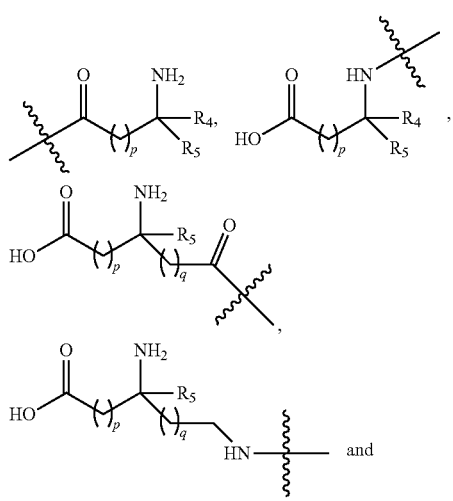

-continued

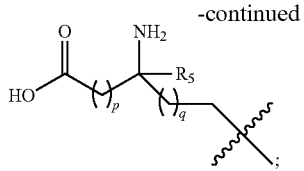

wherein
R₄ is selected from the group consisting of H and C$_{1-6}$ alkyl, wherein the alkyl is optionally substituted with 1, 2 or 3 groups selected from the group consisting of OR$_x$, NR$_x$R$_y$ and COOR$_x$;
R₅ is selected from the group consisting of H and C$_{1-6}$ alkyl;
each R$_x$ and R$_y$, at each occurrence, is independently selected from the group consisting of H and C$_{1-6}$ alkyl;
p is 0 or 1;
q is 0, 1, 2, 3 or 4;
m is 1, 2, 3, 4 or 5;
n is 0, 1, 2, 3, 4 or 5.

2. The compound of claim 1 or the pharmaceutically acceptable salt, stereoisomer, solvate, isotopically labeled compound, or prodrug thereof, wherein:
each R₁, at each occurrence, is independently selected from the group consisting of fluorine, chlorine, bromine and cyano.

3. The compound of claim 1 or the pharmaceutically acceptable salt, stereoisomer, solvate, isotopically labeled compound, or prodrug thereof, wherein:
L is selected from the group consisting of chemical bond, methylene, ethylene, —CH₂—NH—, —NH—C(=O)— and —C(=O)—CH₂—.

4. The compound of claim 1 or the pharmaceutically acceptable salt, stereoisomer, solvate, isotopically labeled compound, or prodrug thereof, wherein:
AAR is selected from the group consisting of

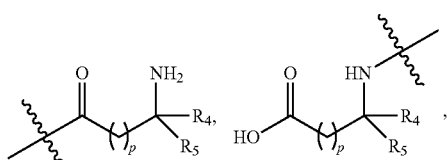

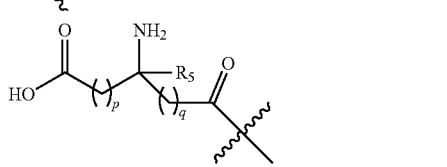

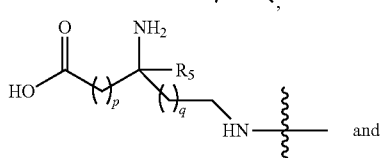

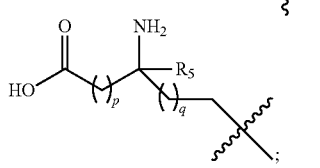

wherein
p is 0, and
R₄ is C$_{3-6}$ alkyl, wherein the alkyl is optionally substituted with 1 or 2 groups selected from the group consisting of OH, NH₂ and COOH; or R₄ is —CH₂CH₂COOH;
R₅ is H;
q is 2, 3 or 4;
or
p is 1, and
R₄ is C$_{2-6}$ alkyl, wherein the alkyl is optionally substituted with 1 or 2 groups selected from the group consisting of OH, NH₂ and COOH; or R₄ is —CH₂COOH;
R₅ is H;
q is 1, 2, 3 or 4.

5. The compound of claim 1 or the pharmaceutically acceptable salt, stereoisomer, solvate, isotopically labeled compound, or prodrug thereof, wherein:
m is 2, 3, 4 or 5;
n is 0, 1 or 2.

6. The compound of claim 1 or the pharmaceutically acceptable salt, stereoisomer, solvate, isotopically labeled compound, or prodrug thereof, wherein
R₅ is H; p is 0.

7. The compound of claim 1 or the pharmaceutically acceptable salt, stereoisomer, solvate, isotopically labeled compound, or prodrug thereof, wherein,
AAR is selected from the group consisting of:

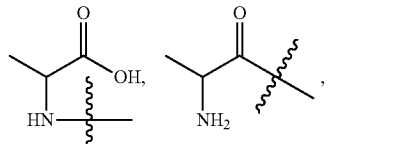

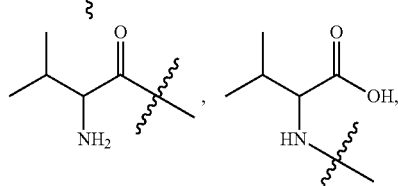

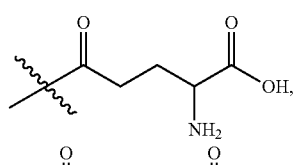

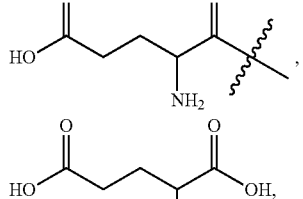

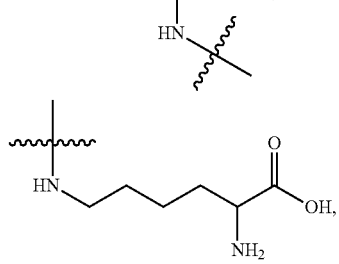

91
-continued

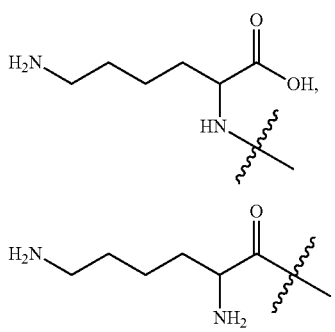

8. The compound of claim 1 or a pharmaceutically acceptable salt, stereoisomer, solvate, isotopically labeled compound, or prodrug thereof, wherein, -L-AAR is selected from the group consisting of:

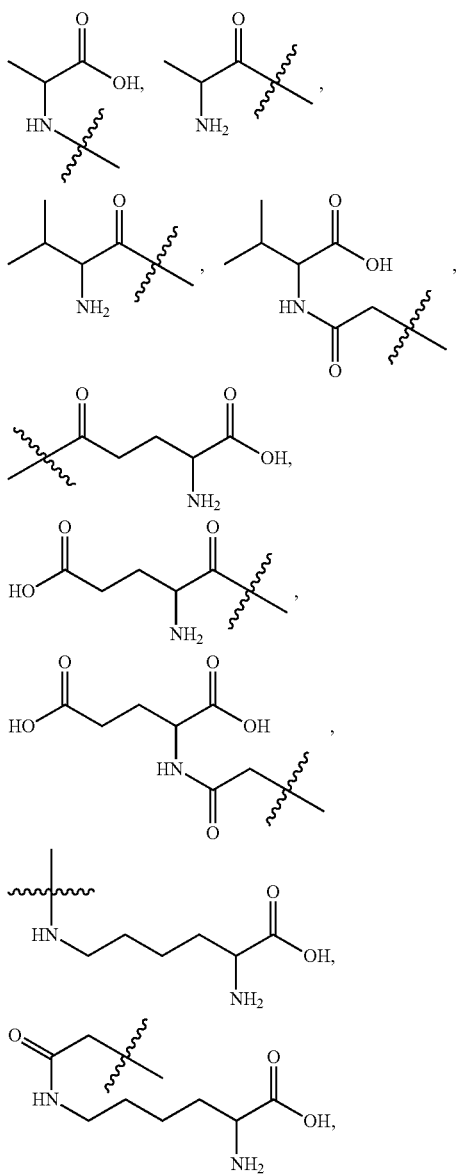

92
-continued

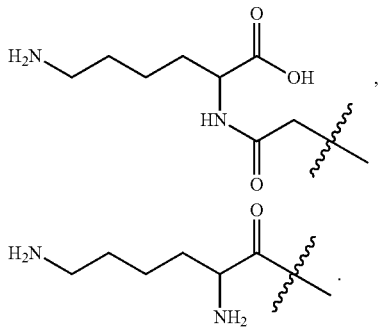

9. The compound of claim 1 or the pharmaceutically acceptable salt, stereoisomer, solvate, isotopically labeled compound, or prodrug thereof, wherein, each $R_1$, at each occurrence, is independently selected from the group consisting of halogen.

10. The compound of claim 1 or the pharmaceutically acceptable salt, stereoisomer, solvate, isotopically labeled compound, or prodrug thereof, wherein, " ═ " represents a single bond, Q is selected from the group consisting of N and CH; W is selected from the group consisting of $CH_2$ and C(═O); or " ═ " represents a double bond, Q is C; W is CH.

11. The compound of claim 1 or the pharmaceutically acceptable salt, stereoisomer, solvate, isotopically labeled compound, or prodrug thereof, wherein the compound has the structure of formula (II):

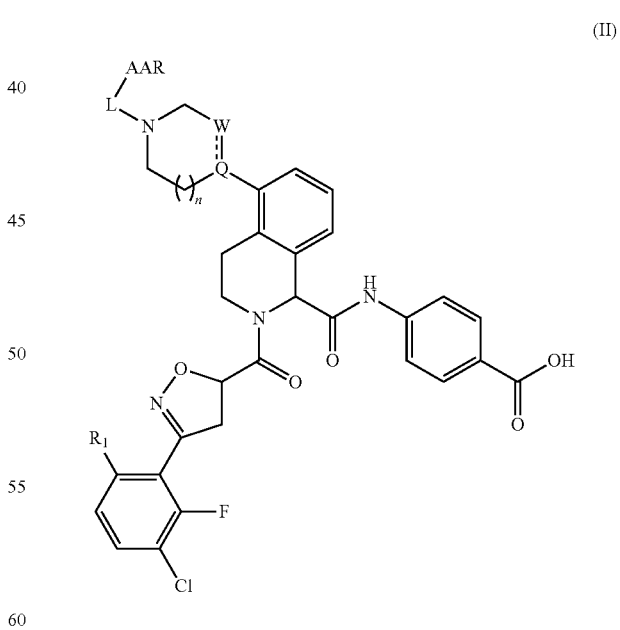

(II)

wherein, ═══, $R_1$, W, Q, L, AAR and n are as defined in claim 1.

12. The compound of claim 11 or the pharmaceutically acceptable salt, stereoisomer, solvate, isotopically labeled compound, or prodrug thereof, wherein the compound has the structure of formula (III):

(III)

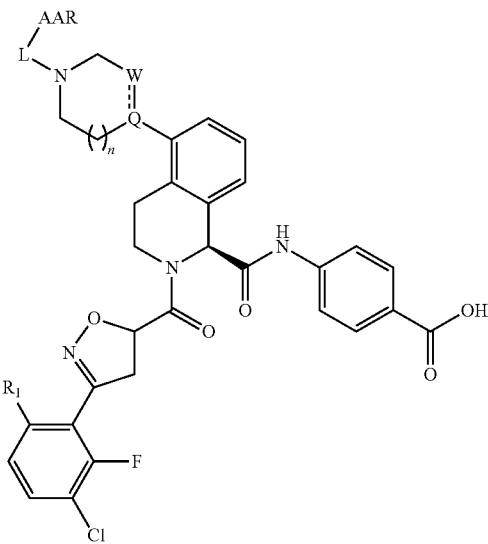

wherein, "═", R$_1$, W, Q, L, AAR and n are as defined in claim 11.

13. The compound of claim 12 or the pharmaceutically acceptable salt, stereoisomer, solvate, isotopically labeled compound, or prodrug thereof, wherein the compound has the structure of formula (IVb):

(IVb)

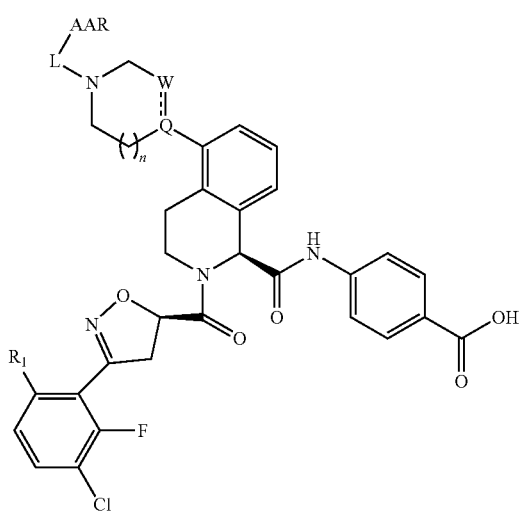

wherein, "═", R$_1$, W, Q, L, AAR and n are as defined in claim 12.

14. The compound of claim 1 or the pharmaceutically acceptable salt, stereoisomer, solvate, isotopically labeled compound, or prodrug thereof, wherein the compound is selected from the group consisting of:

1-a

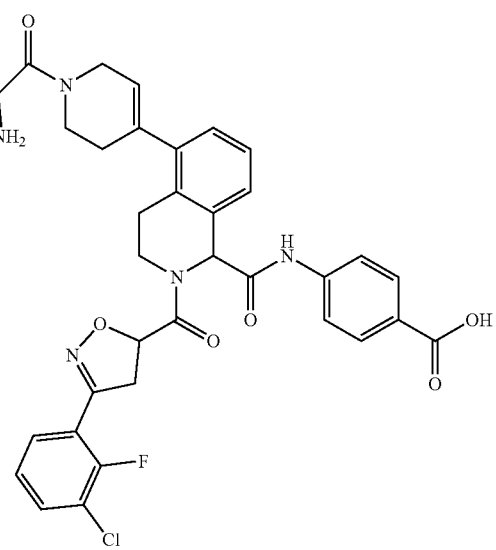

2-a

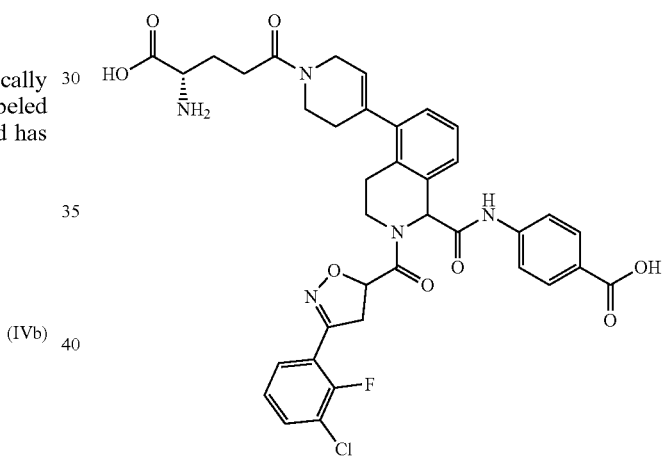

3-a

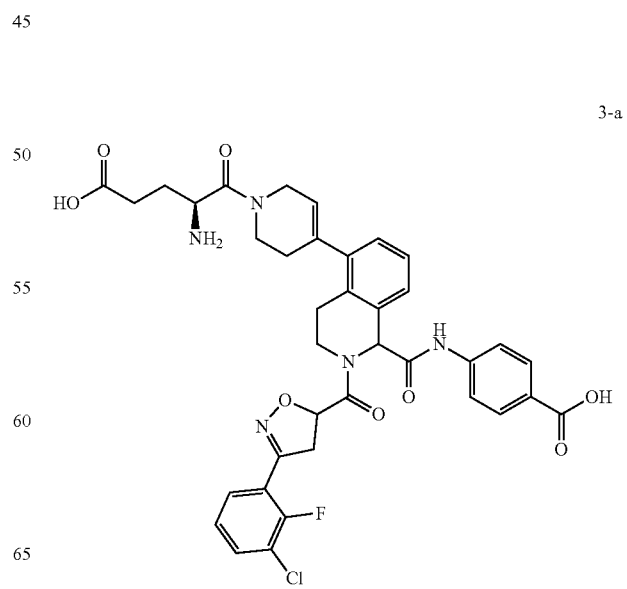

95
1
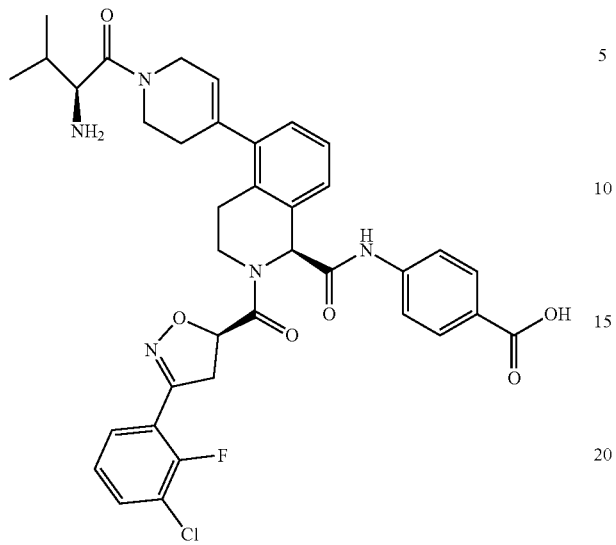
2
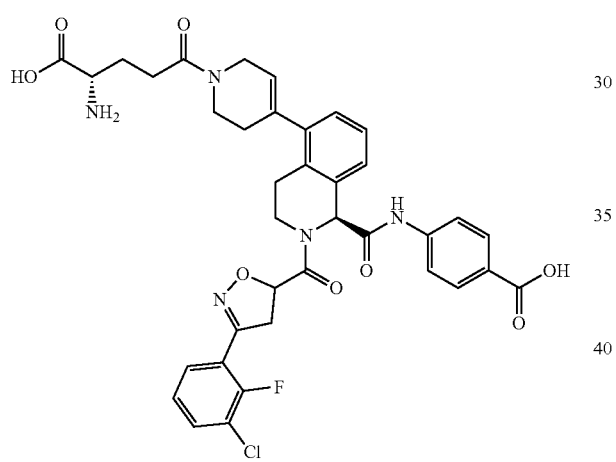
3
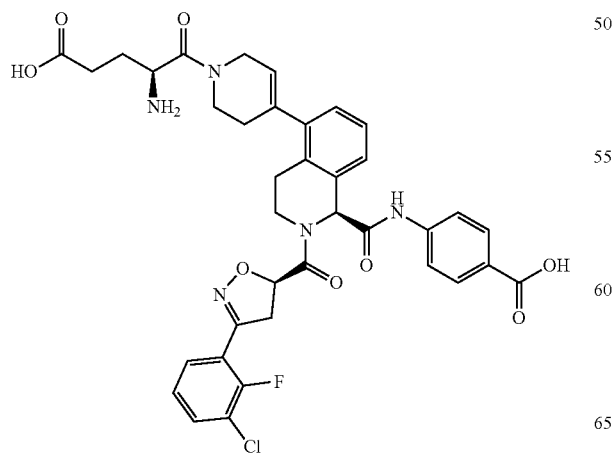
96
4-a
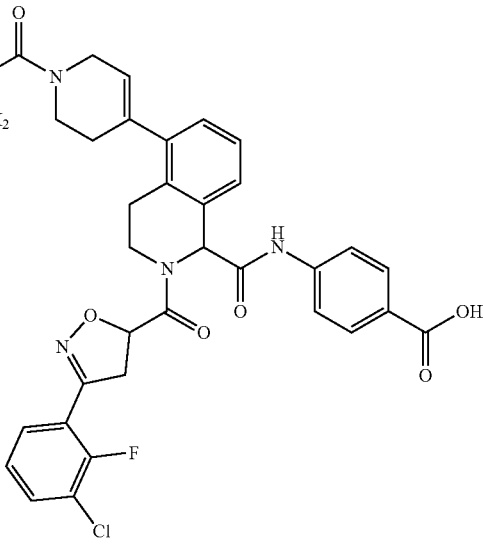
5-a
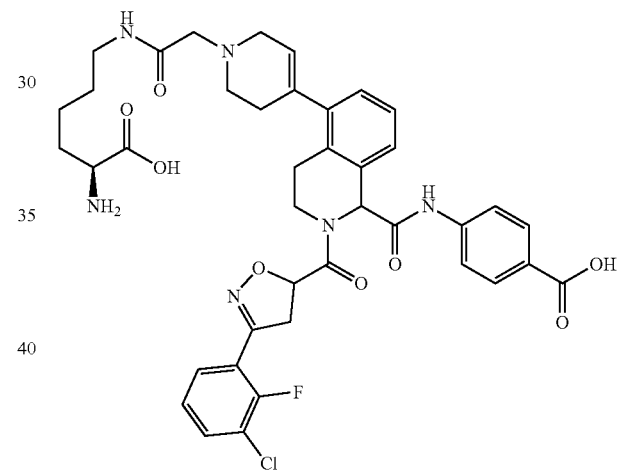
6-a
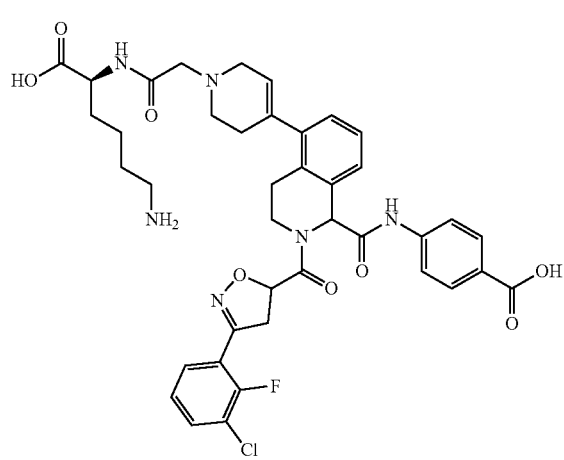

97
-continued
4
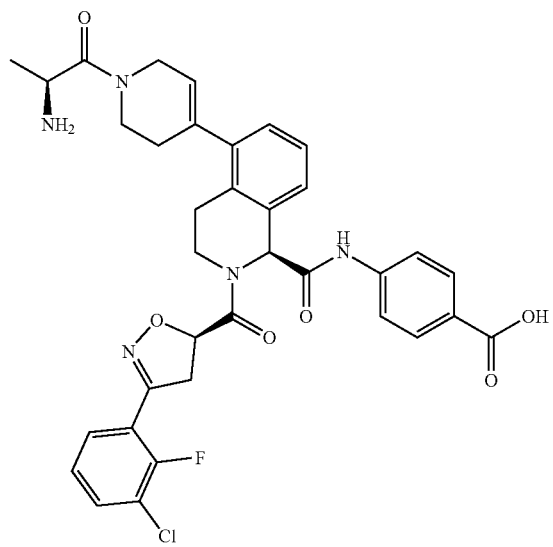
5
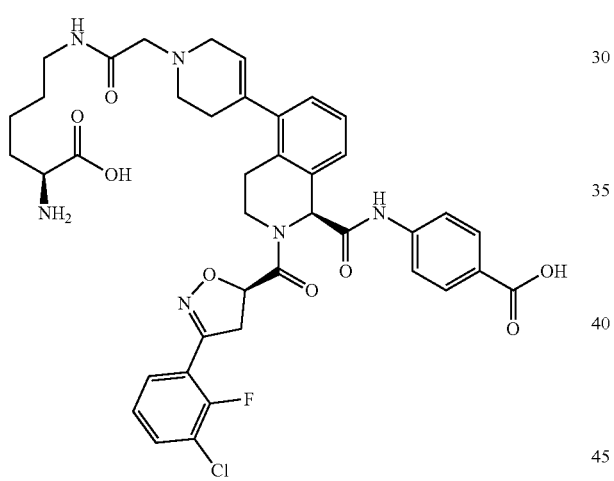
6
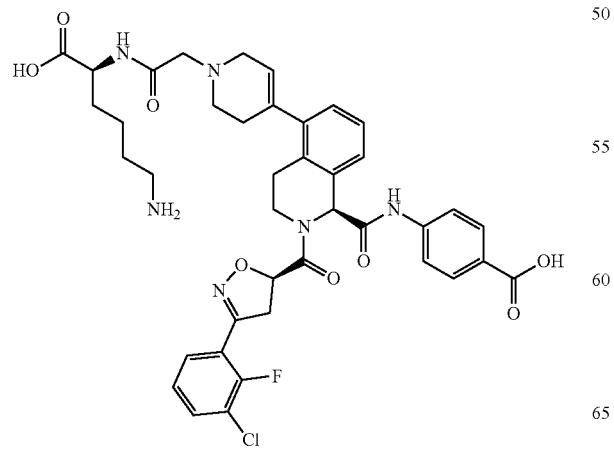
98
-continued
13-a
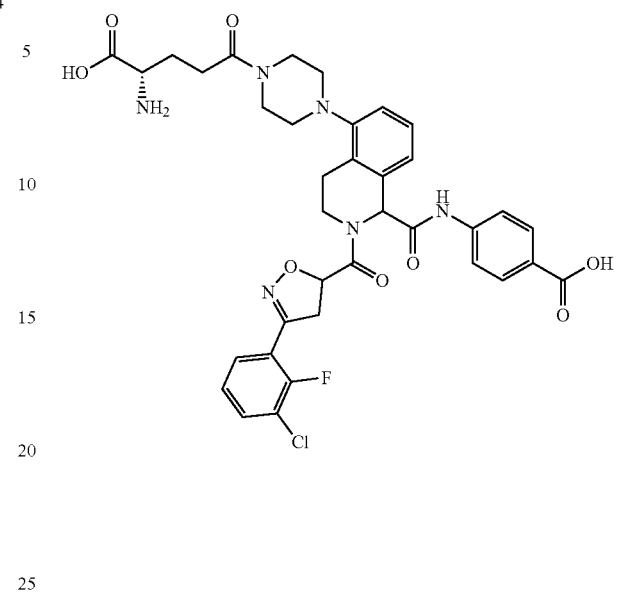
14-a
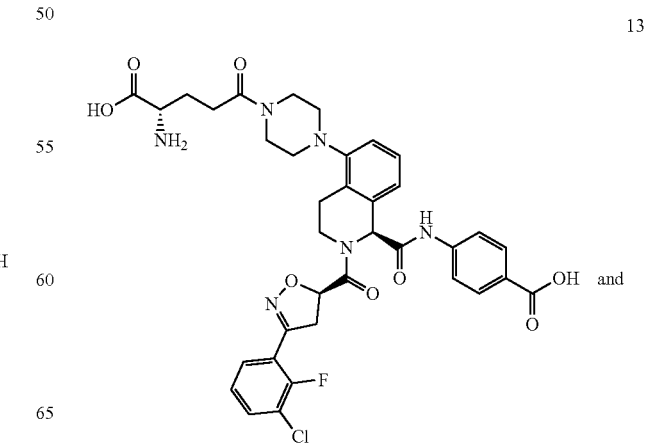
13
and

14

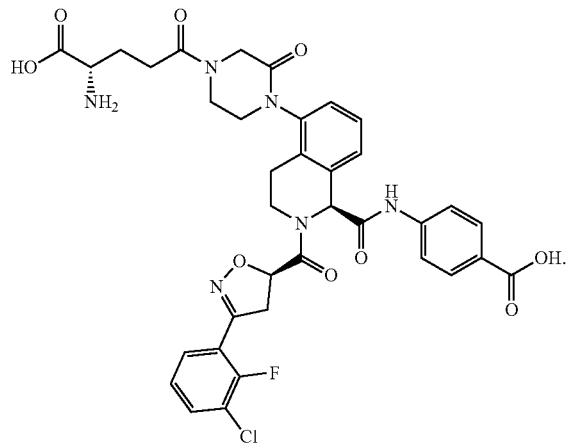

15. The compound of claim 1 or the pharmaceutically acceptable salt, stereoisomer, solvate, isotopically labeled compound, or prodrug thereof, wherein the pharmaceutically acceptable salt is an acid addition salt,
the acid forming the acid addition salt is selected from the group consisting of formic acid, acetic acid, trifluoroacetic acid, hexane diacid, aspartic acid, benzoic acid, benzenesulfonic acid, carbonic acid, sulfuric acid, boric acid, camphorsulfonic acid, citric acid, cyclamic acid, ethylenedisulfonic acid, ethanesulfonic acid, fumaric acid, glucoheptoic acid, gluconic acid, glucuronic acid, hexafluorophosphoric acid, hydrobromic acid, hydroiodic acid, isethionic acid, lactic acid, malic acid, maleic acid, malonic acid, methanesulfonic acid, methylsulfuric acid, naphthoic acid, 2-naphthalenesulfonic acid, nicotinic acid, nitric acid, orotic acid, oxalic acid, palmitic acid, pamoic acid, phosphoric acid, pyroglutamic acid, aldaric acid, stearic acid, succinic acid, tannic acid, tartaric acid and toluenesulfonic acid.

16. A pharmaceutical composition comprising a prophylactically or therapeutically effective amount of the compound of claim 1 or the pharmaceutically acceptable salt, stereoisomer, solvate, isotopically labeled compound, or prodrug thereof, or a mixture thereof, and one or more pharmaceutically acceptable carriers.

17. A pharmaceutical composition comprising a prophylactically or therapeutically effective amount of the compound of claim 14 or the pharmaceutically acceptable salt, stereoisomer, solvate, isotopically labeled compound, or prodrug thereof, or a mixture thereof, and one or more pharmaceutically acceptable carriers.

18. A pharmaceutical composition comprising a prophylactically or therapeutically effective amount of the compound of claim 13 or the pharmaceutically acceptable salt, stereoisomer, solvate, isotopically labeled compound, or prodrug thereof, or a mixture thereof, and one or more pharmaceutically acceptable carriers.

19. A method for treating a coagulation factor XIa inhibition associated disease, comprising administering to a subject in need thereof the compound of claim 1, or the salt, stereoisomer, solvate, isotopically labeled compound, or prodrug thereof, wherein the coagulation factor XIa inhibition associated disease is thromboembolic disorder, the thromboembolic disorder includes arterial cardiovascular thromboembolic disorder, venous cardiovascular thromboembolic disorder or thromboembolic disorder of the heart chamber.

20. The method of claim 19, wherein the thromboembolic disorder includes unstable angina pectoris, acute coronary syndrome, atrial fibrillation, first attack of myocardial infarction, recurrent myocardial infarction, ischemic sudden death, transient ischemic attack, stroke, atherosclerosis, occlusive peripheral arterial disease, phlebothrombosis, deep venous thrombosis, thrombophlebitis, arterial thrombosis, coronary thrombosis, cerebral artery thrombosis, cerebral embolism, kidney embolism, pulmonary embolism, or thrombosis caused by (a) artificial valves or other implants, (b) indwelling catheter, (c) frame, (d) extracorporeal circulation, (e) hemodialysis, or (f) exposure of blood to artificial surface that is prone to form thrombosis.

21. A method for treating a coagulation factor XIa inhibition associated disease, comprising administering to a subject in need thereof the pharmaceutical composition of claim 16, wherein the coagulation factor XIa inhibition associated disease is thromboembolic disorder, the thromboembolic disorder includes arterial cardiovascular thromboembolic disorder, venous cardiovascular thromboembolic disorder or thromboembolic disorder of the heart chamber.

* * * * *